United States Patent
Aissaoui et al.

(10) Patent No.: US 9,637,473 B2
(45) Date of Patent: May 2, 2017

(54) ACRYLAMIDE DERIVATIVES AS ANTIMALARIAL AGENTS

(71) Applicant: Actelion Pharmaceuticals Ltd, Allschwil (CH)

(72) Inventors: Hamed Aissaoui, Allschwil (CH); Christoph Boss, Allschwil (CH); Claire-Lise Ciana, Cropwell Bishop (GB); Thierry Kimmerlin, Allschwil (CH); Romain Siegrist, Allschwil (CH)

(73) Assignee: ACTELION PHARMACEUTICALS LTD., Allschwil (CH)

( * ) Notice: Subject to any disclaimer, the term of this patent is extended or adjusted under 35 U.S.C. 154(b) by 0 days.

(21) Appl. No.: 14/777,459

(22) PCT Filed: Mar. 14, 2014

(86) PCT No.: PCT/IB2014/059801
§ 371 (c)(1),
(2) Date: Sep. 15, 2015

(87) PCT Pub. No.: WO2014/141175
PCT Pub. Date: Sep. 18, 2014

(65) Prior Publication Data
US 2016/0024050 A1 Jan. 28, 2016

(30) Foreign Application Priority Data
Mar. 15, 2013 (EP) .................................... 13159422

(51) Int. Cl.
| C07D 401/12 | (2006.01) |
| C07D 471/04 | (2006.01) |
| C07D 417/14 | (2006.01) |
| C07D 413/14 | (2006.01) |
| C07D 401/14 | (2006.01) |
| C07D 403/12 | (2006.01) |
| C07D 213/75 | (2006.01) |
| C07D 211/58 | (2006.01) |

(52) U.S. Cl.
CPC .......... C07D 401/12 (2013.01); C07D 211/58 (2013.01); C07D 213/75 (2013.01); C07D 401/14 (2013.01); C07D 403/12 (2013.01); C07D 413/14 (2013.01); C07D 417/14 (2013.01); C07D 471/04 (2013.01)

(58) Field of Classification Search
CPC .. C07D 471/04; C07D 417/14; C07D 401/12; C07D 413/14; C07D 401/14; C07D 211/58; C07D 403/12; C07D 213/75
USPC ...................................................... 546/184
See application file for complete search history.

(56) References Cited

U.S. PATENT DOCUMENTS

| 8,067,419 | B2 * | 11/2011 | Binkert | C07D 209/04 514/255.01 |
| 8,889,688 | B2 * | 11/2014 | Aissaoui | C07D 403/12 514/252.11 |
| 2003/0166650 | A1 * | 9/2003 | Wu | C07C 233/11 514/231.5 |
| 2004/0067927 | A1 | 4/2004 | Boss et al. | |
| 2004/0102431 | A1 | 5/2004 | Boss et al. | |
| 2007/0238718 | A1 | 10/2007 | Grauert et al. | |
| 2008/0076762 | A1 | 3/2008 | Boss et al. | |
| 2009/0069320 | A1 * | 3/2009 | Reich | C07D 239/94 514/234.5 |
| 2011/0224210 | A1 * | 9/2011 | Aissaoui | C07C 237/22 514/235.5 |
| 2011/0281869 | A1 * | 11/2011 | Aissaoui | C07D 217/00 514/235.2 |

FOREIGN PATENT DOCUMENTS

| EP | 0 407 200 | 1/1991 |
| JP | 03127732 | 5/1991 |
| WO | WO 00/15657 | 3/2000 |
| WO | WO 02/098856 | 12/2002 |
| WO | WO2004002483 | * 1/2004 |
| WO | WO 2004/032874 | 4/2004 |
| WO | WO2004096771 | * 11/2004 |

(Continued)

OTHER PUBLICATIONS

Cheville; "Pathogenic Protozoa", Chapter 15 in Ultrastructural Pathology, The Comparative Cellular Basis of Disease, Second Ed., Wiley Blackwell, 2009, pp. 524-571.*
Brunner; J Infect Dis. 2012, 206, 735-743.*
Perez; J. Med. Chem. 2013, 56, 556-567.*
Chemical Abstracts STN Registry database record for RN 334660-71-8, entered on May 4, 2001.*
Chemical Abstracts STN Registry database record for RN 294630-42-5, entered on Oct. 11, 2000.*

(Continued)

Primary Examiner — Noble Jarrell
Assistant Examiner — Daniel Carcanague
(74) Attorney, Agent, or Firm — Hoxie & Associates LLC

(57) ABSTRACT

The invention relates to novel acrylamide derivatives of the formula I

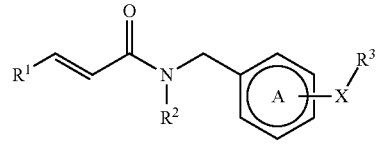

Formula I wherein $R^1$, $R^2$, $R^3$, X, and ring A are as defined in the description, and their use as active ingredients in the preparation of pharmaceutical compositions. The invention also concerns related aspects including pharmaceutical compositions containing those compounds and their use as medicaments for the treatment or prevention of protozoal infections, such as especially malaria.

14 Claims, No Drawings

(56) References Cited

FOREIGN PATENT DOCUMENTS

| WO | WO 2005/013909 | | 2/2005 |
|---|---|---|---|
| WO | WO 2005/019176 | | 3/2005 |
| WO | WO 2005/058822 | | 6/2005 |
| WO | WO 2010/058353 | | 5/2010 |
| WO | WO 2011/083413 | | 7/2011 |
| WO | WO2013018069 | * | 2/2013 |
| WO | WO 2015/028989 | | 3/2015 |

OTHER PUBLICATIONS

Corbett; Bioorganic & Medicinal Chemistry Letters 2005, 15, 4014-4018.*
"Choosing a Drug to Prevent Malaria", Centers for Disease Control and Prevention, Nov. 9, 2012.*
CAS Reg No. 294630-42-5, ComGenex International Inc., Chemical library, (2000).
Cas Reg No. 334660-71-8, ComGenex International Inc., Chemical library, (2001).
Cheng et al., "Studies on the synthesis of 2-propen-1-ones, 2-propenamides and arylacyl hydrazides and their antiparasitic activities", Series of (Doctoral) Medical Science and Technology from Chinese Doctoral Dissertations & Master's Theses Full-Text Database, Issue 1, p. E079-10, (2002).(Partial English Translation).
Cheng et al., "Studies on the synthesis of 2-propen-1-ones, 2-propenamides and arylacyl hydrazides and their antiparasitic activities", Series of (Doctoral) Medical Science and Technology from Chinese Doctoral Dissertations & Master's Theses Full-Text Database, Issue 1, p. E079-10, (2002).(English Abstract only).
Database Chemcats: Chemical Abstracts Service, 2005, XP002420714.
Database Chemcats: Chemical Abstracts Service, 2006, XP002420715.
International Search Report of International Application No. PCT/IB2014/059801 mailed Jun. 24, 2014.
Remington, "Pharmaceutical Manufacturing", The Science and Practice of Pharmacy, 21st Edition, 2005, Part 5.
Stahl et al., "Handbook of Pharmaceutical Salts. Properties, Selection, and Use," International Union of Pure and Applied Chemistry, p. 330-350, (2008).
Van Niel et al., "Fluorination of 3-(3-(Piperidin-1-yl)propyl)indoles and 3-(3-(Piperazin-1-yl)propyl)indoles Gives Selective Human 5-HT1D Receptor Ligands with Improved Pharmacokinetic Profiles," J. Med. Chem., vol. 42, p. 2087-2104, (1999).
Wouters, et al., "Pharmaceutical Salts and Co-crystals," RCS Drug Discovery Series No. 16, p. 1-383, (2012).

* cited by examiner

ACRYLAMIDE DERIVATIVES AS ANTIMALARIAL AGENTS

CROSS-REFERENCE TO RELATED APPLICATIONS

This application is a National Stage Entry of International Application No. PCT/IB2014/059801, filed on Mar. 14, 2014, which claims priority from European Patent Application No. 13159422.8, filed on Mar. 15, 2013, the contents of each of which are hereby incorporated by reference in their entirety.

The invention relates to novel acrylamide derivatives of the formula I. The invention also concerns related aspects including processes for the preparation of the compounds, pharmaceutical compositions containing one or more compounds of the formula I and especially their use as medicaments to treat or prevent malaria infections or to treat or prevent other protozoal diseases like sleeping sickness, Chagas disease, amebiasis, giardiasis, trichomoniasis, toxoplasmosis, and leishmaniasis.

Numerous serious diseases affecting humans as well as domestic and livestock animal are caused by protozoal organisms such as kinetoplastida, *apicomplexa, anaerobic protozoa, microsporidia* and *plasmodium*, for example. The clinically most relevant of these diseases is malaria.

Malaria is one of the most serious and complex health problems affecting humanity in the $21^{st}$ century. The disease affects about 300 million people worldwide, killing 1 to 1.5 million people every year. Malaria is an infectious disease caused by four species of the protozoan parasite *plasmodium*, *P. falciparum* being the most severe of the four. All attempts to develop vaccines against *P. falciparum* have failed so far. Therefore, therapies and preventive measures against malaria are confined to drugs. Various classes of antimalarial drugs exist. The most widely used are the quinoline antimalarials, e.g. chloroquine which has been an especially effective drug for both prophylaxis and therapy. However, resistance to many of the currently available antimalarial drugs is spreading rapidly, threatening people in areas where malaria is endemic. Reports of multi-drug resistant strains of malaria parasites render the search for new antimalarial agents especially urgent.

*P. falciparum* enters the human body by way of bites of the female anophelino mosquito (it may also be transmitted by blood transfusion from asymptotic donors; almost all infected blood components including red cells, platelet concentrates, white cells, cryoprecipitates and fresh plasma can transmit malaria). The *plasmodium* parasite initially populates the liver, and during later stages of the infectious cycle reproduces in red blood cells. During this stage, the parasite degrades hemoglobin and uses the degradation products as nutrients for growth.

The limitations of the current antiprotozoal chemotherapeutic arsenal underscore the need for new drugs in this therapeutic area. The present invention relates to the identification of novel acrylamide derivatives of formula I which are useful in the treatment and/or prevention of protozoal infections, especially in the treatment and/or prevention of malaria, in particular *plasmodium falciparum* malaria.

1) A first embodiment of the present invention relates to compounds of the formula I:

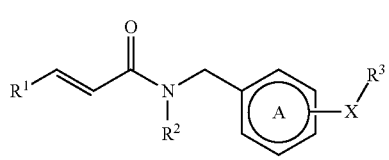

Formula I wherein ring A is a phenylene or pyridin-diyl ring, wherein the group X—$R^3$ is attached to ring A in meta- or para-position with respect to the point of attachment of ring A to the —$CH_2$— group;

$R^1$ represents phenyl, or 5- or 6-membered heteroaryl (notably selected from pyridinyl, imidazolyl, and pyrazolyl, especially pyridinyl); wherein said phenyl or heteroaryl independently is unsubstituted, or mono-, di-, or tri-substituted (especially mono-substituted in para position), wherein the substituents are independently selected from $(C_{1-5})$alkyl, $(C_{1-4})$alkoxy, halogen, cyano, $(C_{1-3})$fluoroalkyl, $(C_{1-3})$fluoroalkoxy, and $(C_{1-3})$alkyl-$SO_2$—;

X represents —$NR^4$— wherein $R^4$ represents hydrogen or $(C_{1-3})$alkyl; —O—; or —(CO)—; and $R^3$ represents
  piperidin-4-yl which is optionally substituted on the nitrogen with $(C_{1-4})$alkyl;
  5- or 6-membered heteroaryl (especially selected from pyridinyl and pyrimidinyl), wherein said heteroaryl independently is unsubstituted, or mono-, or di-substituted wherein the substituents are independently selected from $(C_{1-4})$alkyl, $(C_{1-4})$alkoxy, halogen, $(C_{1-3})$fluoroalkyl, and $(C_{1-3})$fluoroalkoxy;
  8- to 10-membered heteroaryl (especially quinolinyl) wherein said heteroaryl independently is unsubstituted, or mono-, or di-substituted wherein the substituents are independently selected from $(C_{1-4})$alkyl, $(C_{1-4})$alkoxy, halogen, $(C_{1-3})$fluoroalkyl, and $(C_{1-3})$fluoroalkoxy;
  unsubstituted phenyl; or
  4-hydroxy-3-(diethylamino-methyl)-phenyl;

or X represents a direct bond and
  $R^3$ represents
    4-[$(C_{1-4})$alkyl]-piperazin-1-yl or pyrrolidine-1-yl; or
    5- or 6-membered heteroaryl (especially selected from pyridinyl, pyrimidinyl, pyrazolyl, and thiazolyl) wherein said heteroaryl independently is unsubstituted, or mono-substituted with $(C_{1-4})$alkyl;

or X represents O- and $R^3$ represents —$(C_{2-4})$alkylene-$NR^{10}R^{11}$, wherein $R^{10}$ and $R^{11}$ independently represent $(C_{1-3})$alkyl; and $R^2$ represents
  —$(C_{2-4})$alkylene-$NR^{12}K$ wherein $R^{12}$ and $R^{13}$ independently represent $(C_{1-3})$alkyl, or
  $R^{12}$ and $R^{13}$ together with the nitrogen atom to which they are attached to form a morpholine ring; or
  $(C_{3-7})$cycloalkyl which is mono-substituted with $NR^{14}R^{15}$, wherein $R^{14}$ and $R^{15}$ independently represent $(C_{1-3})$alkyl, or $R^{14}$ and $R^{15}$ together with the nitrogen atom to which they are attached to form a pyrrolidine ring; or
  —$(C_{0-2})$alkylene-heterocyclyl, wherein said heterocyclyl is a 4- to 7-membered saturated monocyclic or 7- to 11-membered saturated bicyclic carbocyclic ring containing one ring nitrogen atom; wherein said heterocyclyl may carry one optional substituent attached to a ring carbon atom wherein said substituent is selected from hydroxy and fluoro; and wherein said heterocyclyl is unsubstituted or substituted on said ring nitrogen atom with a substituent selected from:
($C_{1-6}$)alkyl,
($C_{2-3}$)fluoroalkyl;
—($C_{2-4}$)alkylene-($C_{1-4}$)alkoxy;
—($C_{2-4}$)alkylene-$NR^{16}R^{17}$, wherein $R^{16}$ and $R^{17}$ independently represent ($C_{1-3}$)alkyl;
($C_{3-7}$)cycloalkyl;
—($C_{1-3}$)alkylene-($C_{3-7}$)cycloalkyl;
bicyclo[2.2.1]hept-5-en-2-ylmethyl;
piperidin-4-yl, wherein said piperidin group is substituted at the nitrogen atom with ($C_{1-4}$)alkyl;
2,2-diphenylethyl;
3-diethylaminomethyl-4-hydroxy-benzyl;
—($C_{1-3}$)alkylene-phenyl wherein the phenyl group is optionally mono- or di-substituted wherein the substituents are independently selected from ($C_{1-4}$)alkyl, ($C_{1-4}$)alkoxy, halogen, cyano, ($C_{1-3}$)fluoroalkyl, and ($C_{1-3}$)fluoroalkoxy (in particular benzyl, 4-methylbenzyl, 4-cyanobenzyl, 3,4-dichlorobenzyl, 4-methoxybenzyl, 4-trifluoromethyl-benzyl, 1-phenyl-ethyl, or 2-phenyl-ethyl); and
—($C_{1-3}$)alkylene-heteroaryl, wherein the heteroaryl is a 5- to 10-membered heteroaryl (especially selected from thiazolyl, isoxazolyl, oxazolyl, pyrazolyl, imidazolyl, pyridinyl, pyrimidinyl, imidazopyridinyl, benzimidazolyl, indolyl), which is optionally mono- or di-substituted wherein the substituents are independently selected from ($C_{1-4}$)alkyl, ($C_{1-4}$)alkoxy, halogen, ($C_{1-3}$)fluoroalkyl, ($C_{1-3}$)fluoroalkoxy, phenyl, and —(CO)—($C_{1-4}$)alkyl;
with the exception of:
N-[3-(4-morpholinyl)-propyl]-N-[(3-phenoxyphenyl)-methyl]-3-phenyl-2-propenamide (CAS Reg. No 334660-71-8); and
N-[2-(4-morpholinyl)-ethyl]-N-[(3-phenoxyphenyl)-methyl]-3-phenyl-2-propenamide (CAS Reg. No 294630-42-5).

The compounds of formula I may contain one or more stereogenic or asymmetric centers, such as one or more asymmetric carbon atoms. The compounds of formula I may thus be present as mixtures of stereoisomers or preferably as pure stereoisomers. Mixtures of stereoisomers may be separated in a manner known to a person skilled in the art.

Where the plural form is used for compounds, salts, pharmaceutical compositions, diseases and the like, this is intended to mean also a single compound, salt, or the like.

Any reference hereinbefore or hereinafter to a compound of formula I is to be understood as referring also to salts, especially pharmaceutically acceptable salts, of a compound of formula I, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example "Handbook of Pharmaceutical Salts. Properties, Selection and Use.", P. Heinrich Stahl, Camille G. Wermuth (Eds.), Wiley-VCH, 2008; and "Pharmaceutical Salts and Co-crystals", Johan Wouters and Luc Quéré (Eds.), RSC Publishing, 2012.

The present invention also includes isotopically labelled, especially $^2$H (deuterium) labelled compounds of formula I, which compounds are identical to the compounds of formula I except that one or more atoms have each been replaced by an atom having the same atomic number but an atomic mass different from the atomic mass usually found in nature. Isotopically labelled, especially $^2$H (deuterium) labelled compounds of formula I and salts thereof are within the scope of the present invention. Substitution of hydrogen with the heavier isotope $^2$H (deuterium) may lead to greater metabolic stability, resulting e.g. in increased in vivo half-life or reduced dosage requirements, or may lead to reduced inhibition of cytochrome P450 enzymes, resulting e.g. in an improved safety profile. In one embodiment of the invention, the compounds of formula I are not isotopically labelled, or they are labelled only with one or more deuterium atoms. In a sub-embodiment, the compounds of formula I are not isotopically labelled at all. Isotopically labelled compounds of formula I may be prepared in analogy to the methods described hereinafter, but using the appropriate isotopic variation of suitable reagents or starting materials.

In this patent application, a bond drawn as a dotted line shows the point of attachment of the radical drawn. For example, the radical drawn below

is a piperidin-1,4-diyl group.

The following definitions are intended to apply uniformly to the compounds of formula I according to embodiment 1) and, mutatis mutandis, throughout the description and the claims unless an otherwise expressly set out definition provides a broader or narrower definition. It is well understood that a definition or preferred definition of a term as defined herein below or anywhere else in the description or the claims defines and may replace the respective term independently of (and in combination with) any definition or preferred definition of any or all other terms as defined herein.

The term "halogen" refers to fluorine, chlorine, or bromine, preferably fluorine or chlorine.

The term "alkyl", used alone or in combination, refers to a saturated straight or branched hydrocarbon group containing from one to six carbon atoms. The term "($C_{x-y}$)alkyl" (x and y each being an integer), refers to an alkyl group as defined before, containing x to y carbon atoms. For example a ($C_{1-4}$)alkyl group contains from one to four carbon atoms. Examples of alkyl groups are methyl, ethyl, propyl, isopropyl, n-butyl, isobutyl, sec.-butyl and tert.-butyl. Preferred are methyl and ethyl. Most preferred is methyl.

The term "alkylene", used alone or in combination, refers to a bivalently bound alkyl group as defined before, wherein the term "—($C_0$)alkylene" means that such group is absent, i.e. the two attached groups are linked through a direct bond. Preferably, the points of attachment of any bivalently bound alkyl group are in 1,1-diyl, or in 1,2-diyl arrangement. Examples of alkylene groups, such as for example in the terms "—($C_{1-3}$)alkylene-heteroaryl" and "—($C_{1-3}$)alkylene-phenyl", are methylene, ethylene, and ethane-1,1-diyl; preferably methylene. In case an alkylene group links two heteroatoms, ethylene is preferred. For the term "—($C_{0-2}$)alkylene-heterocyclyl" as used for the substituent $R^2$, the —(C$_{0-2}$)alkylene- group refers to a —(C$_{0-2}$)alkylene- group as defined before; wherein preferably said group is —(C$_0$)alkylene, i.e. it is absent, or less preferred, it is a methylene group.

The term "cycloalkyl", used alone or in combination, refers to a saturated cyclic alkyl group containing three to seven carbon atoms. The term "(C$_{x-y}$)cycloalkyl" (x and y each being an integer), refers to a cycloalkyl group as defined before containing x to y carbon atoms. For example a (C$_{3-7}$)cycloalkyl group contains from three to seven carbon atoms. Examples of cycloalkyl groups are cyclopropyl, cyclobutyl, cyclopentyl and cyclohexyl. Preferred for substituents of the R$^2$ being heterocyclyl is cyclopentyl.

The term "—(C$_{1-3}$)alkylene-(C$_{3-7}$)cycloalkyl" refers to a (C$_{3-7}$)cycloalkyl group as defined before which is linked to the rest of the molecule through a (C$_{1-3}$)alkylene group as defined before. An example is cyclopropylmethyl.

The term "alkoxy", used alone or in combination, refers to an alkyl-O— group wherein the alkyl group is as defined before. The term "(C$_{x-y}$)alkoxy" (x and y each being an integer) refers to an alkoxy group as defined before containing x to y carbon atoms. For example a (C$_{1-4}$)alkoxy group means a group of the formula (C$_{1-4}$)alkyl-O— in which the term "(C$_{1-4}$)alkyl" has the previously given significance. Examples of alkoxy groups are methoxy, ethoxy, n-propoxy, isopropoxy, n-butoxy, isobutoxy, sec.-butoxy and tert.-butoxy. Preferred are ethoxy and especially methoxy.

The term "fluoroalkyl" refers to an alkyl group as defined before containing one to three carbon atoms in which one or more (and possibly all) hydrogen atoms have been replaced with fluorine. The term "(C$_{x-y}$)fluoroalkyl" (x and y each being an integer) refers to a fluoroalkyl group as defined before containing x to y carbon atoms. For example a (C$_{1-3}$)fluoroalkyl group contains from one to three carbon atoms in which one to seven hydrogen atoms have been replaced with fluorine. Representative examples of fluoroalkyl groups include trifluoromethyl, 2-fluoroethyl, 2,2-difluoroethyl, 2,2,2-trifluoroethyl, and 3,3,3-trifluoropropyl. A preferred (C$_{1-3}$)fluoroalkyl group as used for substituents of R$^1$ is trifluoromethyl. A preferred (C$_{2-3}$)fluoroalkyl group is 3,3,3-trifluoropropyl.

The term "fluoroalkoxy" refers to an alkoxy group as defined before containing one to three carbon atoms in which one or more (and possibly all) hydrogen atoms have been replaced with fluorine. The term "(C$_{x-y}$)fluoroalkoxy" (x and y each being an integer) refers to a fluoroalkoxy group as defined before containing x to y carbon atoms. For example a (C$_{1-3}$)fluoroalkoxy group contains from one to three carbon atoms in which one to seven hydrogen atoms have been replaced with fluorine. Representative examples of fluoroalkoxy groups include trifluoromethoxy, difluoromethoxy, 2-fluoroethoxy, 2,2-difluoroethoxy and 2,2,2-trifluoroethoxy. Preferred (C$_{1-3}$)fluoroalkoxy groups as used for substituents of R$^1$ are trifluoromethoxy and difluoromethoxy.

The term "heterocyclyl", alone or in combination with other groups, as used for the substituent R$^2$ means a 4-, 5-, 6-, or 7-membered saturated monocyclic hydrocarbon ring containing one nitrogen atom; or a 7-, 8-, 9-, 10-, or 11-membered saturated bicyclic hydrocarbon ring system containing one nitrogen atom (wherein it is understood that said nitrogen atom has a free valency, i.e. it is not a bridgehead atom; and wherein the term bicyclic hydrocarbon ring system is to be understood as comprising bicyclic bridged ring systems, bicyclic fused ring systems, and, preferably, bicyclic spiro-ring systems). Examples of such heterocyclyl groups which do not carry one optional substituent attached to a ring carbon atom are monocyclic heterocyclyl groups such as azetidinyl (especially azetidin-3-yl), pyrrolidinyl (especially pyrrolidin-3-yl), piperidinyl (especially piperidin-3-yl, piperidin-4-yl), and azepanyl (especially azepan-3-yl, azepan-4-yl); and bicyclic heterocyclyl groups, especially bicyclic spiro-heterocyclyl groups, such as 2-aza-spiro[3.3]hept-6-yl, octahydro-cyclopenta[c]pyrrol-5-yl, and 3-aza-spiro[5.5]undec-9-yl. Examples of such heterocyclyl groups which carry one optional substituent attached to a ring carbon atom are notably substituted monocyclic heterocyclyl groups, such as 1-hydroxy-piperidin-4-yl, and, especially, 3-fluoro-piperidin-4-yl. Preferred heterocyclyl groups as used for the substituent R$^2$ are piperidinyl (especially piperidin-3-yl, piperidin-4-yl, 3-fluoro-piperidin-4-yl), 2-aza-spiro[3.3]hept-6-yl, and 3-aza-spiro[5.5]undec-9-yl.

Examples of R$^1$ representing a phenyl group are notably phenyl groups mono-substituted para-position. Examples are phenyl, 2-methyl-phenyl, 3-methyl-phenyl, 2-methoxy-phenyl, 3-methoxy-phenyl, 2-fluoro-phenyl, 3-fluoro-phenyl, 2-chloro-phenyl, and 3-chloro-phenyl; and especially the para-substituted groups 4-trifluoromethyl-phenyl, 4-trifluoromethoxy-phenyl, 4-difluoromethoxy-phenyl, 4-fluoro-phenyl, 4-chloro-phenyl, 4-cyano-phenyl, 4-methyl-phenyl, 4-ethyl-phenyl, 4-tert.-butyl-phenyl, 4-methoxy-phenyl, 4-iso-propoxy-phenyl, 4-n-propoxy-phenyl, and 4-methanesulfonyl-phenyl. Preferred is 4-trifluoromethyl-phenyl.

The term "heteroaryl", if not explicitly stated otherwise, refers to a 5- to 10-membered monocyclic, or bicyclic aromatic ring containing 1 to a maximum of 3 heteroatoms independently selected from oxygen, nitrogen and sulfur. Examples of such heteroaryl groups are 5-membered monocyclic heteroaryl groups such as furanyl, oxazolyl, isoxazolyl, oxadiazolyl, thienyl, thiazolyl, isothiazolyl, thiadiazolyl, pyrrolyl, imidazolyl, pyrazolyl, and triazolyl; 6-membered monocyclic heteroaryl such as pyridyl, pyrimidyl, pyridazinyl, and pyrazinyl; and 8- to 10-membered bicyclic heteroaryl such as indolyl, isoindolyl, benzofuranyl, isobenzofuranyl, benzothiophenyl, indazolyl, benzimidazolyl, benzoxazolyl (or benzooxazolyl), benzisoxazolyl, benzothiazolyl, benzoisothiazolyl, benzotriazolyl, benzoxadiazolyl, benzothiadiazolyl, quinolinyl, isoquinolinyl, naphthyridinyl, cinnolinyl, quinazolinyl, quinoxalinyl, phthalazinyl, pyrazolopyridyl (especially pyrazolo[1,5-a]pyridyl, pyrazolo[1,5-a]pyrimidyl), imidazopyridyl (especially imidazo[1,2-a]pyridyl), pyrrolopyridyl (especially 1H-pyrrolo[3,2-b]pyridyl, 1H-pyrrolo[2,3-b]pyridyl), pyrrolopyrimidinyl (especially pyrrolo[3,2-d]pyrimidinyl, pyrrolo[2,3-d]pyrimidinyl), 4H-furo[3,2-b]pyrrolyl, pyrrolo[2,1-b]thiazolyl, imidazo[2,1-b]thiazolyl and purinyl.

For —(C$_{1-3}$)alkylene-heteroaryl which are substituents of the group R$^2$ being —(C$_{0-2}$)alkylene-heterocyclyl, examples of heteroaryl groups are 5-membered heteroaryl such as especially thiazolyl, isoxazolyl, oxazolyl, pyrazolyl, and imidazolyl; 6-membered heteroaryl containing one or two nitrogen atoms such as especially pyridinyl and pyrimidinyl; and 8- to 10-membered (especially 9-membered) heteroaryl containing one or two nitrogen atoms such as imidazopyridinyl, benzimidazolyl, and indolyl. The above-mentioned groups are unsubstituted or substituted as explicitly defined. 9-Membered heteroaryl groups preferably are unsubstituted or mono-substituted on a nitrogen atom having a free vacancy.

For 5- or 6-membered heteroaryl groups as used for the substituent R$^3$, examples of heteroaryl groups are 5-membered heteroaryl such as pyrazolyl and thiazolyl; and especially 6-membered heteroaryl containing one or two nitrogen atoms such as pyridinyl and pyrimidinyl. For 8- to 10-membered heteroaryl groups as used for the substituent $R^3$, examples of heteroaryl groups are 8- to 10-membered (especially 9-membered) heteroaryl groups containing one or two nitrogen atoms such as especially quinolinyl. The above-mentioned groups are unsubstituted or substituted as explicitly defined.

For 5- or 6-membered heteroaryl groups as used for the substituent $R^1$, examples of heteroaryl groups are 5-membered heteroaryl groups containing one to three nitrogen atoms such as especially imidazolyl and pyrazolyl; and 6-membered heteroaryl containing one or two nitrogen atoms such as especially pyridinyl. The above-mentioned groups are unsubstituted or substituted as explicitly defined. Notably the above-mentioned 5-membered heteroaryl groups are mono-, di-, or tri-substituted with methyl; and the above-mentioned 6-membered heteroaryl groups are mono-substituted with trifluoromethyl.

Examples of pyridin-diyl rings which are di-substituted in meta or para position as used for ring A are pyridin-2,6-diyl, pyridin-2,5-diyl, pyridin-2,4-diyl, and pyridin-3,5-diyl; preferred is pyridin-2,5-diyl.

An example of a $(C_{1-3})$alkyl-$SO_2$— group is methanesulfonyl.

An example of a "4-[$(C_{1-4})$alkyl]-piperazin-1-yl" group is 4-methyl-piperazin-1-yl.

An example of a "—$(C_{2-4})$alkylene-$NR^{10}R^{11}$" group is 3-dimethylamino-propyl.

Examples of "—$(C_{2-4})$alkylene-$NR^{12}R^{13}$" groups are 2-dimethylamino-ethyl, 2-dimethylamino-1-methyl-ethyl, 3-dimethylamino-propyl, and 3-(morpholin-4-yl)-propyl.

Examples of "$(C_{3-7})$cycloalkyl which is mono-substituted with $NR^{14}R^{15}$" groups are 4-dimethylamino-cyclohexyl, and 4-(pyrrolidin-1-yl)-cyclohexyl.

An example of a "—$(C_{2-4})$alkylene-$NR^{16}R^{17}$" group is 2-dimethylamino-ethyl.

An example of a "piperidin-4-yl, wherein said piperidin group is substituted at the nitrogen atom with $(C_{1-4})$alkyl" group is 1-methyl-piperidin-4-yl.

Further embodiments of the invention are presented hereinafter:

2) A second embodiment of the invention relates to compounds of the formula I according to embodiment 1), which are also compounds of the formula II

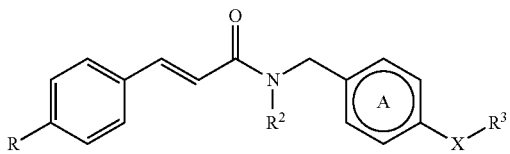

Formula II wherein
ring A is 1,4-phenylene, or pyridin-2,5-diyl (wherein X is preferably attached in position 2);
R represents $(C_{1-5})$alkyl, $(C_{1-4})$alkoxy, halogen, cyano, $(C_{1-3})$fluoroalkyl, $(C_{1-3})$fluoroalkoxy, or $(C_{1-3})$alkyl-$SO_2$— (especially trifluoromethyl);
X represents —$NR^4$— wherein $R^4$ represents hydrogen or methyl; or —O—; and $R^3$ represents
piperidin-4-yl which is optionally substituted on the nitrogen with $(C_{1-4})$alkyl;
5- or 6-membered heteroaryl (especially selected from pyridinyl and pyrimidinyl), wherein said heteroaryl independently is especially unsubstituted, or mono-, or di-substituted wherein the substituents are independently selected from $(C_{1-4})$alkyl, $(C_{1-4})$alkoxy, and halogen;
10-membered heteroaryl (especially quinolinyl) wherein said heteroaryl independently is unsubstituted, or mono-, or di-substituted wherein the substituents are independently selected from $(C_{1-4})$alkyl, $(C_{1-4})$alkoxy, halogen, and $(C_{1-3})$fluoroalkyl;
unsubstituted phenyl; or
4-hydroxy-3-(diethylamino-methyl)-phenyl;
or X represents a direct bond and
$R^3$ represents
4-[$(C_{1-4})$alkyl]-piperazin-1-yl or pyrrolidine-1-yl; or
5- or 6-membered heteroaryl (especially selected from pyridinyl, pyrimidinyl, pyrazolyl, and thiazolyl) wherein said heteroaryl independently is unsubstituted, or mono-substituted with $(C_{1-4})$alkyl;
or X represents —O— and $R^3$ represents —$(C_{2-4})$alkylene-$NR^{10}R^{11}$, wherein $R^{10}$ and $R^{11}$ independently represent $(C_{1-3})$alkyl; and
$R^2$ represents
—$(C_{2-4})$alkylene-$NR^{12}R^{13}$, wherein $R^{12}$ and $R^{13}$ independently represent $(C_{1-3})$alkyl, or $R^{12}$ and $R^{13}$ together with the nitrogen atom to which they are attached to form a morpholine ring; or
$(C_{3-7})$cycloalkyl which is mono-substituted with $NR^{14}R^{15}$, wherein $R^{14}$ and $R^{15}$ independently represent $(C_{1-3})$alkyl, or $R^{14}$ and $R^{15}$ together with the nitrogen atom to which they are attached to form a pyrrolidine ring; or
heterocyclyl, wherein said heterocyclyl is a 4- to 7-membered saturated monocyclic or 7- to 11-membered saturated bicyclic carbocyclic ring containing one ring nitrogen atom; wherein said heterocyclyl may carry one optional fluoro substituent attached to a ring carbon atom; and wherein said heterocyclyl is substituted on said ring nitrogen atom with a substituent selected from:
$(C_{1-6})$alkyl,
$(C_{2-3})$fluoroalkyl;
—$(C_{2-4})$alkylene-$(C_{1-4})$alkoxy;
—$(C_{2-4})$alkylene-$NR^{16}R^{17}$, wherein $R^{16}$ and $R^{17}$ independently represent $(C_{1-3})$alkyl;
$(C_{3-7})$cycloalkyl;
—$(C_{1-3})$alkylene-$(C_{3-7})$cycloalkyl;
bicyclo[2.2.1]hept-5-en-2-ylmethyl;
piperidin-4-yl, wherein said piperidin group is substituted at the nitrogen atom with $(C_{1-4})$alkyl;
2,2-diphenylethyl;
3-diethylaminomethyl-4-hydroxy-benzyl;
—$(C_{1-3})$alkylene-phenyl wherein the phenyl group is optionally mono- or di-substituted wherein the substituents are independently selected from $(C_{1-4})$alkyl, $(C_{1-4})$alkoxy, halogen, cyano, and $(C_{1-3})$fluoroalkyl (in particular benzyl, 4-methylbenzyl, 4-cyanobenzyl, 3,4-dichlorobenzyl, 4-methoxybenzyl, 4-trifluoromethyl-benzyl, 1-phenyl-ethyl, or 2-phenyl-ethyl); and
—$(C_{1-3})$alkylene-heteroaryl, wherein the heteroaryl is a 5- to 10-membered heteroaryl (especially selected from thiazolyl, isoxazolyl, oxazolyl, pyrazolyl, imidazolyl, pyridinyl, pyrimidinyl, imidazopyridinyl, benzimidazolyl, indolyl);
wherein said heteroaryl is independently unsubstituted, or mono- or di-substituted wherein the substituents are independently selected from $(C_{1-4})$alkyl, phenyl, and —(CO)—$(C_{1-4})$alkyl.

3) A further embodiment relates to compounds according to embodiments 1) or 2), wherein ring A is 1,4-phenylene, or pyridin-2,5-diyl wherein X is attached in position 2.

4) A further embodiment relates to compounds according to any one of embodiments 1) to 3), wherein $R^1$ represents 4-trifluoromethylphenyl, respectively, R represents trifluoromethyl.

5) A further embodiment relates to compounds according to any one of embodiments 1) to 4), wherein
X represents —$NR^4$— wherein $R^4$ represents hydrogen or methyl; and
$R^3$ represents
  piperidin-4-yl which is optionally substituted on the nitrogen with $(C_{1-3})$alkyl;
  6-membered heteroaryl selected from pyridinyl and pyrimidinyl (notably pyridinyl, especially pyridin-4-yl), wherein said heteroaryl independently is unsubstituted, or mono-, or di-substituted wherein the substituents are independently selected from methyl, methoxy, and fluoro (especially unsubstituted or mono-substituted with methyl);
  quinolinyl which is mono-, or di-substituted wherein the substituents are independently selected from methyl, methoxy, chloro, and trifluoromethyl;
  4-hydroxy-3-(diethylamino-methyl)-phenyl;
or X represents a direct bond and
$R^3$ represents
  4-[$(C_{1-4})$alkyl]-piperazin-1-yl or pyrrolidine-1-yl; or
  5- or 6-membered heteroaryl selected from pyridinyl, pyrimidinyl, pyrazolyl, and thiazolyl, wherein said heteroaryl independently is unsubstituted, or mono-substituted with methyl;
or X represents 0- and $R^3$ represents dimethylaminopropyl.

6) A further embodiment relates to compounds according to any one of embodiments 1) to 4), wherein
X represents —$NR^4$— wherein $R^4$ represents hydrogen or methyl; and
$R^3$ represents
  piperidin-4-yl which is optionally substituted on the nitrogen with $(C_{1-3})$alkyl; or
  6-membered heteroaryl selected from pyridinyl and pyrimidinyl (notably pyridinyl, especially pyridin-4-yl), wherein said heteroaryl independently is unsubstituted, or mono-, or di-substituted wherein the substituents are independently selected from methyl, methoxy, and fluoro (especially unsubstituted or mono-substituted with methyl).

7) A further embodiment relates to compounds according to any one of embodiments 1) to 6), wherein
$R^2$ represents 2-dimethylamino-ethyl, 2-dimethylamino-1-methyl-ethyl, 3-dimethylamino-propyl, 3-(morpholin-4-yl)-propyl, 4-dimethylamino-cyclohexyl, or 4-(pyrrolidin-1-yl)-cyclohexyl;
or $R^2$ represents heterocyclyl, wherein said heterocyclyl is a 4- to 7-membered saturated monocyclic or 7- to 11-membered saturated bicyclic carbocyclic ring containing one ring nitrogen atom; wherein said heterocyclyl may carry one optional fluoro substituent attached to a ring carbon atom; and wherein said heterocyclyl is substituted on said ring nitrogen atom with a substituent selected from:
  methyl, ethyl, iso-propyl, n-propyl, 3-methylbutyl;
  3,3,3-trifluoropropyl;
  2-methoxy-1-methyl-ethyl;
  2-dimethylamino-ethyl;
  cyclopropyl, cyclopentyl;
  cyclopropyl-methyl;
  bicyclo[2.2.1]hept-5-en-2-ylmethyl;
  1-methyl-piperidin-4-yl;
  —$(C_{1-3})$alkylene-phenyl wherein the phenyl group is optionally mono- or di-substituted wherein the substituents are independently selected from methyl, methoxy, halogen, cyano, and trifluoromethyl (in particular benzyl, 4-methylbenzyl, 4-cyanobenzyl, 3,4-dichlorobenzyl, 4-methoxybenzyl, 4-trifluoromethylbenzyl, 1-phenyl-ethyl, or 2-phenyl-ethyl); and
  —$(CH_2)$-heteroaryl, wherein the heteroaryl is a 5- to 10-membered heteroaryl selected from thiazolyl, isoxazolyl, oxazolyl, pyrazolyl, imidazolyl, pyridinyl, pyrimidinyl, imidazopyridinyl, benzimidazolyl, and indolyl; wherein said heteroaryl is independently unsubstituted or mono- or di-substituted with methyl.

8) A further embodiment relates to compounds according to any one of embodiments 1) to 7), wherein, in case $R^2$ represents —$(C_{0-2})$alkylene-heterocyclyl, such group is directly bound heterocyclyl (i.e. the —$(C_{0-2})$alkylene- group is absent as defined for the compounds of embodiments 2) or 7)), wherein said heterocyclyl is selected from azetidinyl (especially azetidin-3-yl), pyrrolidinyl (especially pyrrolidin-3-yl), piperidinyl (especially piperidin-3-yl, piperidin-4-yl), and azepanyl (especially azepan-3-yl, azepan-4-yl); and the bicyclic heterocyclyl groups 2-aza-spiro[3.3]hept-6-yl, octahydro-cyclopenta[c]pyrrol-5-yl, and 3-aza-spiro[5.5]undec-9-yl; wherein in case said herocyclyl is piperidinyl said heterocyclyl may carry one optional fluoro substituent attached to a ring carbon atom (especially the ring carbon atom in position 3); and wherein said heterocyclyl is substituted on the ring nitrogen atom as explicitly defined.

9) A further embodiment relates to compounds according to any one of embodiments 1) to 7), wherein, in case $R^2$ represents —$(C_{0-2})$alkylene-heterocyclyl, such group is directly bound heterocyclyl (i.e. the —$(C_{0-2})$alkylene- group is absent as defined for the compounds of embodiments 2) or 7)), wherein said heterocyclyl is selected from piperidin-3-yl, piperidin-4-yl, 3-fluoro-piperidin-4-yl, 2-aza-spiro[3.3]hept-6-yl, and 3-aza-spiro[5.5]undec-9-yl; wherein said heterocyclyl is independently substituted on the ring nitrogen atom as explicitly defined.

10) A further embodiment relates to compounds according to any one of embodiments 1) to 6), wherein $R^2$ represents heterocyclyl selected from azetidinyl (especially azetidin-3-yl), pyrrolidinyl (especially pyrrolidin-3-yl), piperidinyl (especially piperidin-3-yl, piperidin-4-yl), azepanyl (especially azepan-3-yl, azepan-4-yl), 2-aza-spiro[3.3]hept-6-yl, octahydro-cyclopenta[c]pyrrol-5-yl, and 3-aza-spiro[5.5]undec-9-yl; wherein in case said herocyclyl is piperidinyl, said heterocyclyl may carry one optional fluoro substituent attached to a ring carbon atom; [especially such group is selected from piperidin-3-yl, piperidin-4-yl, 3-fluoro-piperidin-4-yl, 2-aza-spiro[3.3]hept-6-yl, and 3-aza-spiro[5.5]undec-9-yl]; wherein said heterocyclyl is independently substituted on said ring nitrogen atom with a substituent selected from:
  methyl, ethyl, iso-propyl, n-propyl, 3-methylbutyl;
  3,3,3-trifluoropropyl;
  2-methoxy-1-methyl-ethyl;
  2-dimethylamino-ethyl;
  cyclopropyl, cyclopentyl;

cyclopropyl-methyl;
bicyclo[2.2.1]hept-5-en-2-ylmethyl;
1-methyl-piperidin-4-yl;
—(C$_{1-3}$)alkylene-phenyl wherein the phenyl group is optionally mono- or di-substituted wherein the substituents are independently selected from methyl, methoxy, halogen, cyano, and trifluoromethyl (in particular benzyl, 4-methylbenzyl, 4-cyanobenzyl, 3,4-dichlorobenzyl, 4-methoxybenzyl, 4-trifluoromethyl-benzyl, 1-phenyl-ethyl, or 2-phenyl-ethyl); and
—(CH$_2$)-heteroaryl, wherein the heteroaryl is a 5- to 10-membered heteroaryl selected from thiazolyl, isoxazolyl, oxazolyl, pyrazolyl, imidazolyl, pyridinyl, pyrimidinyl, imidazopyridinyl, benzimidazolyl, and indolyl; wherein said heteroaryl is independently unsubstituted or mono- or di-substituted with methyl.

11) A further embodiment relates to compounds according to any one of embodiments 1) to 6), wherein R$^2$ represents heterocyclyl selected from piperidin-3-yl, piperidin-4-yl, 3-fluoro-piperidin-4-yl, 2-aza-spiro[3.3]hept-6-yl, and 3-aza-spiro[5.5]undec-9-yl; wherein said heterocyclyl is independently substituted on the ring nitrogen atom with cyclopentyl or 1-methyl-piperidin-4-yl.

12) The invention, thus, relates to compounds of the formula I as defined in embodiment 1), or to such compounds further limited by the characteristics of any one of embodiments 2) to 11), under consideration of their respective dependencies; to pharmaceutically acceptable salts thereof; and to such compounds or pharmaceutically acceptable salts thereof for use as medicaments, especially for the treatment and/or prevention of protozoal infections, especially malaria. Especially the following embodiments relating to the compounds of formula I are thus possible and intended and herewith specifically disclosed in individualized form:
1, 2+1, 3+1, 3+2+1, 4+1, 4+2+1, 4+3+1, 4+3+2+1, 5+1, 5+2+1, 5+3+1, 5+3+2+1, 5+4+1, 5+4+2+1, 5+4+3+1, 5+4+3+2+1, 6+1, 6+2+1, 6+3+1, 6+3+2+1, 6+4+1, 6+4+2+1, 6+4+3+1, 6+4+3+2+1, 7+1, 7+2+1, 7+3+1, 7+3+2+1, 7+4+1, 7+4+2+1, 7+4+3+1, 7+4+3+2+1, 7+5+1, 7+5+2+1, 7+5+3+1, 7+5+3+2+1, 7+5+4+1, 7+5+4+2+1, 7+5+4+3+1, 7+5+4+3+2+1, 7+6+1, 7+6+2+1, 7+6+3+1, 7+6+3+2+1, 7+6+4+1, 7+6+4+2+1, 7+6+4+3+1, 7+6+4+3+2+1, 8+1, 8+2+1, 8+3+1, 8+3+2+1, 8+4+1, 8+4+2+1, 8+4+3+1, 8+4+3+2+1, 8+5+1, 8+5+2+1, 8+5+3+1, 8+5+3+2+1, 8+5+4+1, 8+5+4+2+1, 8+5+4+3+1, 8+5+4+3+2+1, 8+6+1, 8+6+2+1, 8+6+3+1, 8+6+3+2+1, 8+6+4+1, 8+6+4+2+1, 8+6+4+3+1, 8+6+4+3+2+1, 8+7+1, 8+7+2+1, 8+7+3+1, 8+7+3+2+1, 8+7+4+1, 8+7+4+2+1, 8+7+4+3+1, 8+7+4+3+2+1, 8+7+5+1, 8+7+5+2+1, 8+7+5+3+1, 8+7+5+3+2+1, 8+7+5+4+1, 8+7+5+4+2+1, 8+7+5+4+3+1, 8+7+5+4+3+2+1, 8+7+6+1, 8+7+6+2+1, 8+7+6+3+1, 8+7+6+3+2+1, 8+7+6+4+1, 8+7+6+4+2+1, 8+7+6+4+3+1, 8+7+6+4+3+2+1, 9+1, 9+2+1, 9+3+1, 9+3+2+1, 9+4+1, 9+4+2+1, 9+4+3+1, 9+4+3+2+1, 9+5+1, 9+5+2+1, 9+5+3+1, 9+5+3+2+1, 9+5+4+1, 9+5+4+2+1, 9+5+4+3+1, 9+5+4+3+2+1, 9+6+1, 9+6+2+1, 9+6+3+1, 9+6+3+2+1, 9+6+4+1, 9+6+4+2+1, 9+6+4+3+1, 9+6+4+3+2+1, 9+7+1, 9+7+2+1, 9+7+3+1, 9+7+3+2+1, 9+7+4+1, 9+7+4+2+1, 9+7+4+3+1, 9+7+4+3+2+1, 9+7+5+1, 9+7+5+2+1, 9+7+5+3+1, 9+7+5+3+2+1, 9+7+5+4+1, 9+7+5+4+2+1, 9+7+5+4+3+1, 9+7+5+4+3+2+1, 9+7+6+1, 9+7+6+2+1, 9+7+6+3+1, 9+7+6+3+2+1, 9+7+6+4+1, 9+7+6+4+2+1, 9+7+6+4+3+1, 9+7+6+4+3+2+1, 10+1, 10+2+1, 10+3+1, 10+3+2+1, 10+4+1, 10+4+2+1, 10+4+3+1, 10+4+3+2+1, 10+5+1, 10+5+2+1, 10+5+3+1, 10+5+3+2+1, 10+5+4+1, 10+5+4+2+1, 10+5+4+3+1, 10+5+4+3+2+1, 10+6+1, 10+6+2+1, 10+6+3+1, 10+6+3+2+1, 10+6+4+1, 10+6+4+2+1, 10+6+4+3+1, 10+6+4+3+2+1, 11+1, 11+2+1, 11+3+1, 11+3+2+1, 11+4+1, 11+4+2+1, 11+4+3+1, 11+4+3+2+1, 11+5+1, 11+5+2+1, 11+5+3+1, 11+5+3+2+1, 11+5+4+1, 11+5+4+2+1, 11+5+4+3+1, 11+5+4+3+2+1, 11+6+1, 11+6+2+1, 11+6+3+1, 11+6+3+2+1, 11+6+4+1, 11+6+4+2+1, 11+6+4+3+1, 11+6+4+3+2+1.

In the list above, the numbers refer to the embodiments according to their numbering provided hereinabove whereas "+" indicates the dependency from another embodiment. The different individualized embodiments are separated by commas. In other words, "11+5+1" for example refers to embodiment 11), depending on embodiment 5), depending on embodiment 1), i.e. embodiment "11+5+1" corresponds to the compounds of embodiment 1) further limited by the features of the embodiments 5) and 11)).

13) Particular compounds according to embodiment 1) are selected from:
(E)-N-[4-(Methyl-pyridin-4-yl-amino)-benzyl]-N-piperidin-4-yl-3-(4-trifluoromethyl-phenyl)-acrylamide;
(E)-N-[4-(Methyl-pyridin-4-yl-amino)-benzyl]-N—(S)-piperidin-3-yl-3-(4-trifluoromethyl-phenyl)-acrylamide;
(E)-N-[4-(Methyl-pyridin-4-yl-amino)-benzyl]-N-[1-(4-trifluoromethyl-benzyl)-piperidin-4-yl]-3-(4-trifluoromethyl-phenyl)-acrylamide;
(E)-N-[1-(2-Methyl-oxazol-4-ylmethyl)-piperidin-4-yl]-N-[4-(methyl-pyridin-4-yl-amino)-benzyl]-3-(4-trifluoromethyl-phenyl)-acrylamide;
(E)-N-(1-Cyclopentyl-piperidin-4-yl)-N-[4-(methyl-pyridin-4-yl-amino)-benzyl]-3-(4-trifluoromethyl-phenyl)-acrylamide;
(E)-N-(1-Benzyl-piperidin-4-yl)-N-[4-(methyl-pyridin-4-yl-amino)-benzyl]-3-(4-trifluoromethyl-phenyl)-acrylamide;
(E)-N-(1-Ethyl-piperidin-4-yl)-N-[4-(methyl-pyridin-4-yl-amino)-benzyl]-3-(4-trifluoromethyl-phenyl)-acrylamide;
(E)-N-[1-(3-Methyl-butyl)-piperidin-4-yl]-N-[4-(methyl-pyridin-4-yl-amino)-benzyl]-3-(4-trifluoromethyl-phenyl)-acrylamide;
(E)-N-(1-Cyclopropylmethyl-piperidin-4-yl)-N-[4-(methyl-pyridin-4-yl-amino)-benzyl]-3-(4-trifluoromethyl-phenyl)-acrylamide;
(E)-N-(1'-Bicyclo[2.2.1]hept-5-en-2-ylmethyl-piperidin-4-yl)-N-[4-(methyl-pyridin-4-yl-amino)-benzyl]-3-(4-trifluoromethyl-phenyl)-acrylamide;
(E)-N-[1-(3,4-Dichloro-benzyl)-piperidin-4-yl]-N-[4-(methyl-pyridin-4-yl-amino)-benzyl]-3-(4-trifluoromethyl-phenyl)-acrylamide;
(E)-N-[1-(4-Methyl-benzyl)-piperidin-4-yl]-N-[4-(methyl-pyridin-4-yl-amino)-benzyl]-3-(4-trifluoromethyl-phenyl)-acrylamide;
(E)-N-[1-(4-Methoxy-benzyl)-piperidin-4-yl]-N-[4-(methyl-pyridin-4-yl-amino)-benzyl]-3-(4-trifluoromethyl-phenyl)-acrylamide;
(E)-N-[4-(Methyl-pyridin-4-yl-amino)-benzyl]-N-(1-phenethyl-piperidin-4-yl)-3-(4-trifluoromethyl-phenyl)-acrylamide;
(E)-N-[1-(2,2-Diphenyl-ethyl)-piperidin-4-yl]-N-[4-(methyl-pyridin-4-yl-amino)-benzyl]-3-(4-trifluoromethyl-phenyl)-acrylamide;
(E)-N-[4-(Methyl-pyridin-4-yl-amino)-benzyl]-3-(4-trifluoro-romethyl-phenyl)-N-[1-(3,3,3-trifluoro-propyl)-piperidin-4-yl]-acrylamide;
(E)-N-[1-(2-Methyl-2H-pyrazol-3-ylmethyl)-piperidin-4-yl]-N-[4-(methyl-pyridin-4-yl-amino)-benzyl]-3-(4-trifluoromethyl-phenyl)-acrylamide;

(E)-N-[4-(Methyl-pyridin-4-yl-amino)-benzyl]-N-[1-(1-phenyl-1H-pyrazol-4-ylmethyl)-piperidin-4-yl]-3-(4-trifluoromethyl-phenyl)-acrylamide;

(E)-N-[1-(3-Methyl-3H-imidazol-4-ylmethyl)-piperidin-4-yl]-N-[4-(methyl-pyridin-4-yl-amino)-benzyl]-3-(4-trifluoromethyl-phenyl)-acrylamide;

(E)-N-(1-Imidazo[1,5-a]pyridin-3-ylmethyl-piperidin-4-yl)-N-[4-(methyl-pyridin-4-yl-amino)-benzyl]-3-(4-trifluoromethyl-phenyl)-acrylamide;

(E)-N-[1-(1-Methyl-1H-benzoimidazol-2-ylmethyl)-piperidin-4-yl]-N-[4-(methyl-pyridin-4-yl-amino)-benzyl]-3-(4-trifluoromethyl-phenyl)-acrylamide;

(E)-N-[4-(Methyl-pyridin-4-yl-amino)-benzyl]-N-(1-pyridin-2-ylmethyl-piperidin-4-yl)-3-(4-trifluoromethyl-phenyl)-acrylamide;

(E)-N-[4-(Methyl-pyridin-4-yl-amino)-benzyl]-N-(1-pyridin-3-ylmethyl-piperidin-4-yl)-3-(4-trifluoromethyl-phenyl)-acrylamide;

(E)-N-[4-(Methyl-pyridin-4-yl-amino)-benzyl]-N-[1-(2-methyl-pyrimidin-5-ylmethyl)-piperidin-4-yl]-3-(4-trifluoromethyl-phenyl)-acrylamide;

(E)-N-(1-Imidazo[1,2-a]pyridin-7-ylmethyl-piperidin-4-yl)-N-[4-(methyl-pyridin-4-yl-amino)-benzyl]-3-(4-trifluoromethyl-phenyl)-acrylamide;

(E)-N-(1'-Methyl-[1,4']bipiperidinyl-4-yl)-N-[4-(methyl-pyridin-4-yl-amino)-benzyl]-3-(4-trifluoromethyl-phenyl)-acrylamide;

(E)-N-[1-(4-Cyano-benzyl)-piperidin-4-yl]-N-[4-(methyl-pyridin-4-yl-amino)-benzyl]-3-(4-trifluoromethyl-phenyl)-acrylamide;

(E)-N-[1-(1-Acetyl-1H-indol-3-ylmethyl)-piperidin-4-yl]-N-[4-(methyl-pyridin-4-yl-amino)-benzyl]-3-(4-trifluoromethyl-phenyl)-acrylamide;

(E)-N-[4-(Methyl-pyridin-4-yl-amino)-benzyl]-N-(1-pyrimidin-2-ylmethyl-piperidin-4-yl)-3-(4-trifluoromethyl-phenyl)-acrylamide;

(E)-N-[4-(Methyl-pyridin-4-yl-amino)-benzyl]-N-[1-(1-phenyl-ethyl)-piperidin-4-yl]-3-(4-trifluoromethyl-phenyl)-acrylamide;

(E)-N-(1-Cyclopropylmethyl-piperidin-4-yl)-N-[4-(2-methyl-pyridin-4-ylamino)-benzyl]-3-(4-trifluoromethyl-phenyl)-acrylamide;

(E)-N-[1-(2,5-Dimethyl-oxazol-4-ylmethyl)-piperidin-4-yl]-N-[4-(2-methyl-pyridin-4-ylamino)-benzyl]-3-(4-trifluoromethyl-phenyl)-acrylamide;

(E)-N-[4-(2-Methyl-pyridin-4-ylamino)-benzyl]-N-(1-propyl-piperidin-4-yl)-3-(4-trifluoromethyl-phenyl)-acrylamide;

(E)-N-[1-(5-Methyl-isoxazol-3-ylmethyl)-piperidin-4-yl]-N-[4-(2-methyl-pyridin-4-ylamino)-benzyl]-3-(4-trifluoromethyl-phenyl)-acrylamide;

(E)-N-[4-(2-Methyl-pyridin-4-ylamino)-benzyl]-N-[1-(4-methyl-thiazol-5-ylmethyl)-piperidin-4-yl]-3-(4-trifluoromethyl-phenyl)-acrylamide;

(E)-N-[1-(2-Methyl-oxazol-4-ylmethyl)-piperidin-4-yl]-N-[4-(2-methyl-pyridin-4-ylamino)-benzyl]-3-(4-trifluoromethyl-phenyl)-acrylamide;

(E)-N-(1-Benzyl-piperidin-4-yl)-N-[4-(2-methyl-pyridin-4-ylamino)-benzyl]-3-(4-trifluoromethyl-phenyl)-acrylamide;

(E)-N-(1-Imidazo[1,2-a]pyridin-3-ylmethyl-piperidin-4-yl)-N-[4-(2-methyl-pyridin-4-ylamino)-benzyl]-3-(4-trifluoromethyl-phenyl)-acrylamide;

(E)-N-[4-(2-Methyl-pyridin-4-ylamino)-benzyl]-3-(4-trifluoromethyl-phenyl)-N-[1-(3,3,3-trifluoro-propyl)-piperidin-4-yl]-acrylamide;

(E)-N-[4-(2-Methyl-pyridin-4-ylamino)-benzyl]-N-(1-thiazol-2-ylmethyl-piperidin-4-yl)-3-(4-trifluoromethyl-phenyl)-acrylamide;

(E)-N-[1-(1-Methyl-1H-imidazol-2-ylmethyl)-piperidin-4-yl]-N-[4-(2-methyl-pyridin-4-ylamino)-benzyl]-3-(4-trifluoromethyl-phenyl)-acrylamide;

(E)-N-[4-(2-Methyl-pyridin-4-ylamino)-benzyl]-N-[1-(4-methyl-thiazol-2-ylmethyl)-piperidin-4-yl]-3-(4-trifluoromethyl-phenyl)-acrylamide;

(E)-N-[1-(2,5-Dimethyl-2H-pyrazol-3-ylmethyl)-piperidin-4-yl]-N-[4-(2-methyl-pyridin-4-ylamino)-benzyl]-3-(4-trifluoromethyl-phenyl)-acrylamide;

(E)-N-[1-(3,5-Dimethyl-isoxazol-4-ylmethyl)-piperidin-4-yl]-N-[4-(2-methyl-pyridin-4-ylamino)-benzyl]-3-(4-trifluoromethyl-phenyl)-acrylamide;

(E)-N-(1-Imidazo[1,5-a]pyridin-1-ylmethyl-piperidin-4-yl)-N-[4-(2-methyl-pyridin-4-ylamino)-benzyl]-3-(4-trifluoromethyl-phenyl)-acrylamide;

(E)-N-(1-Imidazo[1,5-a]pyridin-3-ylmethyl-piperidin-4-yl)-N-[4-(2-methyl-pyridin-4-ylamino)-benzyl]-3-(4-trifluoromethyl-phenyl)-acrylamide;

(E)-N-[4-(2-Methyl-pyridin-4-ylamino)-benzyl]-N-(1-pyrimidin-2-ylmethyl-piperidin-4-yl)-3-(4-trifluoromethyl-phenyl)-acrylamide;

(E)-N-[4-(2-Methyl-pyridin-4-ylamino)-benzyl]-N-(1-pyridin-3-ylmethyl-piperidin-4-yl)-3-(4-trifluoromethyl-phenyl)-acrylamide;

(E)-N-[4-(2-Methyl-pyridin-4-ylamino)-benzyl]-N-(1-pyrimidin-5-ylmethyl-piperidin-4-yl)-3-(4-trifluoromethyl-phenyl)-acrylamide;

(E)-N-[1-(1-Methyl-1H-pyrazol-4-ylmethyl)-piperidin-4-yl]-N-[4-(2-methyl-pyridin-4-ylamino)-benzyl]-3-(4-trifluoromethyl-phenyl)-acrylamide;

(E)-N-[4-(2-Methyl-pyridin-4-ylamino)-benzyl]-N-[1-(2-methyl-pyrimidin-5-ylmethyl)-piperidin-4-yl]-3-(4-trifluoromethyl-phenyl)-acrylamide;

(E)-N-[1-(2,3-Dimethyl-3H-imidazol-4-ylmethyl)-piperidin-4-yl]-N-[4-(2-methyl-pyridin-4-ylamino)-benzyl]-3-(4-trifluoromethyl-phenyl)-acrylamide;

(E)-N-[1-(3-Dimethylaminomethyl-4-hydroxy-benzyl)-piperidin-4-yl]-N-[4-(2-methyl-pyridin-4-ylamino)-benzyl]-3-(4-trifluoromethyl-phenyl)-acrylamide;

(E)-N-[1-(3-Diethylaminomethyl-4-hydroxy-benzyl)-piperidin-4-yl]-N-[4-(2-methyl-pyridin-4-ylamino)-benzyl]-3-(4-trifluoromethyl-phenyl)-acrylamide;

(E)-N—((S)-1'-Methyl-[1,4']bipiperidinyl-3-yl)-N-[4-(methyl-pyridin-4-yl-amino)-benzyl]-3-(4-trifluoromethyl-phenyl)-acrylamide;

(E)-N—((R)-1'-Methyl-[1,4']bipiperidinyl-3-yl)-N-[4-(methyl-pyridin-4-yl-amino)-benzyl]-3-(4-trifluoromethyl-phenyl)-acrylamide;

(E)-N-[1-(1-Methyl-piperidin-4-yl)-azepan-4-yl]-N-[4-(methyl-pyridin-4-yl-amino)-benzyl]-3-(4-trifluoromethyl-phenyl)-acrylamide;

(E)-N—((S)-1-Cyclopentyl-piperidin-3-yl)-N-[4-(methyl-pyridin-4-yl-amino)-benzyl]-3-(4-trifluoromethyl-phenyl)-acrylamide;

(E)-N—((R)-1-Cyclopentyl-piperidin-3-yl)-N-[4-(methyl-pyridin-4-yl-amino)-benzyl]-3-(4-trifluoromethyl-phenyl)-acrylamide;

(E)-N-(1-Cyclopentyl-azepan-4-yl)-N-[4-(methyl-pyridin-4-yl-amino)-benzyl]-3-(4-trifluoromethyl-phenyl)-acrylamide;

(E)-N—((S)-1-(3-Methyl-butyl)-piperidin-3-yl)-N-[4-(methyl-pyridin-4-yl-amino)-benzyl]-3-(4-trifluoromethyl-phenyl)-acrylamide;

(E)-N—((R)-1-(3-Methyl-butyl)-piperidin-3-yl)-N-[4-(methyl-pyridin-4-yl-amino)-benzyl]-3-(4-trifluoromethyl-phenyl)-acrylamide;
(E)-N-[1-(3-Methyl-butyl)-azepan-4-yl]-N-[4-(methyl-pyridin-4-yl-amino)-benzyl]-3-(4-trifluoromethyl-phenyl)-acrylamide;
(E)-N-[(3aR,6aS)-2-(1-Methyl-piperidin-4-yl)-octahydro-cyclopenta[c]pyrrol-5-yl]-N-[4-(methyl-pyridin-4-yl-amino)-benzyl]-3-(4-trifluoromethyl-phenyl)-acrylamide;
(E)-N-[3-(1-Methyl-piperidin-4-yl)-3-aza-spiro[5.5]undec-9-yl]-N-[4-(methyl-pyridin-4-yl-amino)-benzyl]-3-(4-trifluoromethyl-phenyl)-acrylamide;
(E)-N-((3aR,6aS)-2-Cyclopentyl-octahydro-cyclopenta[c]pyrrol-5-yl)-N-[4-(methyl-pyridin-4-yl-amino)-benzyl]-3-(4-trifluoromethyl-phenyl)-acrylamide;
(E)-N-(3-Cyclopentyl-3-aza-spiro[5.5]undec-9-yl)-N-[4-(methyl-pyridin-4-yl-amino)-benzyl]-3-(4-trifluoromethyl-phenyl)-acrylamide;
(E)-N-[(3aR,6aS)-2-(3-Methyl-butyl)-octahydro-cyclopenta[c]pyrrol-5-yl]-N-[4-(methyl-pyridin-4-yl-amino)-benzyl]-3-(4-trifluoromethyl-phenyl)-acrylamide;
(E)-N-[3-(3-Methyl-butyl)-3-aza-spiro[5.5]undec-9-yl]-N-[4-(methyl-pyridin-4-yl-amino)-benzyl]-3-(4-trifluoromethyl-phenyl)-acrylamide;
(E)-N-[1-(1-Methyl-piperidin-4-yl)-azepan-3-yl]-N-[4-(methyl-pyridin-4-yl-amino)-benzyl]-3-(4-trifluoromethyl-phenyl)-acrylamide;
(E)-N-(1-Cyclopentyl-azepan-3-yl)-N-[4-(methyl-pyridin-4-yl-amino)-benzyl]-3-(4-trifluoromethyl-phenyl)-acrylamide;
(E)-N-[1-(3-Methyl-butyl)-azepan-3-yl]-N-[4-(methyl-pyridin-4-yl-amino)-benzyl]-3-(4-trifluoromethyl-phenyl)-acrylamide;
(E)-N-[2-(1-Methyl-piperidin-4-yl)-2-aza-spiro[3.3]hept-6-yl]-N-[4-(methyl-pyridin-4-yl-amino)-benzyl]-3-(4-trifluoromethyl-phenyl)-acrylamide;
(E)-N-(2-Cyclopentyl-2-aza-spiro[3.3]hept-6-yl)-N-[4-(methyl-pyridin-4-yl-amino)-benzyl]-3-(4-trifluoromethyl-phenyl)-acrylamide;
(E)-N-[2-(3-Methyl-butyl)-2-aza-spiro[3.3]hept-6-yl]-N-[4-(methyl-pyridin-4-yl-amino)-benzyl]-3-(4-trifluoromethyl-phenyl)-acrylamide;
(E)-N-((3R,4S)-1-Cyclopentyl-3-fluoro-piperidin-4-yl)-N-[4-(methyl-pyridin-4-yl-amino)-benzyl]-3-(4-trifluoromethyl-phenyl)-acrylamide;
(E)-N-[(3R,4S)-3-Fluoro-1-(3-methyl-butyl)-piperidin-4-yl]-N-[4-(methyl-pyridin-4-yl-amino)-benzyl]-3-(4-trifluoromethyl-phenyl)-acrylamide;
(E)-N-((3R,4S)-3-Fluoro-1'-methyl-[1,4']bipiperidinyl-4-yl)-N-[4-(methyl-pyridin-4-yl-amino)-benzyl]-3-(4-trifluoromethyl-phenyl)-acrylamide;
(E)-N-((3S,4S)-3-Fluoro-1'-methyl-[1,4']bipiperidinyl-4-yl)-N-[4-(methyl-pyridin-4-yl-amino)-benzyl]-3-(4-trifluoromethyl-phenyl)-acrylamide;
(E)-N-((3S,4S)-1-Cyclopentyl-3-fluoro-piperidin-4-yl)-N-[4-(methyl-pyridin-4-yl-amino)-benzyl]-3-(4-trifluoromethyl-phenyl)-acrylamide;
(E)-N-[(3S,4S)-3-Fluoro-1-(3-methyl-butyl)-piperidin-4-yl]-N-[4-(methyl-pyridin-4-yl-amino)-benzyl]-3-(4-trifluoromethyl-phenyl)-acrylamide;
(E)-N—((S)-1-Ethyl-piperidin-3-yl)-N-[4-(methyl-pyridin-4-yl-amino)-benzyl]-3-(4-trifluoromethyl-phenyl)-acrylamide;
(E)-N—((S)-1-Isopropyl-piperidin-3-yl)-N-[4-(methyl-pyridin-4-yl-amino)-benzyl]-3-(4-trifluoromethyl-phenyl)-acrylamide;
(E)-N-[1-(2-Methoxy-1-methyl-ethyl)-piperidin-4-yl]-N-[4-(2-methyl-pyridin-4-ylamino)-benzyl]-3-(4-trifluoromethyl-phenyl)-acrylamide;
(E)-N-(1-Cyclopentyl-piperidin-4-yl)-N-[4-(2-methyl-quinolin-4-ylamino)-benzyl]-3-(4-trifluoromethyl-phenyl)-acrylamide;
(E)-N-(1-Cyclopentyl-piperidin-4-yl)-N-[4-(pyridin-4-ylamino)-benzyl]-3-(4-trifluoromethyl-phenyl)-acrylamide;
(E)-N-(1-Cyclopentyl-piperidin-4-yl)-N-[4-(2,6-dimethyl-pyridin-4-ylamino)-benzyl]-3-(4-trifluoromethyl-phenyl)-acrylamide;
(E)-N-(1-Cyclopentyl-piperidin-4-yl)-N-[4-(6-methoxy-quinolin-4-ylamino)-benzyl]-3-(4-trifluoromethyl-phenyl)-acrylamide;
(E)-N-[4-(2,8-Bis-trifluoromethyl-quinolin-4-ylamino)-benzyl]-N-(1-cyclopentyl-piperidin-4-yl)-3-(4-trifluoromethyl-phenyl)-acrylamide;
(E)-N-(1-Cyclopentyl-piperidin-4-yl)-3-(4-trifluoromethyl-phenyl)-N-[4-(7-trifluoromethyl-quinolin-4-ylamino)-benzyl]-acrylamide;
(E)-N-(1-Cyclopentyl-piperidin-4-yl)-N-[4-(pyrimidin-5-ylamino)-benzyl]-3-(4-trifluoromethyl-phenyl)-acrylamide;
(E)-N-(1-Cyclopentyl-piperidin-4-yl)-N-[4-(pyrimidin-4-ylamino)-benzyl]-3-(4-trifluoromethyl-phenyl)-acrylamide;
(E)-N-(1-Cyclopentyl-piperidin-4-yl)-N-(4-phenylamino-benzyl)-3-(4-trifluoromethyl-phenyl)-acrylamide;
(E)-N-(1-Cyclopentyl-piperidin-4-yl)-N-[4-(2-methoxy-pyridin-4-ylamino)-benzyl]-3-(4-trifluoromethyl-phenyl)-acrylamide;
(E)-N-(1-Cyclopentyl-piperidin-4-yl)-N-[4-(2-methyl-pyridin-4-ylamino)-benzyl]-3-(4-trifluoromethyl-phenyl)-acrylamide;
(E)-N-(1-Cyclopentyl-piperidin-4-yl)-N-[4-(methyl-pyridin-3-yl-amino)-benzyl]-3-(4-trifluoromethyl-phenyl)-acrylamide;
(E)-N-[4-(7-Chloro-quinolin-4-ylamino)-benzyl]-N-(1-cyclopentyl-piperidin-4-yl)-3-(4-trifluoromethyl-phenyl)-acrylamide;
(E)-N-(1-Cyclopentyl-piperidin-4-yl)-N-[4-(5-methyl-pyridin-2-ylamino)-benzyl]-3-(4-trifluoromethyl-phenyl)-acrylamide;
(E)-N-(1-Cyclopentyl-pyrrolidin-3-yl)-N-[4-(methyl-pyridin-4-yl-amino)-benzyl]-3-(4-trifluoromethyl-phenyl)-acrylamide;
(E)-N-(1-Cyclopentyl-piperidin-4-yl)-N-[4-(6-methoxy-2-methyl-quinolin-4-ylamino)-benzyl]-3-(4-trifluoromethyl-phenyl)-acrylamide;
(E)-N-(1-Cyclopentyl-pyrrolidin-3-yl)-N-[4-(2-methyl-pyridin-4-ylamino)-benzyl]-3-(4-trifluoromethyl-phenyl)-acrylamide;
(E)-N-(1-Cyclopentyl-azetidin-3-yl)-N-[4-(methyl-pyridin-4-yl-amino)-benzyl]-3-(4-trifluoromethyl-phenyl)-acrylamide;
(E)-N-(1-Cyclopentyl-piperidin-4-yl)-N-[6-(pyridin-4-ylamino)-pyridin-3-ylmethyl]-3-(4-trifluoromethyl-phenyl)-acrylamide;
(E)-N-(1-Cyclopentyl-piperidin-4-yl)-N-[6-(methyl-pyridin-4-yl-amino)-pyridin-3-ylmethyl]-3-(4-trifluoromethyl-phenyl)-acrylamide;
(E)-N-(1-Cyclopentyl-piperidin-4-yl)-N-[6-(1-methyl-piperidin-4-ylamino)-pyridin-3-ylmethyl]-3-(4-trifluoromethyl-phenyl)-acrylamide;

(E)-N-(1-Cyclopentyl-piperidin-4-yl)-N-{6-[methyl-(1-methyl-piperidin-4-yl)-amino]-pyridin-3-ylmethyl}-3-(4-trifluoromethyl-phenyl)-acrylamide;
(E)-N-(1-Cyclopentyl-piperidin-4-yl)-N-[6-(pyrimidin-4-ylamino)-pyridin-3-ylmethyl]-3-(4-trifluoromethyl-phenyl)-acrylamide;
(E)-N-(1-Cyclopentyl-piperidin-4-yl)-N-[6-(2-methyl-pyrimidin-4-ylamino)-pyridin-3-ylmethyl]-3-(4-trifluoromethyl-phenyl)-acrylamide;
(E)-N-(1-Cyclopentyl-piperidin-4-yl)-N-[6-(6-methyl-pyrimidin-4-ylamino)-pyridin-3-ylmethyl]-3-(4-trifluoromethyl-phenyl)-acrylamide;
(E)-N-(1'-Methyl-[1,4']bipiperidinyl-4-yl)-N-[6-(pyridin-4-ylamino)-pyridin-3-ylmethyl]-3-(4-trifluoromethyl-phenyl)-acrylamide;
(E)-N-(1'-Methyl-[1,4']bipiperidinyl-4-yl)-N-[6-(2-methyl-pyridin-4-ylamino)-pyridin-3-ylmethyl]-3-(4-trifluoromethyl-phenyl)-acrylamide;
(E)-N-(1'-Methyl-[1,4']bipiperidinyl-4-yl)-N-[6-(methyl-pyridin-4-yl-amino)-pyridin-3-ylmethyl]-3-(4-trifluoromethyl-phenyl)-acrylamide;
(E)-N—((R)-1-Cyclopentyl-pyrrolidin-3-yl)-N-[4-(methyl-pyridin-4-yl-amino)-benzyl]-3-(4-trifluoromethyl-phenyl)-acrylamide;
(E)-N—((S)-1-Cyclopentyl-pyrrolidin-3-yl)-N-[4-(methyl-pyridin-4-yl-amino)-benzyl]-3-(4-trifluoromethyl-phenyl)-acrylamide;
(E)-N-(1'-Methyl-[1,4']bipiperidinyl-4-yl)-N-[4-(pyridin-4-ylamino)-benzyl]-3-(4-trifluoromethyl-phenyl)-acrylamide;
(E)-N-(1'-Methyl-[1,4']bipiperidinyl-4-yl)-N-[4-(2-methyl-pyridin-4-ylamino)-benzyl]-3-(4-trifluoromethyl-phenyl)-acrylamide;
(E)-3-(4-Chloro-phenyl)-N-(1'-methyl-[1,4']bipiperidinyl-4-yl)-N-[4-(2-methyl-pyridin-4-ylamino)-benzyl]-acrylamide;
(E)-N-(1'-Methyl-[1,4']bipiperidinyl-4-yl)-N-[4-(pyridin-4-ylamino)-benzyl]-3-(4-trifluoromethoxy-phenyl)-acrylamide;
(E)-N-(1'-Methyl-[1,4']bipiperidinyl-4-yl)-N-[4-(2-methyl-pyridin-4-ylamino)-benzyl]-3-(4-trifluoromethoxy-phenyl)-acrylamide;
(E)-N—((S)-1-Isopropyl-piperidin-3-yl)-N-[6-(2-methyl-pyridin-4-ylamino)-pyridin-3-ylmethyl]-3-(4-trifluoromethyl-phenyl)-acrylamide;
(E)-N-(1-Isopropyl-piperidin-4-yl)-N-{3-[methyl-(2-methyl-pyridin-4-yl)-amino]benzyl}-3-(4-trifluoromethyl-phenyl)-acrylamide;
(E)-N-(1-Isopropyl-piperidin-4-yl)-N-[3-(2-methyl-pyridin-4-ylamino)-benzyl]-3-(4-trifluoromethyl-phenyl)-acrylamide;
(E)-N-(1-Isopropyl-piperidin-4-yl)-N-[3-(3-methyl-pyridin-4-ylamino)-benzyl]-3-(4-trifluoromethyl-phenyl)-acrylamide;
(E)-N-[3-(3-Fluoro-pyridin-4-ylamino)-benzyl]-N-(1-isopropyl-piperidin-4-yl)-3-(4-trifluoromethyl-phenyl)-acrylamide;
(E)-N-(1-Isopropyl-piperidin-4-yl)-N-[3-(pyrimidin-4-ylamino)-benzyl]-3-(4-trifluoromethyl-phenyl)-acrylamide;
(E)-N-(1-Isopropyl-piperidin-4-yl)-N-[3-(pyridin-4-ylamino)-benzyl]-3-(4-trifluoromethyl-phenyl)-acrylamide;
(E)-N-(1-Isopropyl-piperidin-4-yl)-N-[6-(methyl-pyridin-4-yl-amino)-pyridin-2-ylmethyl]-3-(4-trifluoromethyl-phenyl)-acrylamide;
(E)-N-(1-Isopropyl-piperidin-4-yl)-N-{6-[methyl-(2-methyl-pyridin-4-yl)-amino]-pyridin-2-ylmethyl}-3-(4-trifluoromethyl-phenyl)-acrylamide;
(E)-N-(1-Isopropyl-piperidin-4-yl)-N-[6-(2-methyl-pyridin-4-ylamino)-pyridin-2-ylmethyl]-3-(4-trifluoromethyl-phenyl)-acrylamide;
(E)-N-(1-Isopropyl-piperidin-4-yl)-N-[6-(3-methyl-pyridin-4-ylamino)-pyridin-2-ylmethyl]-3-(4-trifluoromethyl-phenyl)-acrylamide;
(E)-N-[6-(3-Fluoro-pyridin-4-ylamino)-pyridin-2-ylmethyl]-N-(1-isopropyl-piperidin-4-yl)-3-(4-trifluoromethyl-phenyl)-acrylamide;
(E)-N-(1-Isopropyl-piperidin-4-yl)-N-[6-(pyridin-4-ylamino)-pyridin-2-ylmethyl]-3-(4-trifluoromethyl-phenyl)-acrylamide;
(E)-N-(1-Isopropyl-piperidin-4-yl)-N-[5-(methyl-pyridin-4-yl-amino)-pyridin-3-ylmethyl]-3-(4-trifluoromethyl-phenyl)-acrylamide;
(E)-N-(1-Isopropyl-piperidin-4-yl)-N-[5-(methyl-pyridin-3-yl-amino)-pyridin-3-ylmethyl]-3-(4-trifluoromethyl-phenyl)-acrylamide;
(E)-N-(1-Isopropyl-piperidin-4-yl)-N-{5-[methyl-(2-methyl-pyridin-4-yl)-amino]-pyridin-3-ylmethyl}-3-(4-trifluoromethyl-phenyl)-acrylamide;
(E)-N-(1-Isopropyl-piperidin-4-yl)-N-[5-(2-methyl-pyridin-4-ylamino)-pyridin-3-ylmethyl]-3-(4-trifluoromethyl-phenyl)-acrylamide;
(E)-N-(1-Isopropyl-piperidin-4-yl)-N-[5-(3-methyl-pyridin-4-ylamino)-pyridin-3-ylmethyl]-3-(4-trifluoromethyl-phenyl)-acrylamide;
(E)-N-[5-(3-Fluoro-pyridin-4-ylamino)-pyridin-3-ylmethyl]-N-(1-isopropyl-piperidin-4-yl)-3-(4-trifluoromethyl-phenyl)-acrylamide;
(E)-N-(1-Isopropyl-piperidin-4-yl)-N-[5-(pyrimidin-4-ylamino)-pyridin-3-ylmethyl]-3-(4-trifluoromethyl-phenyl)-acrylamide;
(E)-N-(1-Isopropyl-piperidin-4-yl)-N-[5-(methyl-pyridin-2-yl-amino)-pyridin-3-ylmethyl]-3-(4-trifluoromethyl-phenyl)-acrylamide;
(E)-N-(1-Isopropyl-piperidin-4-yl)-N-[5-(pyridin-4-ylamino)-pyridin-3-ylmethyl]-3-(4-trifluoromethyl-phenyl)-acrylamide;
(E)-N-(1-Isopropyl-piperidin-4-yl)-N-[3-(methyl-pyridin-4-yl-amino)-benzyl]-3-(4-trifluoromethyl-phenyl)-acrylamide;
(E)-N-(1-Benzyl-piperidin-4-yl)-3-(4-isopropoxy-phenyl)-N-[4-(methyl-pyridin-4-yl-amino)-benzyl]-acrylamide;
(E)-N-(1-Benzyl-piperidin-4-yl)-3-(4-tert-butyl-phenyl)-N-[4-(methyl-pyridin-4-yl-amino)-benzyl]-acrylamide;
(E)-N-(1-Benzyl-piperidin-4-yl)-3-(4-difluoromethoxy-phenyl)-N-[4-(methyl-pyridin-4-yl-amino)-benzyl]-acrylamide;
(E)-N-(1-Benzyl-piperidin-4-yl)-N-[4-(methyl-pyridin-4-yl-amino)-benzyl]-3-(4-trifluoromethoxy-phenyl)-acrylamide;
(E)-N-(1-Benzyl-piperidin-4-yl)-3-(4-ethyl-phenyl)-N-[4-(methyl-pyridin-4-yl-amino)-benzyl]-acrylamide;
(E)-N-(1-Benzyl-piperidin-4-yl)-N-[4-(methyl-pyridin-4-yl-amino)-benzyl]-3-(4-propoxy-phenyl)-acrylamide;
(E)-N-(1-Benzyl-piperidin-4-yl)-3-(4-methoxy-phenyl)-N-[4-(methyl-pyridin-4-yl-amino)-benzyl]-acrylamide;
(E)-N-(1-Benzyl-piperidin-4-yl)-3-(3-methoxy-phenyl)-N-[4-(methyl-pyridin-4-yl-amino)-benzyl]-acrylamide;
(E)-N-(1-Benzyl-piperidin-4-yl)-3-(2-methoxy-phenyl)-N-[4-(methyl-pyridin-4-yl-amino)-benzyl]-acrylamide;
(E)-N-(1-Benzyl-piperidin-4-yl)-3-(4-chloro-phenyl)-N-[4-(methyl-pyridin-4-yl-amino)-benzyl]-acrylamide;

(E)-N-(1-Benzyl-piperidin-4-yl)-3-(3-chloro-phenyl)-N-[4-(methyl-pyridin-4-yl-amino)-benzyl]-acrylamide;
(E)-N-(1-Benzyl-piperidin-4-yl)-3-(2-chloro-phenyl)-N-[4-(methyl-pyridin-4-yl-amino)-benzyl]-acrylamide;
(E)-N-(1-Benzyl-piperidin-4-yl)-3-(4-fluoro-phenyl)-N-[4-(methyl-pyridin-4-yl-amino)-benzyl]-acrylamide;
(E)-N-(1-Benzyl-piperidin-4-yl)-3-(3-fluoro-phenyl)-N-[4-(methyl-pyridin-4-yl-amino)-benzyl]-acrylamide;
(E)-N-(1-Benzyl-piperidin-4-yl)-3-(2-fluoro-phenyl)-N-[4-(methyl-pyridin-4-yl-amino)-benzyl]-acrylamide;
(E)-N-(1-Benzyl-piperidin-4-yl)-N-[4-(methyl-pyridin-4-yl-amino)-benzyl]-3-p-tolyl-acrylamide;
(E)-N-(1-Benzyl-piperidin-4-yl)-N-[4-(methyl-pyridin-4-yl-amino)-benzyl]-3-m-tolyl-acrylamide;
(E)-N-(1-Benzyl-piperidin-4-yl)-N-[4-(methyl-pyridin-4-yl-amino)-benzyl]-3-o-tolyl-acrylamide;
(E)-N-(1-Benzyl-piperidin-4-yl)-N-[4-(methyl-pyridin-4-yl-amino)-benzyl]-3-(6-trifluoromethyl-pyridin-3-yl)-acrylamide;
(E)-N-(1-Benzyl-piperidin-4-yl)-3-(4-methanesulfonyl-phenyl)-N-[4-(methyl-pyridin-4-yl-amino)-benzyl]-acrylamide;
(E)-N-(1-Benzyl-piperidin-4-yl)-3-(2,4-dimethyl-thiazol-5-yl)-N-[4-(methyl-pyridin-4-yl-amino)-benzyl]-acrylamide;
(E)-N-(1-Benzyl-piperidin-4-yl)-3-(1,5-dimethyl-1H-pyrazol-4-yl)-N-[4-(methyl-pyridin-4-yl-amino)-benzyl]-acrylamide;
(E)-N-(1-Benzyl-piperidin-4-yl)-N-[4-(methyl-pyridin-4-yl-amino)-benzyl]-3-(1,3,5-trimethyl-1H-pyrazol-4-yl)-acrylamide;
(E)-N-(3-Dimethylamino-propyl)-N-[4-(2-methyl-pyridin-4-ylamino)-benzyl]-3-(4-trifluoromethyl-phenyl)-acrylamide;
(E)-3-(4-Chloro-phenyl)-N-(3-dimethylamino-propyl)-N-[4-(2-methyl-pyridin-4-ylamino)-benzyl]-acrylamide;
(E)-N-(1-Cyclopentyl-piperidin-4-yl)-N-[6-(2-methyl-pyridin-4-ylamino)-pyridin-3-ylmethyl]-3-(4-trifluoromethyl-phenyl)-acrylamide;
(E)-3-(4-Chloro-phenyl)-N-(1-cyclopentyl-piperidin-4-yl)-N-[6-(2-methyl-pyridin-4-ylamino)-pyridin-3-ylmethyl]-acrylamide;
(E)-N-(1-Cyclopentyl-piperidin-4-yl)-N-[5-(2-methyl-pyridin-4-ylamino)-pyridin-2-ylmethyl]-3-(4-trifluoromethyl-phenyl)-acrylamide;
(E)-3-(4-Chloro-phenyl)-N-(1-cyclopentyl-piperidin-4-yl)-N-[5-(2-methyl-pyridin-4-ylamino)-pyridin-2-ylmethyl]-acrylamide;
(E)-N-(1'-Methyl-[1,4']bipiperidinyl-4-ylmethyl)-N-[4-(2-methyl-pyridin-4-ylamino)-benzyl]-3-(4-trifluoromethyl-phenyl)-acrylamide;
(E)-N-[4-(2-Methyl-pyridin-4-ylamino)-benzyl]-N-(3-morpholin-4-yl-propyl)-3-(4-trifluoromethyl-phenyl)-acrylamide;
(E)-N-(1-Methyl-piperidin-4-yl)-N-[4-(2-methyl-pyridin-4-ylamino)-benzyl]-3-(4-trifluoromethyl-phenyl)-acrylamide;
(E)-N-(4-Hydroxy-1-methyl-piperidin-4-ylmethyl)-N-[4-(2-methyl-pyridin-4-ylamino)-benzyl]-3-(4-trifluoromethyl-phenyl)-acrylamide;
(E)-N-(2-Dimethylamino-ethyl)-N-[4-(2-methyl-pyridin-4-ylamino)-benzyl]-3-(4-trifluoromethyl-phenyl)-acrylamide;
(E)-N-(1-Benzyl-piperidin-4-yl)-N-{4-[methyl-(1-methyl-piperidin-4-yl)-amino]-benzyl}-3-(4-trifluoromethyl-phenyl)-acrylamide;
(E)-N-(1-Benzyl-piperidin-4-yl)-N-{4-[methyl-(1-methyl-piperidin-4-yl)-amino]-benzyl}-3-(4-trifluoromethoxy-phenyl)-acrylamide;
(E)-3-(4-Cyano-phenyl)-N-(1'-methyl-[1,4']bipiperidinyl-4-yl)-N-[4-(methyl-pyridin-4-yl-amino)-benzyl]-acrylamide;
(E)-3-(4-Chloro-phenyl)-N-(1'-methyl-[1,4']bipiperidinyl-4-yl)-N-[4-(methyl-pyridin-4-yl-amino)-benzyl]-acrylamide;
(E)-3-(4-Difluoromethoxy-phenyl)-N-(1'-methyl-[1,4']bipiperidinyl-4-yl)-N-[4-(methyl-pyridin-4-yl-amino)-benzyl]-acrylamide;
(E)-N-(1'-Methyl-[1,4']bipiperidinyl-4-yl)-N-[4-(methyl-pyridin-4-yl-amino)-benzyl]-3-phenyl-acrylamide;
(E)-N-(1'-Methyl-[1,4']bipiperidinyl-4-yl)-N-[4-(methyl-pyridin-4-yl-amino)-benzyl]-3-(6-trifluoromethyl-pyridin-3-yl)-acrylamide;
(E)-N-(1-Cyclopentyl-piperidin-4-yl)-N-{4-[methyl-(2-methyl-pyridin-4-yl)-amino]-benzyl}-3-(4-trifluoromethyl-phenyl)-acrylamide;
(E)-N-[4-(3-Diethylaminomethyl-4-hydroxy-phenylamino)-benzyl]-N-(1-methyl-piperidin-4-yl)-3-(4-trifluoromethyl-phenyl)-acrylamide;
(E)-N-(1-Isopropyl-piperidin-4-yl)-N-[4-(2-methyl-pyridin-4-ylamino)-benzyl]-3-(4-trifluoromethyl-phenyl)-acrylamide;
(E)-N-(1'-Methyl-[1,4']bipiperidinyl-4-ylmethyl)-N-[4-(methyl-pyridin-4-yl-amino)-benzyl]-3-(4-trifluoromethyl-phenyl)-acrylamide;
(E)-N-(1-Cyclopentyl-piperidin-4-ylmethyl)-N-[4-(methyl-pyridin-4-yl-amino)-benzyl]-3-(4-trifluoromethyl-phenyl)-acrylamide;
(E)-N-[1-(3-Methyl-butyl)-piperidin-4-ylmethyl]-N-[4-(methyl-pyridin-4-yl-amino)-benzyl]-3-(4-trifluoromethyl-phenyl)-acrylamide;
(E)-N-(4-Dimethylamino-cyclohexyl)-N-[4-(methyl-pyridin-4-yl-amino)-benzyl]-3-(4-trifluoromethyl-phenyl)-acrylamide;
(E)-N-(4-Dimethylamino-cyclohexyl)-N-[4-(methyl-pyridin-4-yl-amino)-benzyl]-3-(4-trifluoromethyl-phenyl)-acrylamide;
(E)-N-[4-(Methyl-pyridin-4-yl-amino)-benzyl]-N-(4-pyrrolidin-1-yl-cyclohexyl)-3-(4-trifluoromethyl-phenyl)-acrylamide;
(E)-N-[4-(Methyl-pyridin-4-yl-amino)-benzyl]-N-(4-pyrrolidin-1-yl-cyclohexyl)-3-(4-trifluoromethyl-phenyl)-acrylamide;
(E)-N-(1'-Methyl-[1,4']bipiperidinyl-4-yl)-N-[4-(pyridine-4-carbonyl)-benzyl]-3-(4-trifluoromethyl-phenyl)-acrylamide;
(E)-N-[1-(2-Dimethylamino-ethyl)-piperidin-4-yl]-N-[4-(methyl-pyridin-4-yl-amino)-benzyl]-3-(4-trifluoromethyl-phenyl)-acrylamide;
(E)-N-(1-Cyclopentyl-piperidin-4-yl)-N-[4-(2-methyl-pyridin-4-yl)-benzyl]-3-(4-trifluoromethyl-phenyl)-acrylamide;
(E)-N-(1-Cyclopentyl-piperidin-4-yl)-N-(4-pyridin-3-yl-benzyl)-3-(4-trifluoromethyl-phenyl)-acrylamide;
(E)-N-(1-Cyclopentyl-piperidin-4-yl)-N-(4-pyridin-2-yl-benzyl)-3-(4-trifluoromethyl-phenyl)-acrylamide;
(E)-N-(1-Cyclopentyl-piperidin-4-yl)-N-[4-(4-isopropyl-piperazin-1-yl)-benzyl]-3-(4-trifluoromethyl-phenyl)-acrylamide;
(E)-N-(1-Cyclopentyl-piperidin-4-yl)-N-[4-(4-methyl-piperazin-1-yl)-benzyl]-3-(4-trifluoromethyl-phenyl)-acrylamide;

(E)-N-(1-Cyclopentyl-piperidin-4-yl)-N-[4-(2-methyl-thiazol-5-yl)-benzyl]-3-(4-trifluoromethyl-phenyl)-acrylamide;

(E)-N-(1-Cyclopentyl-piperidin-4-yl)-N-[4-(1-methyl-1H-pyrazol-3-yl)-benzyl]-3-(4-trifluoromethyl-phenyl)-acrylamide;

(E)-N-(1-Cyclopentyl-piperidin-4-yl)-N-(4-pyrimidin-2-yl-benzyl)-3-(4-trifluoromethyl-phenyl)-acrylamide;

(E)-N-(1-Cyclopentyl-piperidin-4-yl)-N-(4-pyrimidin-5-yl-benzyl)-3-(4-trifluoromethyl-phenyl)-acrylamide;

(E)-N-(1-Cyclopentyl-piperidin-4-yl)-N-[4-(3-dimethyl-amino-propoxy)-benzyl]-3-(4-trifluoromethyl-phenyl)-acrylamide;

(E)-N-(1-Cyclopentyl-piperidin-4-yl)-N-(2-pyrrolidin-1-yl-pyridin-4-ylmethyl)-3-(4-trifluoromethyl-phenyl)-acrylamide;

(E)-N-(1-Cyclopentyl-piperidin-4-yl)-N-[4-(pyridin-4-yloxy)-benzyl]-3-(4-trifluoromethyl-phenyl)-acrylamide;

(E)-N-(1-Cyclopentyl-piperidin-4-yl)-N-[4-(2,6-dimethyl-pyridin-4-yloxy)-benzyl]-3-(4-trifluoromethyl-phenyl)-acrylamide;

(E)-3-(4-Chloro-phenyl)-N-(2-dimethylamino-1-methyl-ethyl)-N-[4-(2-methyl-pyridin-4-ylamino)-benzyl]-acrylamide; and (E)-3-(4-Chloro-phenyl)-N-(1-cyclopropyl-piperidin-4-yl)-N-[4-(2-methyl-pyridin-4-ylamino)-benzyl]-acrylamide.

The compounds of formula I and II according to any one of embodiments 1) to 13), and their pharmaceutically acceptable salts can be used as medicaments, e.g. in the form of pharmaceutical compositions for enteral (such especially oral) or parenteral (including topical application or inhalation) administration, and are suitable for the treatment and/or prevention of the diseases mentioned herein, such as malaria infections, or other protozoal diseases like sleeping sickness, Chagas disease, amebiasis, giardiasis, trichomoniasis, toxoplasmosis, and leishmaniasis; especially malaria.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, pharmaceutically acceptable solid or liquid carrier materials and, if desired, usual pharmaceutical adjuvants.

In one embodiment, the invention relates to a method for the treatment or prevention of the diseases mentioned herein, such as especially malaria, said method comprising administering to a subject a pharmaceutically active amount of a compound of formula I.

In a preferred embodiment of the invention, the administered amount of a compound according to any one of embodiments 1) to 13) is comprised between 1 mg and 1000 mg per day, particularly between 5 mg and 500 mg per day, more particularly between 25 mg and 400 mg per day, especially between 50 mg and 200 mg per day.

For avoidance of any doubt, if compounds are described as useful for the prevention or treatment of certain diseases, such compounds are likewise suitable for use in the preparation of a medicament for the prevention or treatment of the diseases mentioned herein, such as especially malaria.

The compounds of formula I according to any one of embodiments 1) to 13), or the above-mentioned pharmaceutical compositions, may also be used in combination with one or more other therapeutically useful substances e.g. with other antimalarials like quinolines (e.g. quinine, chloroquine, amodiaquine, mefloquine, primaquine, and tafenoquine), peroxide antimalarials (e.g. artemisinin, artemether, and artesunate), pyrimethamine-sulfadoxine antimalarials (e.g. Fansidar®), hydroxynaphtoquinones (e.g. atovaquone), acroline-type antimalarials (e.g. pyronaridine), or other antiprotozoal agents like ethylstibamine, hydroxystilbamidine, pentamidine, stilbamidine, quinapyramine, puromycine, propamidine, nifurtimox, melarsoprol, nimorazole, nifuroxime, aminitrozole and the like.

The present invention also relates to the use of a compound of formula I according to any one of embodiments 1) to 13), or a pharmaceutically acceptable salt thereof, for the preparation of a pharmaceutical composition, optionally for use in combination with one or more other therapeutically useful substances such as those mentioned in the preceding paragraph, for the prevention and/or treatment of the diseases mentioned herein, such as especially malaria.

Preparation of Compounds of Formula I

Compounds of formula I can be manufactured by the methods given below, by the methods given in the examples or by analogous methods. Optimum reaction conditions may vary with the particular reactants or solvents used, but such conditions can be determined by a person skilled in the art by routine optimization procedures. Compounds of formula I of the present invention can be prepared according to the general sequence of reactions outlined below wherein, if not explicitly stated otherwise, $R^1$ to $R^{17}$, X, and A are as defined for formula I.

Compounds of formula I can be prepared according to the synthetic pathway described in Scheme 1. Thus an intermediate of Structure 1 is condensed with a commercially available or well known carboxylic acid 2 in the presence of a coupling reagent, such as EDC, TBTU, diisopropylcarbodiimide, HATU, DCC, Ghosez's reagent or the like, in the presence of a base like $NEt_3$, DIPEA, or pyridine to form a compound of formula I. An intermediate of Structure 1 is prepared by a reductive amination between an aldehyde 3 and an amine 4 in the presence of a reducing agent like $NaBH_4$, or $NaBH(OAc)_3$. If the amine 4 is a salt, like an hydrochloride salt, a base like $NEt_3$ or DIPEA is added during the reductive amination.

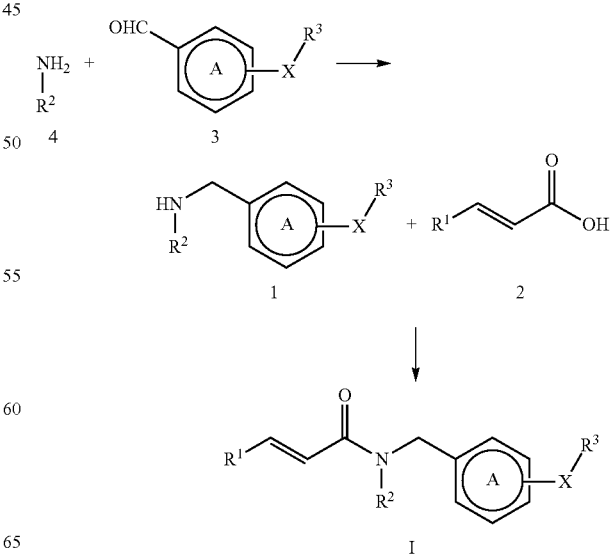

Scheme 1. Synthesis of a compound of formula I.

Alternatively, a compound of formula I is synthesized following the sequence depicted in Scheme 2. A compound of formula I is obtained by a Buchwald-Hartwig cross-coupling between a bromide of Structure 5 and an amine 6 (wherein for example ring A represents phenylene or pyridin-diyl and X represents $NR^4$) in the presence of palladium catalyst like $Pd_2(dba)_3$, a ligand like X-phos, a base like NaOtBu and a solvent like dioxane. A reductive amination between an amine 4 and an aldehyde 7 in the presence of a reducing agent like $NaBH_4$ or $NaBH(OAc)_3$ affords an amine 8. If the amine 4 is a salt, like an hydrochloride salt, a base like $NEt_3$ or DIPEA is added during the reductive amination. An amine 8 is condensed with a commercially available or well known carboxylic acid 2 in the presence of a coupling reagent, such as EDC, TBTU, diisopropylcarbodiimide, HATU, DCC, Ghosez's reagent or the like, in the presence of a base like $NEt_3$, DIPEA, or pyridine to form a compound of Structure 5.

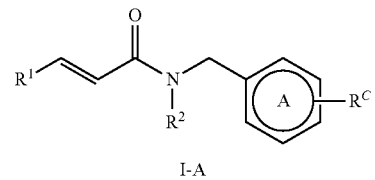

I-A

In a further aspect, a compound of formula I can be obtained through a reductive amination between an amine of Structure 10 and an appropriate aldehyde or ketone 11 in the presence of a reducing agent like $NaHB(OAc)_3$ (Scheme 4). If 11 is a ketone, activation with a Lewis acid or AcOH may be required. An intermediate of Structure 10 is obtained after removal of a protecting group (PG) from an intermediate 12, applying reaction conditions known to a skilled person. Preferably, PG is a group such as tert-butoxycarbonyl. A tert-butoxycarbonyl group is cleaved under acidic conditions. A compound 12 is obtained by condensation between an amine 13 and a commercially available or well known carboxylic acid 2 in the presence of a coupling reagent, such as EDC, TBTU, diisopropylcarbodiimide, HATU, DCC, Ghosez's reagent or the like, in the presence of a base like $NEt_3$, DIPEA, or pyridine. A reductive amination between an amine 14 (wherein L represents $(C_{0-2})$alkyl) and an aldehyde 3 in the presence of a reducing agent like $NaBH_4$ or $NaBH(OAc)_3$ affords an amine 13. If the amine 14 is a salt, like an hydrochloride salt, a base like $NEt_3$ or DIPEA is added during the reductive amination.

Scheme 2. Synthesis of compound of formula I.

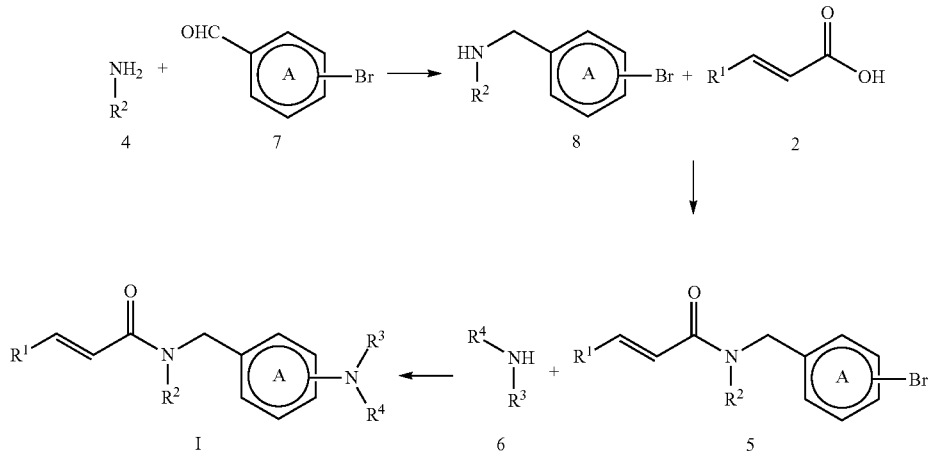

In another aspect, a bromide of Structure 5 can be engaged in a Suzuki cross-coupling with an appropriate boronic acid or a boronic ester derivative 9 (wherein $R^B$ represents hydrogen or pinacole, and $R^c$ represents an appropriate 5- or 6-membered heteroaryl radical) in the presence of a base like $Na_2CO_3$ or $K_3PO_4$, and a palladium catalyst like $Pd(PPh_3)_4$, or $Pd(OAc)_2$ and (S)-Phos to give a compound of formula I-A (wherein X represents bond) (Scheme 3).

Scheme 3. Synthesis of a compound of formula I-A.

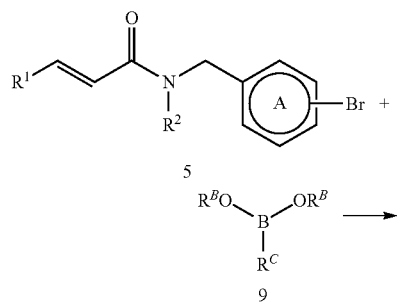

Scheme 4. Synthesis of a compound of formula I-B.

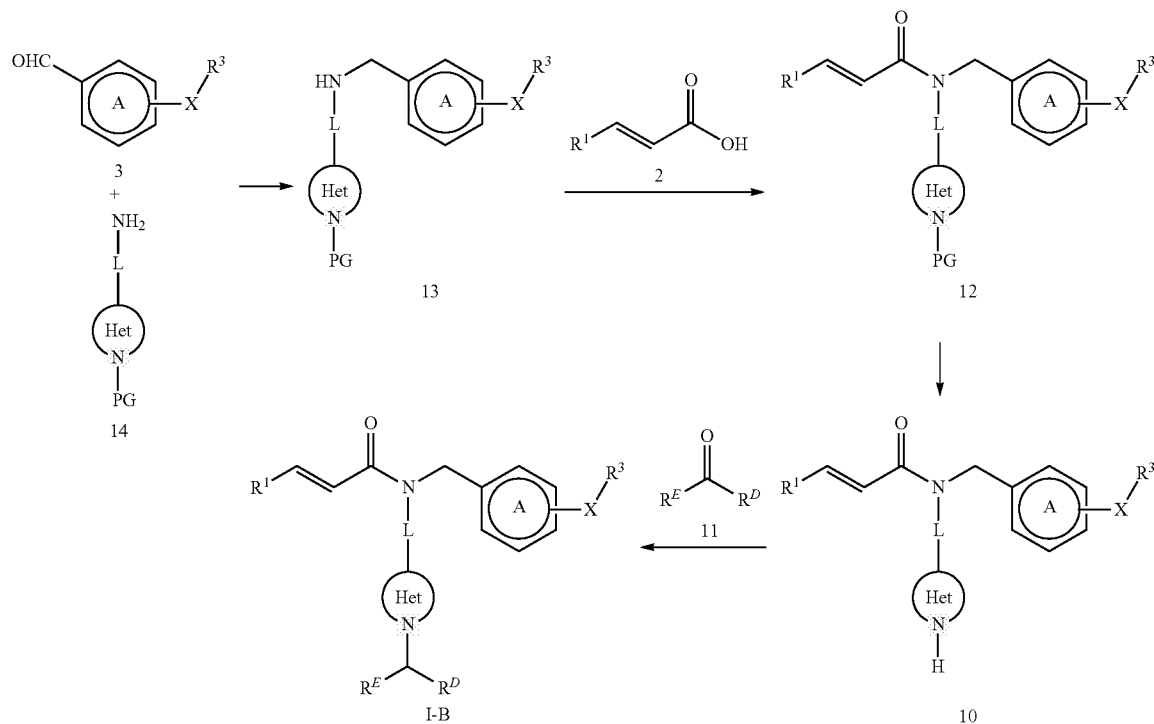

If not commercially available, aldehyde 3 can be prepared according to the Scheme 5. The bromide 15 (wherein for example ring A represents phenylene or pyridin-diyl) undergoes Buchwald-Hartwig cross-coupling with an amine 6 in the presence of palladium catalyst like $Pd_2(dba)_3$, a ligand like X-phos, a base like NaOtBu and a solvent like dioxane. Heating the resulting intermediate 16 in a mixture of water and THF in the presence of an acid like para-toluenesulfonic acid yields an aldehyde 3-A.

Scheme 5. Synthesis of an aldehyde 3-A.

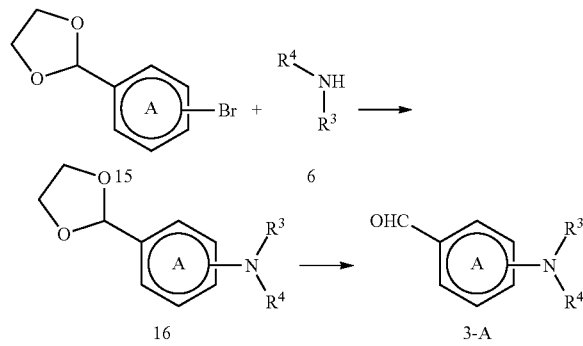

Amines 4 are commercially available, known in the art, or obtainable according to the Scheme 6.

An cyclic amine 17 undergoes a reductive amination with an appropriate aldehyde or ketone 11 in the presence of a reducing agent like $NaHB(OAc)_3$ to give a protected amine 18. If 11 is a ketone, activation with a Lewis acid or AcOH may be required. An amine 4-A is obtained after removal of a protecting group (PG) from the compound 18, applying reaction conditions known to a skilled person. Preferably, PG is a group such as tert-butoxycarbonyl. A tert-butoxycarbonyl group is cleaved under acidic conditions.

Scheme 6. Synthesis of an amine 4-A or 4-B.

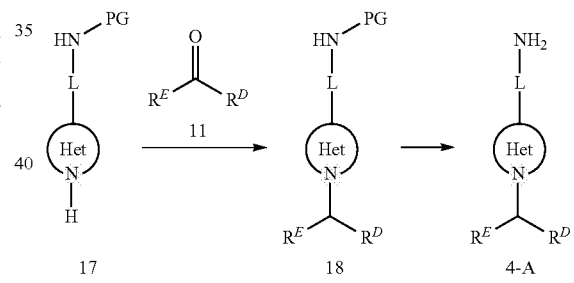

The following examples illustrate the present invention. All solvents and reagents are used as obtained from commercial sources unless otherwise stated. All temperatures are indicated in degrees Celsius and pressures in mbar. Unless mentioned otherwise, the reactions take place at room temperature (r.t.). In mixtures, relations of parts of solvent or eluent or reagent mixtures in liquid form are given as volume relations (v/v), unless indicated otherwise.

Whenever the compounds of formula I or II are obtained in the form of mixtures of stereoisomers such as especially enantiomers, the stereoisomers can be separated using methods known to one skilled in the art: e.g. by formation and separation of diastereomeric salts or by HPLC over a chiral stationary phase such as a Daicel ChiralPak AD-H (5 μm) column, a Daicel ChiralCel OD-H (5 μm) column, a Daicel ChiralCel OD (10 μm) column, a Daicel ChiralPak IA (5 μm) column, a Daicel ChiralPak IB (5 μm) column, a Daicel ChiralPak IC (5 μm) column, or a (R,R)-Whelk-01 (5 μm) column. Typical conditions of chiral HPLC are an isocratic mixture of eluent A (EtOH, in presence or absence of a base like triethylamine and/or diethylamine or of an acid like TFA) and eluent B (heptane).

EXPERIMENTAL PART

General Conditions

Analytical HPLC Conditions:
LC-MS 1:
LC-MS-conditions: Analytical. Pump: Waters Acquity Binary, Solvent Manager, MS: Waters SQ Detector, DAD: Acquity UPLC PDA Detector, ELSD: Acquity UPLC ELSD. Column: Acquity UPLC BEH C18 1.7 µm 2.1×50 mm from Waters, thermostated in the Acquity UPLC Column Manager at 60° C. Eluents: A: $H_2O+0.05\%$ formic acid or TFA; B: MeCN+0.045% formic acid or TFA. Method: Gradient: 2% B 98% B over 2.0 min. Flow: 1.0 ml/min. Detection: UV 214 nm and ELSD, and MS, RT is given in min.

LC-MS 1 FA: Eluents: A: $H_2O+0.05\%$ formic acid; B: MeCN+0.045% formic acid

LC-MS 1TFA: Eluents: A: $H_2O+0.05\%$ TFA; B: MeCN+0.045% TFA

LC-MS2 to LC-MS4:
HPLC/MS analyses are performed on a Ultimate 3000RS Dionex HPLC instrument, equipped with a Dionex Ultimate 3000 RS Photodiode Array Detector, a Dionex Ultimate 3000RS pump and a Dionex $MSQ^+$ mass spectrometer.

The LC retention times are obtained using the following elution conditions:

- LC-MS 2: Analytical HPLC on a Waters X-Bridge C18 column (4.6×30 mm, 2.5 µm, Waters); Linear gradient of water/0.04% TFA (A) and MeCN (B) from 5% to 95% B over 1.5 min; flow rate 4.5 mL/min, detection at 215 nm.
- LC-MS 3: Analytical HPLC on a Waters X-Bridge C18 column (4.6×30 mm, 2.5 µm, Waters); Linear concentrated $NH_3$ in water (1.0 ml/l) (A) and MeCN (B) from 5% to 95% B over 1.5 min; flow rate 4.5 mL/min, detection at 215 nm.
- LC-MS 4: Analytical HPLC on a Zorbax® SB-AQ column (4.6×50 mm, 3.5 µm, Agilent); Linear gradient of water/0.04% TFA (A) and MeCN (B) from 5% to 95% B over 1.5 min; flow rate 4.5 mL/min, detection at 215 nm.

Preparative HPLC Conditions:
Preparative HPLC/MS purifications are performed on a Gilson HPLC system, equipped with a Gilson 215 autosampler, Gilson 333/334 pumps, Finnigan AQA MS detector system, and a Dionex UV detector, using a Waters Xbridge C18 or an Waters Atlantis T3 column, with a linear gradient of water/formic acid 0.02% (A) and MeCN (B) (acidic conditions) or water/ammonia 0.02% (A) and MeCN (B) (basic conditions).

Flash Chromatography
Flash chromatography purifications are performed using $SiO_2$ 60 (230-400 mesh, particle size 40-63 µm) from Fluka.

Flashmaster purifications are performed using a Büchi system (Büchi Fraction Collector C-660, Büchi Pump Manager C-615, Büchi Pump Module C-605).

ABBREVIATIONS

As Used Herein Below and in the Description Above

Ac acetyl
AcOEt ethyl acetate
AcOH acetic acid
aq. aqueous
Ar argon
Boc tert-butyloxycarbonyl
CC column chromatography on silica gel
comb. combined
conc. concentrated
DBU 1,8-diazabicyclo[5.4.0]undec-7-ene
DCC 1,3-dicyclohexylcarbodiimide
DCM dichloromethane
DIPEA N,N-diisopropylethylamine
DMA dimethylacetamide
DMF N,N-dimethylformamide
DMSO dimethylsulfoxide
EDC 1-ethyl-3-(3-dimethylaminopropyl)carbodiimide
EtOH ethanol
HATU O-(7-azabenzotriazol-1-yl)-N,N,N',N'-tetramethyluronium hexafluorophosphate
Hept heptane
HOAT 7-aza-1-hydroxybenzotriazole
HPLC high performance liquid chromatography
LC-MS liquid chromatography—mass spectroscopy
M molarity [mol $L^{-1}$]
MeCN acetonitrile
MeOH methanol
min minute(s)
MS mass spectroscopy
N normality of solution
org. organic
$Pd_2(dba)_3$ tris(dibenzylideneacetone)dipalladium(0)
prep. preparative
quant. quantitative
r.t. room temperature
RT retention time
sat. saturated
Si-DCC polymer supported 1,3-dicyclohexylcarbodiimide
SK-0002-A chloro-2-(dimethylaminomethyl)-ferrocen-1-yl-(dinorbornylphosphine)palladium
soln. solution
S-Phos 2-dicyclohexylphosphino-2',6'-dimethoxybiphenyl
TBTU 0-(benzotriazol-1-yl)-N,N,N',N'-tetramethyluronium
TFA trifluoroacetic acid
THF tetrahydrofuran
UV ultraviolet
Vis visible
X-Phos 2-dicyclohexylphosphino-2',4',6'-triisopropylbiphenyl

GENERAL METHODS AND EXAMPLES

The following examples illustrate the preparation of compounds of the invention but do not at all limit the scope thereof. First the synthesis of example compounds of Formula I is described, followed by the description of the synthesis of intermediates and starting materials. Whenever used in the experimental part, generic Structures 1, 2, 3 etc. refer to the respective structures described in preceeding general description of the preparation of compounds of Formula I. Compounds denoted with (±) are prepared as racemic mixtures.

General Method for the Preparation of Compounds of Formula I

Boc Deprotection

To an ice-cooled solution of 4-{[4-(methyl-pyridin-4-yl-amino)-benzyl]-[(E)-3-(4-trifluoromethyl-phenyl)-acryloyl]-amino}-piperidine-1-carboxylic acid tert-butyl ester (2.57 g, 4.33 mmol, 1.0 eq.) in DCM (100 mL), 4M HCl in dioxane (10 mL) was added. The resulting solution was stirred at r.t. for 4 hours. The reaction mixture was concentrated in vacuo. The residue was purified by prep. HPLC column: X-bridge, 30×75 mm, 10 µm, UV/MS, basic conditions) and concentrated in vacuo.

Listed in Table 1 below are examples of compounds of Formula I, prepared according to the above-mentioned method with the corresponding Boc-protected amine 12 as starting material.

TABLE 1

| Example | Compound of Formula I | $t_R$ [min] LC-MS Method | MS-data m/z $[M + H]^+$ |
|---|---|---|---|
| 1 | (E)-N-[4-(Methyl-pyridin-4-yl-amino)-benzyl]-N-piperidin-4-yl-3-(4-trifluoromethyl-phenyl)-acrylamide | 0.69 LC-MS 1TFA | 495.4 |
| 2 | (E)-N-[4-(Methyl-pyridin-4-yl-amino)-benzyl]-N-(S)-piperidin-3-yl-3-(4-trifluoromethyl-phenyl)-acrylamide | 0.69 LC-MS 1TFA | 495.3 |

Reductive Amination

Method A: To a solution of (E)-N-[4-(Methyl-pyridin-4-yl-amino)-benzyl]-N-piperidin-4-yl-3-(4-trifluoromethyl-phenyl)-acrylamide (57 mg, 0.1 mmol, 1.0 eq.) and 4-trifluormethylbenzaldehyde (35 mg, 0.2 mmol, 2.0 eq.) in DCM/MeOH 1:1 (1 mL), acetic acid (6 µL, 0.1 mmol, 1.0 eq.) was added. The mixture was stirred at r.t. for 30 min, then sodium triacetoxyborohydride (42 mg, 0.2 mmol, 2.0 eq.) was added. The mixture was stirred at r.t. for 21 hours. Sat. aq. NaHCO₃ soln. (0.5 mL) was added and the mixture was stirred at r.t. for 30 min. The mixture was concentrated in vacuo. The residue was partitioned between DCM and water. The layers were separated and the aq. phase was extracted with DCM. The comb. org. phases were concentrated in vacuo. The residue was purified by prep. HPLC column: X-bridge, 30×75 mm, 10 µm, UV/MS, basic conditions), and concentrated in vacuo.

Listed in Table 2 below are examples of compounds of Formula I, prepared according to the above-mentioned method with the corresponding amine of Structure 10 and the corresponding aldehyde or ketone 11 as starting materials.

TABLE 2

| Example | Compound of Formula I | $t_R$ [min] LC-MS Method | MS-data m/z $[M + H]^+$ |
|---|---|---|---|
| 3 | (E)-N-[4-(Methyl-pyridin-4-yl-amino)-benzyl]-N-[1-(4-trifluoromethyl-benzyl)-piperidin-4-yl]-3-(4-trifluoromethyl-phenyl)-acrylamide | 0.85 LC-MS 1TFA | 653.4 |
| 4 | (E)-N-[1-(2-Methyl-oxazol-4-ylmethyl)-piperidin-4-yl]-N-[4-(methyl-pyridin-4-yl-amino)-benzyl]-3-(4-trifluoromethyl-phenyl)-acrylamide | 0.79 LC-MS 1TFA | 590.4 |
| 5 | (E)-N-(1-Cyclopentyl-piperidin-4-yl)-N-[4-(methyl-pyridin-4-yl-amino)-benzyl]-3-(4-trifluoromethyl-phenyl)-acrylamide | 0.75 LC-MS 1TFA | 563.4 |
| 6 | (E)-N-(1-Benzyl-piperidin-4-yl)-N-[4-(methyl-pyridin-4-yl-amino)-benzyl]-3-(4-trifluoromethyl-phenyl)-acrylamide | 0.77 LC-MS 1TFA | 585.5 |
| 7 | (E)-N-(1-Ethyl-piperidin-4-yl)-N-[4-(methyl-pyridin-4-yl-amino)-benzyl]-3-(4-trifluoromethyl-phenyl)-acrylamide | 0.71 LC-MS 1TFA | 523.4 |
| 8 | (E)-N-[1-(3-Methyl-butyl)-piperidin-4-yl]-N-[4-(methyl-pyridin-4-yl-amino)-benzyl]-3-(4-trifluoromethyl-phenyl)-acrylamide | 0.78 LC-MS 1TFA | 565.5 |
| 9 | (E)-N-(1-Cyclopropylmethyl-piperidin-4-yl)-N-[4-(methyl-pyridin-4-yl-amino)-benzyl]-3-(4-trifluoromethyl-phenyl)-acrylamide | 0.73 LC-MS 1TFA | 549.5 |
| 10 | (E)-N-(1'-Bicyclo[2.2.1]hept-5-en-2-ylmethyl-piperidin-4-yl)-N-[4-(methyl-pyridin-4-yl-amino)-benzyl]-3-(4-trifluoromethyl-phenyl)-acrylamide | 0.80 LC-MS 1TFA | 601.5 |
| 11 | (E)-N-[1-(3,4-Dichloro-benzyl)-piperidin-4-yl]-N-[4-(methyl-pyridin-4-yl-amino)-benzyl]-3-(4-trifluoromethyl-phenyl)-acrylamide | 0.85 LC-MS 1TFA | 653.5 |
| 12 | (E)-N-[1-(4-Methyl-benzyl)-piperidin-4-yl]-N-[4-(methyl-pyridin-4-yl-amino)-benzyl]-3-(4-trifluoromethyl-phenyl)-acrylamide | 0.81 LC-MS 1TFA | 599.5 |
| 13 | (E)-N-[1-(4-Methoxy-benzyl)-piperidin-4-yl]-N-[4-(methyl-pyridin-4-yl-amino)-benzyl]-3-(4-trifluoromethyl-phenyl)-acrylamide | 0.79 LC-MS 1TFA | 615.5 |
| 14 | (E)-N-[4-(Methyl-pyridin-4-yl-amino)-benzyl]-N-(1-phenethyl-piperidin-4-yl)-3-(4-trifluoromethyl-phenyl)-acrylamide | 0.80 LC-MS 1TFA | 599.4 |
| 15 | (E)-N-[1-(2,2-Diphenyl-ethyl)-piperidin-4-yl]-N-[4-(methyl-pyridin-4-yl-amino)-benzyl]-3-(4-trifluoromethyl-phenyl)-acrylamide | 0.88 LC-MS 1TFA | 675.5 |
| 16 | (E)-N-[4-(Methyl-pyridin-4-yl-amino)-benzyl]-3-(4-trifluoromethyl-phenyl)-N-[1-(3,3,3-trifluoro-propyl)-piperidin-4-yl]-acrylamide | 0.75 LC-MS 1TFA | 591.4 |
| 17 | (E)-N-[1-(2-Methyl-2H-pyrazol-3-ylmethyl)-piperidin-4-yl]-N-[4-(methyl-pyridin-4-yl-amino)-benzyl]-3-(4-trifluoromethyl-phenyl)-acrylamide | 0.71 LC-MS 1TFA | 589.4 |
| 18 | (E)-N-[4-(Methyl-pyridin-4-yl-amino)-benzyl]-N-[1-(1-phenyl-1H-pyrazol-4-ylmethyl)-piperidin-4-yl]-3-(4-trifluoromethyl-phenyl)-acrylamide | 0.81 LC-MS 1TFA | 651.5 |
| 19 | (E)-N-[1-(3-Methyl-3H-imidazol-4-ylmethyl)-piperidin-4-yl]-N-[4-(methyl-pyridin-4-yl-amino)-benzyl]-3-(4-trifluoromethyl-phenyl)-acrylamide | 0.64 LC-MS 1TFA | 589.5 |
| 20 | (E)-N-(1-Imidazo[1,5-a]pyridin-3-ylmethyl-piperidin-4-yl)-N-[4-(methyl-pyridin-4-yl-amino)-benzyl]-3-(4-trifluoromethyl-phenyl)-acrylamide | 0.75 LC-MS 1TFA | 625.5 |

TABLE 2-continued

| Example | Compound of Formula I | $t_R$ [min] LC-MS Method | MS-data m/z $[M + H]^+$ |
|---|---|---|---|
| 21 | (E)-N-[1-(1-Methyl-1H-benzoimidazol-2-ylmethyl)-piperidin-4-yl]-N-[4-(methyl-pyridin-4-yl-amino)-benzyl]-3-(4-trifluoromethyl-phenyl)-acrylamide | 0.78 LC-MS 1TFA | 639.7 |
| 22 | (E)-N-[4-(Methyl-pyridin-4-yl-amino)-benzyl]-N-(1-pyridin-2-ylmethyl-piperidin-4-yl)-3-(4-trifluoromethyl-phenyl)-acrylamide | 0.73 LC-MS 1TFA | 586.5 |
| 23 | (E)-N-[4-(Methyl-pyridin-4-yl-amino)-benzyl]-N-(1-pyridin-3-ylmethyl-piperidin-4-yl)-3-(4-trifluoromethyl-phenyl)-acrylamide | 0.68 LC-MS 1TFA | 586.4 |
| 24 | (E)-N-[4-(Methyl-pyridin-4-yl-amino)-benzyl]-N-[1-(2-methyl-pyrimidin-5-ylmethyl)-piperidin-4-yl]-3-(4-trifluoromethyl-phenyl)-acrylamide | 0.70 LC-MS 1TFA | 601.5 |
| 25 | (E)-N-(1-Imidazo[1,2-a]pyridin-7-ylmethyl-piperidin-4-yl)-N-[4-(methyl-pyridin-4-yl-amino)-benzyl]-3-(4-trifluoromethyl-phenyl)-acrylamide | 0.64 LC-MS 1TFA | 625.6 |
| 26 | (E)-N-(1'-Methyl-[1,4']bipiperidinyl-4-yl)-N-[4-(methyl-pyridin-4-yl-amino)-benzyl]-3-(4-trifluoromethyl-phenyl)-acrylamide | 0.64 LC-MS 1TFA | 592.4 |
| 27 | (E)-N-[1-(4-Cyano-benzyl)-piperidin-4-yl]-N-[4-(methyl-pyridin-4-yl-amino)-benzyl]-3-(4-trifluoromethyl-phenyl)-acrylamide | 0.76 LC-MS 1TFA | 610.4 |
| 28 | (E)-N-[1-(1-Acetyl-1H-indol-3-ylmethyl)-piperidin-4-yl]-N-[4-(methyl-pyridin-4-yl-amino)-benzyl]-3-(4-trifluoromethyl-phenyl)-acrylamide | 0.82 LC-MS 1TFA | 666.5 |
| 29 | (E)-N-[4-(Methyl-pyridin-4-yl-amino)-benzyl]-N-(1-pyrimidin-2-ylmethyl-piperidin-4-yl)-3-(4-trifluoromethyl-phenyl)-acrylamide | 0.71 LC-MS 1TFA | 587.5 |
| 30 | (±)-(E)-N-[4-(Methyl-pyridin-4-yl-amino)-benzyl]-N-[1-(1-phenyl-ethyl)-piperidin-4-yl]-3-(4-trifluoromethyl-phenyl)-acrylamide | 0.80 LC-MS 1TFA | 599.4 |

Method B: To a solution of (E)-N-[4-(2-methyl-pyridin-4-ylamino)-benzyl]-N-piperidin-4-yl-3-(4-trifluoromethyl-phenyl)-acrylamide (50 mg, 0.1 mmol, 1.0 eq.) in DCM (1 mL), cyclopropanecarboxaldehyde (7 mg, 0.1 mmol, 1.0 eq.) was added. The mixture was stirred at r.t. for 20 min. Sodium triacetoxyborohydride (42 mg, 0.20 mmol, 2.0 eq.) was added. The mixture was stirred at r.t. for 2 hours. Sat. aq. NaHCO$_3$ soln. (1 mL) and DCM (1 mL) were added. The resulting mixture was stirred at r.t. for 30 min. The layers were separated and the aq. phase was extracted with DCM (5×1 mL). The comb. org. phases were concentrated in vacuo. The residue was purified by prep. HPLC (column: X-bridge, 30×75 mm, 10 μm, UV/MS, basic conditions), and concentrated in vacuo.

Listed in Table 3 below are examples of compounds of Formula I, prepared according to the above-mentioned method with the corresponding amine of Structure 10 and the corresponding aldehyde or ketone 11 as starting materials.

TABLE 3

| Example | Compound of Formula I | $t_R$ [min] LC-MS Method | MS-data m/z $[M + H]^+$ |
|---|---|---|---|
| 31 | (E)-N-(1-Cyclopropylmethyl-piperidin-4-yl)-N-[4-(2-methyl-pyridin-4-ylamino)-benzyl]-3-(4-trifluoromethyl-phenyl)-acrylamide | 0.73 LC-MS 1TFA | 549.4 |
| 32 | (E)-N-[1-(2,5-Dimethyl-oxazol-4-ylmethyl)-piperidin-4-yl]-N-[4-(2-methyl-pyridin-4-ylamino)-benzyl]-3-(4-trifluoromethyl-phenyl)-acrylamide | 0.75 LC-MS 1TFA | 604.5 |
| 33 | (E)-N-[4-(2-Methyl-pyridin-4-ylamino)-benzyl]-N-(1-propyl-piperidin-4-yl)-3-(4-trifluoromethyl-phenyl)-acrylamide | 0.73 LC-MS 1TFA | 537.4 |
| 34 | (E)-N-[1-(5-Methyl-isoxazol-3-ylmethyl)-piperidin-4-yl]-N-[4-(2-methyl-pyridin-4-ylamino)-benzyl]-3-(4-trifluoromethyl-phenyl)-acrylamide | 0.74 LC-MS 1TFA | 590.3 |
| 35 | (E)-N-[4-(2-Methyl-pyridin-4-ylamino)-benzyl]-N-[1-(4-methyl-thiazol-5-ylmethyl)-piperidin-4-yl]-3-(4-trifluoromethyl-phenyl)-acrylamide | 0.72 LC-MS 1TFA | 606.4 |
| 36 | (E)-N-[1-(2-Methyl-oxazol-4-ylmethyl)-piperidin-4-yl]-N-[4-(2-methyl-pyridin-4-ylamino)-benzyl]-3-(4-trifluoromethyl-phenyl)-acrylamide | 0.72 LC-MS 1TFA | 590.4 |
| 37 | (E)-N-(1-Benzyl-piperidin-4-yl)-N-[4-(2-methyl-pyridin-4-ylamino)-benzyl]-3-(4-trifluoromethyl-phenyl)-acrylamide | 0.77 LC-MS 1TFA | 585.4 |
| 38 | (E)-N-(1-Imidazo[1,2-a]pyridin-3-ylmethyl-piperidin-4-yl)-N-[4-(2-methyl-pyridin-4-ylamino)-benzyl]-3-(4-trifluoromethyl-phenyl)-acrylamide | 0.66 LC-MS 1TFA | 625.5 |
| 39 | (E)-N-[4-(2-Methyl-pyridin-4-ylamino)-benzyl]-3-(4-trifluoromethyl-phenyl)-N-[1-(3,3,3-trifluoro-propyl)-piperidin-4-yl]-acrylamide | 0.75 LC-MS 1TFA | 591.4 |
| 40 | (E)-N-[4-(2-Methyl-pyridin-4-ylamino)-benzyl]-N-(1-thiazol-2-ylmethyl-piperidin-4-yl)-3-(4-trifluoromethyl-phenyl)-acrylamide | 0.73 LC-MS 1TFA | 592.4 |

TABLE 3-continued

| Example | Compound of Formula I | $t_R$ [min] LC-MS Method | MS-data m/z [M + H]⁺ |
|---|---|---|---|
| 41 | (E)-N-[1-(1-Methyl-1H-imidazol-2-ylmethyl)-piperidin-4-yl]-N-[4-(2-methyl-pyridin-4-ylamino)-benzyl]-3-(4-trifluoromethyl-phenyl)-acrylamide | 0.71 LC-MS 1TFA | 589.5 |
| 42 | (E)-N-[4-(2-Methyl-pyridin-4-ylamino)-benzyl]-N-[1-(4-methyl-thiazol-2-ylmethyl)-piperidin-4-yl]-3-(4-trifluoromethyl-phenyl)-acrylamide | 0.75 LC-MS 1TFA | 606.4 |
| 43 | (E)-N-[1-(2,5-Dimethyl-2H-pyrazol-3-ylmethyl)-piperidin-4-yl]-N-[4-(2-methyl-pyridin-4-ylamino)-benzyl]-3-(4-trifluoromethyl-phenyl)-acrylamide | 0.72 LC-MS 1TFA | 603.4 |
| 44 | (E)-N-[1-(3,5-Dimethyl-isoxazol-4-ylmethyl)-piperidin-4-yl]-N-[4-(2-methyl-pyridin-4-ylamino)-benzyl]-3-(4-trifluoromethyl-phenyl)-acrylamide | 0.74 LC-MS 1TFA | 604.4 |
| 45 | (E)-N-(1-Imidazo[1,5-a]pyridin-1-ylmethyl-piperidin-4-yl)-N-[4-(2-methyl-pyridin-4-ylamino)-benzyl]-3-(4-trifluoromethyl-phenyl)-acrylamide | 0.75 LC-MS 1TFA | 625.5 |
| 46 | (E)-N-(1-Imidazo[1,5-a]pyridin-3-ylmethyl-piperidin-4-yl)-N-[4-(2-methyl-pyridin-4-ylamino)-benzyl]-3-(4-trifluoromethyl-phenyl)-acrylamide | 0.75 LC-MS 1TFA | 625.5 |
| 47 | (E)-N-[4-(2-Methyl-pyridin-4-ylamino)-benzyl]-N-(1-pyrimidin-2-ylmethyl-piperidin-4-yl)-3-(4-trifluoromethyl-phenyl)-acrylamide | 0.71 LC-MS 1TFA | 587.4 |
| 48 | (E)-N-[4-(2-Methyl-pyridin-4-ylamino)-benzyl]-N-(1-pyridin-3-ylmethyl-piperidin-4-yl)-3-(4-trifluoromethyl-phenyl)-acrylamide | 0.68 LC-MS 1TFA | 586.5 |
| 49 | (E)-N-[4-(2-Methyl-pyridin-4-ylamino)-benzyl]-N-(1-pyrimidin-5-ylmethyl-piperidin-4-yl)-3-(4-trifluoromethyl-phenyl)-acrylamide | 0.69 LC-MS 1TFA | 587.4 |
| 50 | (E)-N-[1-(1-Methyl-1H-pyrazol-4-ylmethyl)-piperidin-4-yl]-N-[4-(2-methyl-pyridin-4-ylamino)-benzyl]-3-(4-trifluoromethyl-phenyl)-acrylamide | 0.71 LC-MS 1TFA | 589.4 |
| 51 | (E)-N-[4-(2-Methyl-pyridin-4-ylamino)-benzyl]-N-[1-(2-methyl-pyrimidin-5-ylmethyl)-piperidin-4-yl]-3-(4-trifluoromethyl-phenyl)-acrylamide | 0.70 LC-MS 1TFA | 601.4 |
| 52 | (E)-N-[1-(2,3-Dimethyl-3H-imidazol-4-ylmethyl)-piperidin-4-yl]-N-[4-(2-methyl-pyridin-4-ylamino)-benzyl]-3-(4-trifluoromethyl-phenyl)-acrylamide | 0.64 LC-MS 1TFA | 603.5 |

Method C: To a solution of 3-dimethylaminomethyl-4-hydroxy-benzaldehyde (22 mg, 0.12 mmol, 1.0 eq.) in acetonitrile (1.0 mL), a solution of (E)-N-[4-(2-methyl-pyridin-4-ylamino)-benzyl]-N-piperidin-4-yl-3-(4-trifluoromethyl-phenyl)-acrylamide (60 mg, 0.12 mmol, 1.0 eq.) in acetonitrile/DMF 1:1 (2 mL) was added. Sodium triacetoxyborohydride (39 mg, 0.18 mmol, 1.5 eq.) was added portionwise and the reaction mixture was stirred at r.t. for 18 hours. 3-Dimethylaminomethyl-4-hydroxy-benzaldehyde (22 mg, 0.12 mmol, 1.0 eq.) and sodium triacetoxyborohydride (51 mg, 0.24 mmol, 2.0 eq.) were added. The mixture was stirred at r.t. for 18 hours. The resulting suspension was filtered and the filtrate purified by prep. HPLC (column: Waters X-Bridge, 30×75 mm, 10 μm, UV/MS, basic conditions) and concentrated in vacuo.

Listed in Table 4 below are examples of compounds of Formula I, prepared according to the above-mentioned method with the corresponding amine of Structure 10 and the corresponding aldehyde 11 as starting materials.

Method D: To a solution of (E)-N-[4-(methyl-pyridin-4-yl-amino)-benzyl]-N—(S)-piperidin-3-yl-3-(4-trifluoromethyl-phenyl)-acrylamide (42 mg, 0.085 mmol, 1.0 eq.) in acetonitrile (1 mL), N-methyl-4-piperidone (10 μL, 0.079 mmol, 0.9 eq.) was added. The reaction mixture was stirred at r.t. for 2 hours. Sodium triacetoxyborohydride (25 mg, 0.12 mmol, 1.4 eq.) was added portionwise and the reaction mixture was stirred at r.t. for 18 hours. The mixture was filtered through isolute H-NM and purified by prep. HPLC (column: Waters X-Bridge, 30×75 mm, 10 μm, UV/MS, acidic conditions) and concentrated in vacuo.

Listed in Table 5 below are examples of compounds of Formula I, prepared according to the above-mentioned method with the corresponding amine of Structure 10 and the corresponding aldehyde or ketone 11 as starting materials.

TABLE 4

| Example | Compound of Formula I | $t_R$ [min] LC-MS Method | MS-data m/z [M + H]⁺ |
|---|---|---|---|
| 53 | (E)-N-[1-(3-Dimethylaminomethyl-4-hydroxy-benzyl)-piperidin-4-yl]-N-[4-(2-methyl-pyridin-4-ylamino)-benzyl]-3-(4-trifluoromethyl-phenyl)-acrylamide | 0.65 LC-MS 1TFA | 658.5 |
| 54 | (E)-N-[1-(3-Diethylaminomethyl-4-hydroxy-benzyl)-piperidin-4-yl]-N-[4-(2-methyl-pyridin-4-ylamino)-benzyl]-3-(4-trifluoromethyl-phenyl)-acrylamide | 0.67 LC-MS 1TFA | 686.5 |

TABLE 5

| Example | Compound of Formula I | $t_R$ [min] LC-MS Method | MS-data m/z [M + H]+ |
|---|---|---|---|
| 55 | (S,E)-N-(4-(methyl(pyridin-4-yl)amino)benzyl)-N-(1'-methyl-[1,4'-bipiperidin]-3-yl)-3-(4-(trifluoromethyl)phenyl)acrylamide | 0.62 LC-MS 1TFA | 592.4 |
| 56 | (R,E)-N-(4-(methyl(pyridin-4-yl)amino)benzyl)-N-(1'-methyl-[1,4'-bipiperidin]-3-yl)-3-(4-(trifluoromethyl)phenyl)acrylamide | 0.63 LC-MS 1TFA | 592.5 |
| 57 | (±)-(E)-N-(4-(methyl(pyridin-4-yl)amino)benzyl)-N-(1-(1-methylpiperidin-4-yl)azepan-4-yl)-3-(4-(trifluoromethyl)phenyl)acrylamide | 0.64 LC-MS 1TFA | 606.5 |
| 58 | (S,E)-N-(1-cyclopentylpiperidin-3-yl)-N-(4-(methyl(pyridin-4-yl)amino)benzyl)-3-(4-(trifluoromethyl)phenyl)acrylamide | 0.76 LC-MS 1TFA | 563.4 |
| 59 | (R,E)-N-(1-cyclopentylpiperidin-3-yl)-N-(4-(methyl(pyridin-4-yl)amino)benzyl)-3-(4-(trifluoromethyl)phenyl)acrylamide | 0.66 LC-MS 4 | 563.3 |
| 60 | (±)-(E)-N-(1-cyclopentylazepan-4-yl)-N-(4-(methyl(pyridin-4-yl)amino)benzyl)-3-(4-(trifluoromethyl)phenyl)acrylamide | 0.90 LC-MS 1TFA | 577.6 |
| 61 | (S,E)-N-(1-isopentylpiperidin-3-yl)-N-(4-(methyl(pyridin-4-yl)amino)benzyl)-3-(4-(trifluoromethyl)phenyl)acrylamide | 0.80 LC-MS 1TFA | 565.4 |
| 62 | (R,E)-N-(1-isopentylpiperidin-3-yl)-N-(4-(methyl(pyridin-4-yl)amino)benzyl)-3-(4-(trifluoromethyl)phenyl)acrylamide | 0.80 LC-MS 1TFA | 565.5 |
| 63 | (±)-(E)-N-(1-isopentylazepan-4-yl)-N-(4-(methyl(pyridin-4-yl)amino)benzyl)-3-(4-(trifluoromethyl)phenyl)acrylamide | 0.86 LC-MS 1TFA | 579.5 |
| 64 | (E)-N-(4-(methyl(pyridin-4-yl)amino)benzyl)-N-((3aR,6aS)-2-(1-methylpiperidin-4-yl)octahydrocyclopenta[c]pyrrol-5-yl)-3-(4-(trifluoromethyl)phenyl)acrylamide (mixture of stereoisomers) | 0.65 LC-MS 1TFA | 618.5 |
| 65 | (E)-N-(4-(methyl(pyridin-4-yl)amino)benzyl)-N-(3-(1-methylpiperidin-4-yl)-3-azaspiro[5.5]undecan-9-yl)-3-(4-(trifluoromethyl)phenyl)acrylamide | 0.68 LC-MS 1TFA | 660.6 |
| 66 | (E)-N-((3aR,6aS)-2-cyclopentyloctahydrocyclopenta[c]pyrrol-5-yl)-N-(4-(methyl(pyridin-4-yl)amino)benzyl)-3-(4-(trifluoromethyl)phenyl)acrylamide (mixture of stereoisomers) | 0.72 LC-MS 1TFA | 589.5 |
| 67 | (E)-N-(3-cyclopentyl-3-azaspiro[5.5]undecan-9-yl)-N-(4-(methyl(pyridin-4-yl)amino)benzyl)-3-(4-(trifluoromethyl)phenyl)acrylamide | 0.76 LC-MS 1TFA | 631.5 |
| 68 | (E)-N-((3aR,6aS)-2-isopentyloctahydrocyclopenta[c]pyrrol-5-yl)-N-(4-(methyl(pyridin-4-yl)amino)benzyl)-3-(4-(trifluoromethyl)phenyl)acrylamide (mixture of stereoisomers) | 0.81 LC-MS 1TFA | 591.5 |
| 69 | (E)-N-(3-isopentyl-3-azaspiro[5.5]undecan-9-yl)-N-(4-(methyl(pyridin-4-yl)amino)benzyl)-3-(4-(trifluoromethyl)phenyl)acrylamide | 0.85 LC-MS 1TFA | 633.6 |
| 70 | (±)-(E)-N-(4-(methyl(pyridin-4-yl)amino)benzyl)-N-(1-(1-methylpiperidin-4-yl)azepan-3-yl)-3-(4-(trifluoromethyl)phenyl)acrylamide | 0.64 LC-MS 1TFA | 606.5 |
| 71 | (±)-(E)-N-(1-cyclopentylazepan-3-yl)-N-(4-(methyl(pyridin-4-yl)amino)benzyl)-3-(4-(trifluoromethyl)phenyl)acrylamide | 0.81 LC-MS 1TFA | 577.5 |
| 72 | (±)-(E)-N-(1-isopentylazepan-3-yl)-N-(4-(methyl(pyridin-4-yl)amino)benzyl)-3-(4-(trifluoromethyl)phenyl)acrylamide | 0.73 LC-MS 4 | 579.2 |
| 73 | (E)-N-(4-(methyl(pyridin-4-yl)amino)benzyl)-N-(2-(1-methylpiperidin-4-yl)-2-azaspiro[3.3]heptan-6-yl)-3-(4-(trifluoromethyl)phenyl)acrylamide | 0.64 LC-MS 1TFA | 604.4 |
| 74 | (E)-N-(2-cyclopentyl-2-azaspiro[3.3]heptan-6-yl)-N-(4-(methyl(pyridin-4-yl)amino)benzyl)-3-(4-(trifluoromethyl)phenyl)acrylamide | 0.76 LC-MS 1TFA | 575.4 |
| 75 | (E)-N-(2-isopentyl-2-azaspiro[3.3]heptan-6-yl)-N-(4-(methyl(pyridin-4-yl)amino)benzyl)-3-(4-(trifluoromethyl)phenyl)acrylamide | 0.80 LC-MS 1TFA | 577.4 |
| 76 | (±)-(E)-N-(cis-1-cyclopentyl-3-fluoropiperidin-4-yl)-N-(4-(methyl(pyridin-4-yl)amino)benzyl)-3-(4-(trifluoromethyl)phenyl)acrylamide | 0.73 LC-MS 1TFA | 581.4 |
| 77 | (±)-(E)-N-(cis-3-fluoro-1-isopentylpiperidin-4-yl)-N-(4-(methyl(pyridin-4-yl)amino)benzyl)-3-(4-(trifluoromethyl)phenyl)acrylamide | 0.77 LC-MS 1TFA | 583.5 |
| 78 | (±)-(E)-N-(cis-3-fluoro-1'-methyl-[1,4'-bipiperidin]-4-yl)-N-(4-(methyl(pyridin-4-yl)amino)benzyl)-3-(4-(trifluoromethyl)phenyl)acrylamide | 0.56 LC-MS 4 | 610.2 |
| 79 | (±)-(E)-N-(trans-3-fluoro-1'-methyl-[1,4'-bipiperidin]-4-yl)-N-(4-(methyl(pyridin-4-yl)amino)benzyl)-3-(4-(trifluoromethyl)phenyl)acrylamide | 0.67 LC-MS 1TFA | 610.5 |
| 80 | (±)-(E)-N-(trans-1-cyclopentyl-3-fluoropiperidin-4-yl)-N-(4-(methyl(pyridin-4-yl)amino)benzyl)-3-(4-(trifluoromethyl)phenyl)acrylamide | 0.76 LC-MS 1TFA | 581.3 |
| 81 | (±)-(E)-N-(trans-3-fluoro-1-isopentylpiperidin-4-yl)-N-(4-(methyl(pyridin-4-yl)amino)benzyl)-3-(4-(trifluoromethyl)phenyl)acrylamide | 0.80 LC-MS 1TFA | 583.5 |

Method E: To a solution of (E)-N-[4-(methyl-pyridin-4-yl-amino)-benzyl]-N—(S)-piperidin-3-yl-3-(4-trifluoromethyl-phenyl)-acrylamide (50 mg, 0.10 mmol, 1.0 eq.) in MeCN (2 mL) acetaldehyde (6 μL, 0.10 mmol, 1.0 eq.) was added. The mixture was stirred at r.t. for 2 hours. Sodium triacetoxyborohydride (32 mg, 0.15 mmol, 1.5 eq.) was added. The mixture was stirred at r.t. for 18 hours. The reaction mixture was concentrated in vacuo and the residue was purified by prep. HPLC (column: Waters X-Bridge, 30×75 mm, 10 μm, UV/MS, basic conditions) and concentrated in vacuo.

Listed in Table 6 below are examples of compounds of Formula I, prepared according to the above-mentioned method with the corresponding amine of Structure 10 and the corresponding aldehyde or ketone 11 as starting materials.

TABLE 6

| Example | Compound of Formula I | $t_R$ [min] LC-MS Method | MS-data m/z $[M + H]^+$ |
|---|---|---|---|
| 82 | (E)-N-((S)-1-Ethyl-piperidin-3-yl)-N-[4-(methyl-pyridin-4-yl-amino)-benzyl]-3-(4-trifluoromethyl-phenyl)-acrylamide | 0.71 LC-MS 1TFA | 523.4 |
| 83 | (E)-N-((S)-1-Isopropyl-piperidin-3-yl)-N-[4-(methyl-pyridin-4-yl-amino)-benzyl]-3-(4-trifluoromethyl-phenyl)-acrylamide | 0.73 LC-MS 1TFA | 537.4 |

Example 84

(±)-(E)-N-[1-(2-Methoxy-1-methyl-ethyl)-piperidin-4-yl]-N-[4-(2-methyl-pyridin-4-ylamino)-benzyl]-3-(4-trifluoromethyl-phenyl)-acrylamide To a solution of (E)-N-[4-(2-methyl-pyridin-4-ylamino)-benzyl]-N-piperidin-4-yl-3-(4-trifluoromethyl-phenyl)-acrylamide (59 mg, 0.12 mmol, 1.2 eq.) in DCM (1 mL), methoxyacetone (9 mg, 0.10 mmol, 1.0 eq.) and AcOH (6 μL, 0.10 mmol, 1.0 eq.) were added. The mixture was stirred at r.t. for 1 hour. Sodium triacetoxyborohydride (42 mg, 0.20 mmol, 2.0 eq.) was added. The mixture was stirred at r.t. for 2 hours. Sat. aq. NaHCO$_3$ soln. (1 mL) and DCM (1 mL) were added. The resulting mixture was stirred at r.t. for 30 min. The layers were separated and the aq. phase was extracted with DCM (5×1 mL). The comb. org. phases were concentrated in vacuo. The residue was purified by prep. HPLC (column: X-bridge, 30×75 mm, 10 μm, UV/MS, basic conditions), and concentrated in vacuo.
LC-MS 1TFA: $t_R$=0.73 min; $[M+H]^+$=567.4

Buchwald Cross-Coupling

Method A: To a solution of (E)-N-(4-bromo-benzyl)-N-(1-cyclopentyl-piperidin-4-yl)-3-(4-trifluoromethyl-phenyl)-acrylamide (161 mg, 0.30 mmol, 1.00 eq.) in dioxane (1.5 mL), 4-amino-2-methylchinoline (48 mg, 0.30 mmol, 1.00 eq.) and sodium tert-butoxide (43 mg, 0.45 mmol, 1.50 eq.) were added. The solution was degased with N$_2$ for 15 min. The solution was heated to 105° C. A solution of the Pd catalyst Solvias SK-0002-A (9 mg, 0.02 mmol, 0.05 eq.) in dioxane (1 mL) previously degased with N$_2$ was added to the hot reaction mixture. The reaction was heated to 105° C. for 18 hours. The reaction mixture was allowed to cool to r.t. and filtered through Celite. The Celite was rinsed with dioxane and the filtrate concentrated in vacuo. The residue was purified by prep. HPLC (column: Waters X-bridge, 30×75 mm, 10 μm, UV/MS, basic conditions) and concentrated in vacuo.

Listed in Table 7 below are examples of compounds of Formula I, prepared according to the above-mentioned method with the corresponding amine 6 and the corresponding bromide of Structure 5 as starting materials.

TABLE 7

| Example | Compound of Formula I | $t_R$ [min] LC-MS Method | MS-data m/z $[M + H]^+$ |
|---|---|---|---|
| 85 | (E)-N-(1-Cyclopentyl-piperidin-4-yl)-N-[4-(2-methyl-quinolin-4-ylamino)-benzyl]-3-(4-trifluoromethyl-phenyl)-acrylamide | 0.80 LC-MS 1TFA | 613.5 |
| 86 | (E)-N-(1-Cyclopentyl-piperidin-4-yl)-N-[4-(pyridin-4-ylamino)-benzyl]-3-(4-trifluoromethyl-phenyl)-acrylamide | 0.74 LC-MS 1TFA | 549.4 |
| 87 | (E)-N-(1-Cyclopentyl-piperidin-4-yl)-N-[4-(2,6-dimethyl-pyridin-4-ylamino)-benzyl]-3-(4-trifluoromethyl-phenyl)-acrylamide | 0.76 LC-MS 1TFA | 577.4 |
| 88 | (E)-N-(1-Cyclopentyl-piperidin-4-yl)-N-[4-(6-methoxy-quinolin-4-ylamino)-benzyl]-3-(4-trifluoromethyl-phenyl)-acrylamide | 0.81 LC-MS 1TFA | 629.5 |
| 89 | (E)-N-[4-(2,8-Bis-trifluoromethyl-quinolin-4-ylamino)-benzyl]-N-(1-cyclopentyl-piperidin-4-yl)-3-(4-trifluoromethyl-phenyl)-acrylamide | 1.20 LC-MS 1TFA | 735.5 |
| 90 | (E)-N-(1-Cyclopentyl-piperidin-4-yl)-3-(4-trifluoromethyl-phenyl)-N-[4-(7-trifluoromethyl-quinolin-4-ylamino)-benzyl]-acrylamide | 0.84 LC-MS 1TFA | 667.5 |

TABLE 7-continued

| Example | Compound of Formula I | $t_R$ [min] LC-MS Method | MS-data m/z [M + H]$^+$ |
|---|---|---|---|
| 91 | (E)-N-(1-Cyclopentyl-piperidin-4-yl)-N-[4-(pyrimidin-5-ylamino)-benzyl]-3-(4-trifluoromethyl-phenyl)-acrylamide | 0.86 LC-MS 1TFA | 550.4 |
| 92 | (E)-N-(1-Cyclopentyl-piperidin-4-yl)-N-[4-(pyrimidin-4-ylamino)-benzyl]-3-(4-trifluoromethyl-phenyl)-acrylamide | 0.73 LC-MS 1TFA | 550.4 |
| 93 | (E)-N-(1-Cyclopentyl-piperidin-4-yl)-N-(4-phenylamino-benzyl)-3-(4-trifluoromethyl-phenyl)-acrylamide | 1.07 LC-MS 1TFA | 548.4 |
| 94 | (E)-N-(1-Cyclopentyl-piperidin-4-yl)-N-[4-(2-methoxy-pyridin-4-ylamino)-benzyl]-3-(4-trifluoromethyl-phenyl)-acrylamide | 0.75 LC-MS 1TFA | 579.5 |
| 95 | (E)-N-(1-Cyclopentyl-piperidin-4-yl)-N-[4-(2-methyl-pyridin-4-ylamino)-benzyl]-3-(4-trifluoromethyl-phenyl)-acrylamide | 0.75 LC-MS 1TFA | 563.3 |
| 96 | (E)-N-(1-Cyclopentyl-piperidin-4-yl)-N-[4-(methyl-pyridin-3-yl-amino)-benzyl]-3-(4-trifluoromethyl-phenyl)-acrylamide | 0.76 LC-MS 1TFA | 563.4 |
| 97 | (E)-N-[4-(7-Chloro-quinolin-4-ylamino)-benzyl]-N-(1-cyclopentyl-piperidin-4-yl)-3-(4-trifluoromethyl-phenyl)-acrylamide | 0.81 LC-MS 1TFA | 633.5 |
| 98 | (E)-N-(1-Cyclopentyl-piperidin-4-yl)-N-[4-(5-methyl-pyridin-2-ylamino)-benzyl]-3-(4-trifluoromethyl-phenyl)-acrylamide | 0.78 LC-MS 1TFA | 563.5 |
| 99 | (±)-(E)-N-(1-Cyclopentyl-pyrrolidin-3-yl)-N-[4-(methyl-pyridin-4-yl-amino)-benzyl]-3-(4-trifluoromethyl-phenyl)-acrylamide | 0.78 LC-MS 1TFA | 549.5 |
| 100 | (E)-N-(1-Cyclopentyl-piperidin-4-yl)-N-[4-(6-methoxy-2-methyl-quinolin-4-ylamino)-benzyl]-3-(4-trifluoromethyl-phenyl)-acrylamide | 0.82 LC-MS 1TFA | 643.5 |
| 101 | (±)-(E)-N-(1-Cyclopentyl-pyrrolidin-3-yl)-N-[4-(2-methyl-pyridin-4-ylamino)-benzyl]-3-(4-trifluoromethyl-phenyl)-acrylamide | 0.78 LC-MS 1TFA | 549.5 |
| 102 | (E)-N-(1-Cyclopentyl-azetidin-3-yl)-N-[4-(methyl-pyridin-4-yl-amino)-benzyl]-3-(4-trifluoromethyl-phenyl)-acrylamide | 0.76 LC-MS 1TFA | 535.3 |

Method B: A solution of (E)-N-(6-bromo-pyridin-3-ylmethyl)-N-(1-cyclopentyl-piperidin-4-yl)-3-(4-trifluoromethyl-phenyl)-acrylamide (100 mg, 0.19 mmol, 1.00 eq.), sodium tert-butoxide (22 mg, 0.23 mmol, 1.25 eq.) and 4-aminopyridine (18 mg, 0.19 mmol, 1.00 eq.) in dioxane (1.5 mL) was degased with $N_2$ for 15 min before the addition of X-Phos (9 mg, 0.02 mmol, 0.10 eq) and tris(dibenzylideneacetone)dipalladium(0) (8.5 mg, 0.01 mmol, 0.05 eq). The reaction mixture was degased again with $N_2$ for 15 min and then stirred at 105° C. for 18 hours. The reaction was allowed to cool down to r.t. and filtered through Celite. The filtrate was concentrated in vacuo. The residue was purified by prep. HPLC (column: Waters X-Bridge, 30×75 mm, 10 µm, UV/MS, basic conditions) and concentrated in vacuo.

Listed in Table 8 below are examples of compounds of Formula I, prepared according to the above-mentioned method with the corresponding amine 6 and the corresponding bromide of Structure 5 as starting materials.

TABLE 8

| Example | Compound of Formula I | $t_R$ [min] LC-MS Method | MS-data m/z [M + H]$^+$ |
|---|---|---|---|
| 103 | (E)-N-(1-Cyclopentyl-piperidin-4-yl)-N-[6-(pyridin-4-ylamino)-pyridin-3-ylmethyl]-3-(4-trifluoromethyl-phenyl)-acrylamide | 0.72 LC-MS 1TFA | 550.4 |
| 104 | (E)-N-(1-Cyclopentyl-piperidin-4-yl)-N-[6-(methyl-pyridin-4-yl-amino)-pyridin-3-ylmethyl]-3-(4-trifluoromethyl-phenyl)-acrylamide | 0.72 LC-MS 1TFA | 564.4 |
| 105 | (E)-N-(1-Cyclopentyl-piperidin-4-yl)-N-[6-(1-methyl-piperidin-4-ylamino)-pyridin-3-ylmethyl]-3-(4-trifluoromethyl-phenyl)-acrylamide | 0.64 LC-MS 1TFA | 570.4 |
| 106 | (E)-N-(1-Cyclopentyl-piperidin-4-yl)-N-{6-[methyl-(1-methyl-piperidin-4-yl)-amino]-pyridin-3-ylmethyl}-3-(4-trifluoromethyl-phenyl)-acrylamide | 0.64 LC-MS 1TFA | 584.5 |
| 107 | (E)-N-(1-Cyclopentyl-piperidin-4-yl)-N-[6-(pyrimidin-4-ylamino)-pyridin-3-ylmethyl]-3-(4-trifluoromethyl-phenyl)-acrylamide | 0.71 LC-MS 1TFA | 551.4 |
| 108 | (E)-N-(1-Cyclopentyl-piperidin-4-yl)-N-[6-(2-methyl-pyrimidin-4-ylamino)-pyridin-3-ylmethyl]-3-(4-trifluoromethyl-phenyl)-acrylamide | 0.72 LC-MS 1TFA | 565.4 |
| 109 | (E)-N-(1-Cyclopentyl-piperidin-4-yl)-N-[6-(6-methyl-pyrimidin-4-ylamino)-pyridin-3-ylmethyl]-3-(4-trifluoromethyl-phenyl)-acrylamide | 0.72 LC-MS 1TFA | 565.4 |
| 110 | (E)-N-(1'-Methyl-[1,4']bipiperidinyl-4-yl)-N-[6-(pyridin-4-ylamino)-pyridin-3-ylmethyl]-3-(4-trifluoromethyl-phenyl)-acrylamide | 0.61 LC-MS 1TFA | 579.4 |
| 111 | (E)-N-(1'-Methyl-[1,4']bipiperidinyl-4-yl)-N-[6-(2-methyl-pyridin-4-ylamino)-pyridin-3-ylmethyl]-3-(4-trifluoromethyl-phenyl)-acrylamide | 0.63 LC-MS 1TFA | 593.5 |
| 112 | (E)-N-(1'-Methyl-[1,4']bipiperidinyl-4-yl)-N-[6-(methyl-pyridin-4-yl-amino)-pyridin-3-ylmethyl]-3-(4-trifluoromethyl-phenyl)-acrylamide | 0.60 LC-MS 1TFA | 593.6 |

TABLE 8-continued

| Example | Compound of Formula I | $t_R$ [min] LC-MS Method | MS-data m/z [M + H]$^+$ |
|---|---|---|---|
| 113 | (E)-N-((R)-1-Cyclopentyl-pyrrolidin-3-yl)-N-[4-(methyl-pyridin-4-yl-amino)-benzyl]-3-(4-trifluoromethyl-phenyl)-acrylamide | 0.78 LC-MS 1TFA | 549.4 |
| 114 | (E)-N-((S)-1-Cyclopentyl-pyrrolidin-3-yl)-N-[4-(methyl-pyridin-4-yl-amino)-benzyl]-3-(4-trifluoromethyl-phenyl)-acrylamide | 0.78 LC-MS 1TFA | 549.4 |
| 115 | (E)-N-(1'-Methyl-[1,4']bipiperidinyl-4-yl)-N-[4-(pyridin-4-ylamino)-benzyl]-3-(4-trifluoromethyl-phenyl)-acrylamide | 0.60 LC-MS 1TFA | 578.4 |
| 116 | (E)-N-(1'-Methyl-[1,4']bipiperidinyl-4-yl)-N-[4-(2-methyl-pyridin-4-ylamino)-benzyl]-3-(4-trifluoromethyl-phenyl)-acrylamide | 0.84 LC-MS 3 | 592.1 |
| 117 | (E)-3-(4-Chloro-phenyl)-N-(1'-methyl-[1,4']bipiperidinyl-4-yl)-N-[4-(2-methyl-pyridin-4-ylamino)-benzyl]-acrylamide | 0.60 LC-MS 1TFA | 558.4 |
| 118 | (E)-N-(1'-Methyl-[1,4']bipiperidinyl-4-yl)-N-[4-(pyridin-4-ylamino)-benzyl]-3-(4-trifluoromethoxy-phenyl)-acrylamide | 0.64 LC-MS 1TFA | 594.5 |
| 119 | (E)-N-(1'-Methyl-[1,4']bipiperidinyl-4-yl)-N-[4-(2-methyl-pyridin-4-ylamino)-benzyl]-3-(4-trifluoromethoxy-phenyl)-acrylamide | 0.66 LC-MS 1TFA | 608.6 |
| 120 | (E)-N-((S)-1-Isopropyl-piperidin-3-yl)-N-[6-(2-methyl-pyridin-4-ylamino)-pyridin-3-ylmethyl]-3-(4-trifluoromethyl-phenyl)-acrylamide | 0.71 LC-MS 1TFA | 538.4 |

Method C: To a solution under Ar of (E)-N-(3-bromo-benzyl)-N-(1-isopropyl-piperidin-4-yl)-3-(4-trifluoromethyl-phenyl)-acrylamide (51 mg, 0.10 mmol, 1.00 eq.) and methyl-(2-methyl-pyridin-4-yl)-amine (15 mg, 0.12 mmol, 1.2 eq.) in dioxane (1 mL), tris(dibenzylidenaceton)-dipalladium(0) (4.6 mg, 0.005 mmol, 0.05 eq.), X-Phos (4.8 mg, 0.01 mmol, 0.10 eq.), and tBuONa (14 mg, 0.14 mmol, 1.40 eq.) were added in sequence. The mixture was stirred at 105° C. for 3 hours and further at r.t. for 18 hours. The mixture was filtered through neutral alumina and the filtrate was concentrated in vacuo. The residue was purified by prep. HPLC (column: Waters X-Bridge, 30×75 mm, 10 μm, UV/MS, acidic conditions) and concentrated in vacuo.

Listed in Table 9 below are examples of compounds of Formula I, prepared according to the above-mentioned method with the corresponding amine 6 and the corresponding bromide of Structure 5 as starting materials.

TABLE 9

| Example | Compound of Formula I | $t_R$ [min] LC-MS Method | MS-data m/z [M + H]$^+$ |
|---|---|---|---|
| 121 | (E)-N-(1-Isopropyl-piperidin-4-yl)-N-{3-[methyl-(2-methyl-pyridin-4-yl)-amino]-benzyl}-3-(4-trifluoromethyl-phenyl)-acrylamide formate | 0.74 LC-MS 1TFA | 551.5 |
| 122 | (E)-N-(1-Isopropyl-piperidin-4-yl)-N-[3-(2-methyl-pyridin-4-ylamino)-benzyl]-3-(4-trifluoromethyl-phenyl)-acrylamide formate | 0.72 LC-MS 1TFA | 537.4 |
| 123 | (E)-N-(1-Isopropyl-piperidin-4-yl)-N-[3-(3-methyl-pyridin-4-ylamino)-benzyl]-3-(4-trifluoromethyl-phenyl)-acrylamide formate | 0.72 LC-MS 1TFA | 537.4 |
| 124 | (E)-N-[3-(3-Fluoro-pyridin-4-ylamino)-benzyl]-N-(1-isopropyl-piperidin-4-yl)-3-(4-trifluoromethyl-phenyl)-acrylamide formate | 0.71 LC-MS 1TFA | 541.4 |
| 125 | (E)-N-(1-Isopropyl-piperidin-4-yl)-N-[3-(pyrimidin-4-ylamino)-benzyl]-3-(4-trifluoromethyl-phenyl)-acrylamide formate | 0.70 LC-MS 1TFA | 524.4 |
| 126 | (E)-N-(1-Isopropyl-piperidin-4-yl)-N-[3-(pyridin-4-ylamino)-benzyl]-3-(4-trifluoromethyl-phenyl)-acrylamide formate | 0.71 LC-MS 1TFA | 523.4 |
| 127 | (E)-N-(1-Isopropyl-piperidin-4-yl)-N-[6-(methyl-pyridin-4-yl-amino)-pyridin-2-ylmethyl]-3-(4-trifluoromethyl-phenyl)-acrylamide formate | 0.69 LC-MS 1TFA | 538.4 |
| 128 | (E)-N-(1-Isopropyl-piperidin-4-yl)-N-{6-[methyl-(2-methyl-pyridin-4-yl)-amino]-pyridin-2-ylmethyl}-3-(4-trifluoromethyl-phenyl)-acrylamide formate | 0.71 LC-MS 1TFA | 552.4 |
| 129 | (E)-N-(1-Isopropyl-piperidin-4-yl)-N-[6-(2-methyl-pyridin-4-ylamino)-pyridin-2-ylmethyl]-3-(4-trifluoromethyl-phenyl)-acrylamide formate | 0.71 LC-MS 1TFA | 538.4 |
| 130 | (E)-N-(1-Isopropyl-piperidin-4-yl)-N-[6-(3-methyl-pyridin-4-ylamino)-pyridin-2-ylmethyl]-3-(4-trifluoromethyl-phenyl)-acrylamide formate | 0.70 LC-MS 1TFA | 538.5 |
| 131 | (E)-N-[6-(3-Fluoro-pyridin-4-ylamino)-pyridin-2-ylmethyl]-N-(1-isopropyl-piperidin-4-yl)-3-(4-trifluoromethyl-phenyl)-acrylamide formate | 0.69 LC-MS 1TFA | 542.4 |
| 132 | (E)-N-(1-Isopropyl-piperidin-4-yl)-N-[6-(pyridin-4-ylamino)-pyridin-2-ylmethyl]-3-(4-trifluoromethyl-phenyl)-acrylamide formate | 0.69 LC-MS 1TFA | 524.4 |
| 133 | (E)-N-(1-Isopropyl-piperidin-4-yl)-N-[5-(methyl-pyridin-4-yl-amino)-pyridin-3-ylmethyl]-3-(4-trifluoromethyl-phenyl)-acrylamide formate | 0.66 LC-MS 1TFA | 538.4 |

TABLE 9-continued

| Example | Compound of Formula I | $t_R$ [min] LC-MS Method | MS-data m/z [M + H]$^+$ |
|---|---|---|---|
| 134 | (E)-N-(1-Isopropyl-piperidin-4-yl)-N-[5-(methyl-pyridin-3-yl-amino)-pyridin-3-ylmethyl]-3-(4-trifluoromethyl-phenyl)-acrylamide formate | 0.66 LC-MS 1TFA | 538.4 |
| 135 | (E)-N-(1-Isopropyl-piperidin-4-yl)-N-{5-[methyl-(2-methyl-pyridin-4-yl)-amino]-pyridin-3-ylmethyl}-3-(4-trifluoromethyl-phenyl)-acrylamide formate | 0.67 LC-MS 1TFA | 552.4 |
| 136 | (E)-N-(1-Isopropyl-piperidin-4-yl)-N-[5-(2-methyl-pyridin-4-ylamino)-pyridin-3-ylmethyl]-3-(4-trifluoromethyl-phenyl)-acrylamide formate | 0.65 LC-MS 1TFA | 538.4 |
| 137 | (E)-N-(1-Isopropyl-piperidin-4-yl)-N-[5-(3-methyl-pyridin-4-ylamino)-pyridin-3-ylmethyl]-3-(4-trifluoromethyl-phenyl)-acrylamide formate | 0.65 LC-MS 1TFA | 538.4 |
| 138 | (E)-N-[5-(3-Fluoro-pyridin-4-ylamino)-pyridin-3-ylmethyl]-N-(1-isopropyl-piperidin-4-yl)-3-(4-trifluoromethyl-phenyl)-acrylamide formate | 0.65 LC-MS 1TFA | 542.4 |
| 139 | (E)-N-(1-Isopropyl-piperidin-4-yl)-N-[5-(pyrimidin-4-ylamino)-pyridin-3-ylmethyl]-3-(4-trifluoromethyl-phenyl)-acrylamide formate | 0.64 LC-MS 1TFA | 525.4 |
| 140 | (E)-N-(1-Isopropyl-piperidin-4-yl)-N-[5-(methyl-pyridin-2-yl-amino)-pyridin-3-ylmethyl]-3-(4-trifluoromethyl-phenyl)-acrylamide formate | 0.71 LC-MS 1TFA | 538.4 |
| 141 | (E)-N-(1-Isopropyl-piperidin-4-yl)-N-[5-(pyridin-4-ylamino)-pyridin-3-ylmethyl]-3-(4-trifluoromethyl-phenyl)-acrylamide formate | 0.64 LC-MS 1TFA | 524.4 |
| 142 | (E)-N-(1-Isopropyl-piperidin-4-yl)-N-[3-(methyl-pyridin-4-yl-amino)-benzyl]-3-(4-trifluoromethyl-phenyl)-acrylamide formate | 0.72 LC-MS 1TFA | 537.4 |

Amide Coupling

Method A: To a solution of (2E)-3-[4-(propan-2-yloxy)phenyl]prop-2-enoic acid (21 mg, 0.10 mmol, 1.0 eq.), {4-[(1-benzyl-piperidin-4-ylamino)-methyl]-phenyl}-methyl-pyridin-4-yl-amine (39 mg, 0.10 mmol, 1.0 eq.), and HOAT (16 mg, 0.12 mmol, 1.2 eq.) in DMF (1 mL), Si-DCC (300 mg, 0.30 mmol, 3.0 eq.) was added. The reaction was stirred at 50° C. for 4 hours. The mixture was allowed to cool down to r.t. and PI—HCO$_3$ (97 mg, 0.20 mmol, 2.0 eq.) and PI-DETA (38 mg, 0.30 mmol, 3.0 eq.) were added. The mixture was stirred at r.t. for 2 hours, then filtered. The solids were rinsed with DCM/MeOH 1:1. The filtrate was concentrated in vacuo and the residue was purified by prep. HPLC (column: Waters X-bridge, 30×75 mm, 10 μm, UV/MS, basic conditions) and concentrated in vacuo.

Listed in Table 10 below are examples of compounds of Formula I, prepared according to the above-mentioned method with the corresponding amine of Structure 1 and the corresponding acid 2 as starting materials.

TABLE 10

| Example | Compound of Formula I | $t_R$ [min] LC-MS Method | MS-data m/z [M + H]$^+$ |
|---|---|---|---|
| 143 | (E)-N-(1-Benzyl-piperidin-4-yl)-3-(4-isopropoxy-phenyl)-N-[4-(methyl-pyridin-4-yl-amino)-benzyl]-acrylamide | 0.77 LC-MS 1TFA | 575.5 |
| 144 | (E)-N-(1-Benzyl-piperidin-4-yl)-3-(4-tert-butyl-phenyl)-N-[4-(methyl-pyridin-4-yl-amino)-benzyl]-acrylamide | 0.85 LC-MS 1TFA | 573.5 |
| 145 | (E)-N-(1-Benzyl-piperidin-4-yl)-3-(4-difluoromethoxy-phenyl)-N-[4-(methyl-pyridin-4-yl-amino)-benzyl]-acrylamide | 0.72 LC-MS 1TFA | 583.4 |
| 146 | (E)-N-(1-Benzyl-piperidin-4-yl)-N-[4-(methyl-pyridin-4-yl-amino)-benzyl]-3-(4-trifluoromethoxy-phenyl)-acrylamide | 0.80 LC-MS 1TFA | 601.4 |
| 147 | (E)-N-(1-Benzyl-piperidin-4-yl)-3-(4-ethyl-phenyl)-N-[4-(methyl-pyridin-4-yl-amino)-benzyl]-acrylamide | 0.77 LC-MS 1TFA | 545.3 |
| 148 | (E)-N-(1-Benzyl-piperidin-4-yl)-N-[4-(methyl-pyridin-4-yl-amino)-benzyl]-3-(4-propoxy-phenyl)-acrylamide | 0.79 LC-MS 1TFA | 575.5 |
| 149 | (E)-N-(1-Benzyl-piperidin-4-yl)-3-(4-methoxy-phenyl)-N-[4-(methyl-pyridin-4-yl-amino)-benzyl]-acrylamide | 0.68 LC-MS 1TFA | 547.5 |
| 150 | (E)-N-(1-Benzyl-piperidin-4-yl)-3-(3-methoxy-phenyl)-N-[4-(methyl-pyridin-4-yl-amino)-benzyl]-acrylamide | 0.69 LC-MS 1TFA | 547.5 |
| 151 | (E)-N-(1-Benzyl-piperidin-4-yl)-3-(2-methoxy-phenyl)-N-[4-(methyl-pyridin-4-yl-amino)-benzyl]-acrylamide | 0.69 LC-MS 1TFA | 547.5 |
| 152 | (E)-N-(1-Benzyl-piperidin-4-yl)-3-(4-chloro-phenyl)-N-[4-(methyl-pyridin-4-yl-amino)-benzyl]-acrylamide | 0.74 LC-MS 1TFA | 551.4 |
| 153 | (E)-N-(1-Benzyl-piperidin-4-yl)-3-(3-chloro-phenyl)-N-[4-(methyl-pyridin-4-yl-amino)-benzyl]-acrylamide | 0.74 LC-MS 1TFA | 551.4 |
| 154 | (E)-N-(1-Benzyl-piperidin-4-yl)-3-(2-chloro-phenyl)-N-[4-(methyl-pyridin-4-yl-amino)-benzyl]-acrylamide | 0.72 LC-MS 1TFA | 551.4 |
| 155 | (E)-N-(1-Benzyl-piperidin-4-yl)-3-(4-fluoro-phenyl)-N-[4-(methyl-pyridin-4-yl-amino)-benzyl]-acrylamide | 0.69 LC-MS 1TFA | 535.4 |
| 156 | (E)-N-(1-Benzyl-piperidin-4-yl)-3-(3-fluoro-phenyl)-N-[4-(methyl-pyridin-4-yl-amino)-benzyl]-acrylamide | 0.69 LC-MS 1TFA | 535.4 |

TABLE 10-continued

| Example | Compound of Formula I | $t_R$ [min] LC-MS Method | MS-data m/z [M + H]$^+$ |
|---|---|---|---|
| 157 | (E)-N-(1-Benzyl-piperidin-4-yl)-3-(2-fluoro-phenyl)-N-[4-(methyl-pyridin-4-yl-amino)-benzyl]-acrylamide | 0.69 LC-MS 1TFA | 535.4 |
| 158 | (E)-N-(1-Benzyl-piperidin-4-yl)-N-[4-(methyl-pyridin-4-yl-amino)-benzyl]-3-p-tolyl-acrylamide | 0.53 LC-MS 1TFA | 531.4 |
| 159 | (E)-N-(1-Benzyl-piperidin-4-yl)-N-[4-(methyl-pyridin-4-yl-amino)-benzyl]-3-m-tolyl-acrylamide | 0.72 LC-MS 1TFA | 531.4 |
| 160 | (E)-N-(1-Benzyl-piperidin-4-yl)-N-[4-(methyl-pyridin-4-yl-amino)-benzyl]-3-o-tolyl-acrylamide | 0.71 LC-MS 1TFA | 531.4 |
| 161 | (E)-N-(1-Benzyl-piperidin-4-yl)-N-[4-(methyl-pyridin-4-yl-amino)-benzyl]-3-(6-trifluoromethyl-pyridin-3-yl)-acrylamide | 0.69 LC-MS 1TFA | 586.5 |
| 162 | (E)-N-(1-Benzyl-piperidin-4-yl)-3-(4-methanesulfonyl-phenyl)-N-[4-(methyl-pyridin-4-yl-amino)-benzyl]-acrylamide | 0.59 LC-MS 1TFA | 595.4 |
| 163 | (E)-N-(1-Benzyl-piperidin-4-yl)-3-(2,4-dimethyl-thiazol-5-yl)-N-[4-(methyl-pyridin-4-yl-amino)-benzyl]-acrylamide | 0.59 LC-MS 1TFA | 552.4 |
| 164 | (E)-N-(1-Benzyl-piperidin-4-yl)-3-(1,5-dimethyl-1H-pyrazol-4-yl)-N-[4-(methyl-pyridin-4-yl-amino)-benzyl]-acrylamide | 0.57 LC-MS 1TFA | 535.4 |
| 165 | (E)-N-(1-Benzyl-piperidin-4-yl)-N-[4-(methyl-pyridin-4-yl-amino)-benzyl]-3-(1,3,5-trimethyl-1H-pyrazol-4-yl)-acrylamide | 0.58 LC-MS 1TFA | 549.6 |

Method B: To a suspension of 4-(trifluoromethyl)cinnamic acid (40 mg, 0.18 mmol, 1.0 eq.) in DMF (1 mL), DIPEA (95 µL, 0.55 mmol, 3.0 eq.) and TBTU (71 mg, 0.22 mmol, 1.2 eq.) were added in sequence. The resulting solution was stirred at r.t. for 30 min. A solution of N,N-dimethyl-N'-[4-(2-methyl-pyridin-4-ylamino)-benzyl]-propane-1,3-diamine (55 mg, 0.18 mmol, 1.0 eq.) in DMF (1 mL) was added and the resulting mixture was stirred at r.t. for 18 hours. The reaction mixture was purified by prep. HPLC (column: Waters X-Bridge, 30×75 mm, 10 µm, UV/MS, basic conditions) and concentrated in vacuo.

Listed in Table 11 below are examples of compounds of Formula I, prepared according to the above-mentioned method with the corresponding amine of Structure 1 and the corresponding acid 2 as starting materials.

TABLE 11

| Example | Compound of Formula I | $t_R$ [min] LC-MS Method | MS-data m/z [M + H]$^+$ |
|---|---|---|---|
| 166 | (E)-N-(3-Dimethylamino-propyl)-N-[4-(2-methyl-pyridin-4-ylamino)-benzyl]-3-(4-trifluoromethyl-phenyl)-acrylamide | 0.69 LC-MS 1TFA | 497.3 |
| 167 | (E)-3-(4-Chloro-phenyl)-N-(3-dimethylamino-propyl)-N-[4-(2-methyl-pyridin-4-ylamino)-benzyl]-acrylamide | 0.65 LC-MS 1TFA | 463.4 |
| 168 | (E)-N-(1-Cyclopentyl-piperidin-4-yl)-N-[6-(2-methyl-pyridin-4-ylamino)-pyridin-3-ylmethyl]-3-(4-trifluoromethyl-phenyl)-acrylamide | 0.74 LC-MS 1TFA | 564.4 |
| 169 | (E)-3-(4-Chloro-phenyl)-N-(1-cyclopentyl-piperidin-4-yl)-N-[6-(2-methyl-pyridin-4-ylamino)-pyridin-3-ylmethyl]-acrylamide | 0.70 LC-MS 1TFA | 530.4 |
| 170 | (E)-N-(1-Cyclopentyl-piperidin-4-yl)-N-[5-(2-methyl-pyridin-4-ylamino)-pyridin-2-ylmethyl]-3-(4-trifluoromethyl-phenyl)-acrylamide | 0.71 LC-MS 1TFA | 564.4 |
| 171 | (E)-3-(4-Chloro-phenyl)-N-(1-cyclopentyl-piperidin-4-yl)-N-[5-(2-methyl-pyridin-4-ylamino)-pyridin-2-ylmethyl]-acrylamide | 0.67 LC-MS 1TFA | 530.4 |
| 172 | (E)-N-(1'-Methyl-[1,4']bipiperidinyl-4-ylmethyl)-N-[4-(2-methyl-pyridin-4-ylamino)-benzyl]-3-(4-trifluoromethyl-phenyl)-acrylamide | 0.63 LC-MS 1TFA | 606.5 |
| 173 | (E)-N-[4-(2-Methyl-pyridin-4-ylamino)-benzyl]-N-(3-morpholin-4-yl-propyl)-3-(4-trifluoromethyl-phenyl)-acrylamide | 0.70 LC-MS 1TFA | 539.4 |
| 174 | (E)-N-(1-Methyl-piperidin-4-yl)-N-[4-(2-methyl-pyridin-4-ylamino)-benzyl]-3-(4-trifluoromethyl-phenyl)-acrylamide | 0.69 LC-MS 1TFA | 509.4 |
| 175 | (E)-N-(4-Hydroxy-1-methyl-piperidin-4-ylmethyl)-N-[4-(2-methyl-pyridin-4-ylamino)-benzyl]-3-(4-trifluoromethyl-phenyl)-acrylamide | 0.68 LC-MS 1TFA | 539.4 |
| 176 | (E)-N-(2-Dimethylamino-ethyl)-N-[4-(2-methyl-pyridin-4-ylamino)-benzyl]-3-(4-trifluoromethyl-phenyl)-acrylamide | 0.69 LC-MS 1TFA | 483.4 |
| 177 | (E)-N-(1-Benzyl-piperidin-4-yl)-N-{4-[methyl-(1-methyl-piperidin-4-yl)-amino]-benzyl}-3-(4-trifluoromethyl-phenyl)-acrylamide | 0.75 LC-MS 1TFA | 605.6 |
| 178 | (E)-N-(1-Benzyl-piperidin-4-yl)-N-{4-[methyl-(1-methyl-piperidin-4-yl)-amino]-benzyl}-3-(4-trifluoromethoxy-phenyl)-acrylamide | 0.77 LC-MS 1TFA | 621.6 |
| 179 | (E)-3-(4-Cyano-phenyl)-N-(1'-methyl-[1,4']bipiperidinyl-4-yl)-N-[4-(methyl-pyridin-4-yl-amino)-benzyl]-acrylamide | 0.51 LC-MS 1TFA | 549.5 |
| 180 | (E)-3-(4-Chloro-phenyl)-N-(1'-methyl-[1,4']bipiperidinyl-4-yl)-N-[4-(methyl-pyridin-4-yl-amino)-benzyl]-acrylamide | 0.60 LC-MS 1TFA | 558.5 |

TABLE 11-continued

| Example | Compound of Formula I | $t_R$ [min] LC-MS Method | MS-data m/z [M + H]⁺ |
|---|---|---|---|
| 181 | (E)-3-(4-Difluoromethoxy-phenyl)-N-(1'-methyl-[1,4']bipiperidinyl-4-yl)-N-[4-(methyl-pyridin-4-yl-amino)-benzyl]-acrylamide | 0.58 LC-MS 1TFA | 590.4 |
| 182 | (E)-N-(1'-Methyl-[1,4']bipiperidinyl-4-yl)-N-[4-(methyl-pyridin-4-yl-amino)-benzyl]-3-phenyl-acrylamide | 0.54 LC-MS 1TFA | 524.4 |
| 183 | (E)-N-(1'-Methyl-[1,4']bipiperidinyl-4-yl)-N-[4-(methyl-pyridin-4-yl-amino)-benzyl]-3-(6-trifluoromethyl-pyridin-3-yl)-acrylamide | 0.55 LC-MS 1TFA | 593.4 |
| 184 | (E)-N-(1-Cyclopentyl-piperidin-4-yl)-N-{4-[methyl-(2-methyl-pyridin-4-yl)-amino]-benzyl}-3-(4-trifluoromethyl-phenyl)-acrylamide | 0.76 LC-MS 1TFA | 577.5 |
| 185 | (E)-N-[4-(3-Diethylaminomethyl-4-hydroxy-phenylamino)-benzyl]-N-(1-methyl-piperidin-4-yl)-3-(4-trifluoromethyl-phenyl)-acrylamide | 0.75 LC-MS 1TFA | 595.5 |
| 186 | (E)-N-(1-Isopropyl-piperidin-4-yl)-N-[4-(2-methyl-pyridin-4-ylamino)-benzyl]-3-(4-trifluoromethyl-phenyl)-acrylamide | 0.70 LC-MS 1TFA | 537.4 |

Method C: To a solution of 4-(trifluoromethyl)cinnamic acid (30 mg, 0.14 mmol, 1.0 eq.) in DCM (1 mL), N-ethyldiisopropylamine (71 μL, 0.42 mmol, 3.0 eq.) and TBTU (45 mg, 0.14 mmol, 1.0 eq.) were added in sequence. The resulting solution was stirred at r.t. for 1 hour. A solution of methyl-(4-{[(1'-methyl-[1,4']bipiperidinyl-4-ylmethyl)-amino]-methyl}-phenyl)-pyridin-4-yl-amine (57 mg, 0.14 mmol, 1.0 eq.) was added and the resulting mixture was stirred at r.t. for 18 hours. The mixture was concentrated in vacuo and the residue was purified by prep. HPLC (column: Waters X-Bridge, 30×75 mm, 10 μm, UV/MS, basic conditions) and concentrated in vacuo.

Listed in Table 12 below are examples of compounds of Formula I, prepared according to the above-mentioned method with the corresponding amine of Structure 1 and the corresponding acid 2 as starting materials.

Example 195

(E)-N-[1-(2-Dimethylamino-ethyl)-piperidin-4-yl]-N-[4-(methyl-pyridin-4-yl-amino)-benzyl]-3-(4-trifluoromethyl-phenyl)-acrylamide formate To a solution of 4-(trifluoromethyl)cinnamic acid (29 mg, 0.13 mmol, 1.0 eq.) in DCM (1.5 mL), N-ethyldiisopropylamine (69 μL, 0.40 mmol, 3.0 eq.) and TBTU (43 mg, 0.13 mmol, 1.0 eq.) were added in sequence. The resulting solution was stirred at r.t. for 1 hour. A solution of (4-{[1-(2-di methylamino-ethyl)-piperidin-4-ylamino]-methyl}-phenyl)-methyl-pyridin-4-yl-amine (49 mg, 0.13 mmol, 1.0 eq.) was added and the resulting mixture was stirred at r.t. for 18 hours. The mixture was concentrated in vacuo and the residue was purified by prep. HPLC (column: Waters X-Bridge, 30×75 mm, 10 μm, UV/MS, acidic conditions) and concentrated in vacuo.

LC-MS 1TFA: $t_R$=0.64 min; [M+H]⁺=566.5

TABLE 12

| Example | Compound of Formula I | $t_R$ [min] LC-MS Method | MS-data m/z [M + H]⁺ |
|---|---|---|---|
| 187 | (E)-N-(1'-Methyl-[1,4']bipiperidinyl-4-ylmethyl)-N-[4-(methyl-pyridin-4-yl-amino)-benzyl]-3-(4-trifluoromethyl-phenyl)-acrylamide | 0.63 LC-MS 1TFA | 606.5 |
| 188 | (E)-N-(1-Cyclopentyl-piperidin-4-ylmethyl)-N-[4-(methyl-pyridin-4-yl-amino)-benzyl]-3-(4-trifluoromethyl-phenyl)-acrylamide | 0.76 LC-MS 1TFA | 577.5 |
| 189 | (E)-N-[1-(3-Methyl-butyl)-piperidin-4-ylmethyl]-N-[4-(methyl-pyridin-4-yl-amino)-benzyl]-3-(4-trifluoromethyl-phenyl)-acrylamide | 0.80 LC-MS 1TFA | 579.5 |
| 190 | (±)-trans-(E)-N-(4-Dimethylamino-cyclohexyl)-N-[4-(methyl-pyridin-4-yl-amino)-benzyl]-3-(4-trifluoromethyl-phenyl)-acrylamide | 0.72 LC-MS 1TFA | 537.5 |
| 191 | (±)-cis-(E)-N-(4-Dimethylamino-cyclohexyl)-N-[4-(methyl-pyridin-4-yl-amino)-benzyl]-3-(4-trifluoromethyl-phenyl)-acrylamide | 0.72 LC-MS 1TFA | 537.4 |
| 192 | (±)-cis-(E)-N-[4-(Methyl-pyridin-4-yl-amino)-benzyl]-N-(4-pyrrolidin-1-yl-cyclohexyl)-3-(4-trifluoromethyl-phenyl)-acrylamide | 0.74 LC-MS 1TFA | 563.4 |
| 193 | (±)-trans-(E)-N-[4-(Methyl-pyridin-4-yl-amino)-benzyl]-N-(4-pyrrolidin-1-yl-cyclohexyl)-3-(4-trifluoromethyl-phenyl)-acrylamide | 0.73 LC-MS 1TFA | 563.5 |
| 194 | (E)-N-(1'-Methyl-[1,4']bipiperidinyl-4-yl)-N-[4-(pyridine-4-carbonyl)-benzyl]-3-(4-trifluoromethyl-phenyl)-acrylamide | 0.73 LC-MS 1TFA | 591.5 |

Suzuki Cross-Coupling

Tetrakis(triphenylphosphine) palladium (0) (10.4 mg, 0.01 mmol, 0.05 eq.) and (E)-N-(4-bromo-benzyl)-N-(1-cyclopentyl-piperidin-4-yl)-3-(4-trifluoromethyl-phenyl)-acrylamide (96 mg, 0.18 mmol, 1.00 eq.) were suspended in acetonitrile (1 mL). The suspension was degased with $N_2$ for 15 min. Then a degased solution of 0.4M aq. $Na_2CO_3$ (2.25 mL, 0.90 mmol, 5.00 eq.) and 2-methylpyridine-4-boronic acid (26 mg, 0.18 mmol, 1.00 eq.) were added in sequence. The reaction mixture was degased with N2 for 5 min. The reaction mixture was stirred at 70° C. for 18 hours. The reaction mixture was allowed to cool to r.t. and filtered through Celite. The filtrate was concentrated and the residue was purified by prep. HPLC (column: Waters X-Bridge, 30×75 mm, 10 μm, UV/MS, basic conditions) and concentrated in vacuo.

Listed in Table 13 below are examples of compounds of Formula I, prepared according to the above-mentioned method with the corresponding boronic acid as starting material.

TABLE 13

| Example | Compound of Formula I | $t_R$ [min] LC-MS Method | MS-data m/z $[M + H]^+$ |
|---|---|---|---|
| 196 | (E)-N-(1-Cyclopentyl-piperidin-4-yl)-N-[4-(2-methyl-pyridin-4-yl)-benzyl]-3-(4-trifluoromethyl-phenyl)-acrylamide | 0.73 LC-MS 1TFA | 548.4 |
| 197 | (E)-N-(1-Cyclopentyl-piperidin-4-yl)-N-(4-pyridin-3-yl-benzyl)-3-(4-trifluoromethyl-phenyl)-acrylamide | 0.75 LC-MS 1TFA | 534.4 |
| 198 | (E)-N-(1-Cyclopentyl-piperidin-4-yl)-N-(4-pyridin-2-yl-benzyl)-3-(4-trifluoromethyl-phenyl)-acrylamide | 0.81 LC-MS 1TFA | 534.4 | resulting mixture was stirred at r.t. for 18 hours. Sat aq. $NaHCO_3$ soln. was added and the resulting mixture was stirred at r.t. for 30 min. The layers were separated and the org. phase was concentrated in vacuo.

To a solution of the residue in DMF (1.5 mL), a solution of 4-(trifluoromethyl)cinnamic acid (43 mg, 0.20 mmol, 1.0 eq.) and 4-(dimethylamino)pyridine (37 mg, 0.30 mmol, 1.5 eq.) in DMF (0.5 mL) was added. EDC (38 mg, 0.20 mmol, 1.0 eq.) was added and the resulting mixture was stirred at r.t. for 60 hours. The mixture was purified by prep. HPLC (column: Waters X-Bridge, 30×75 mm, 10 μm, UV/MS, basic conditions) and concentrated in vacuo.

Listed in Table 14 below are examples of compounds of Formula I, prepared according to the above-mentioned method with the corresponding amine 4 (or the corresponding salt) and the corresponding aldehyde as starting materials.

TABLE 14

| Example | Compound of Formula I | $t_R$ [min] LC-MS Method | MS-data m/z $[M + H]^+$ |
|---|---|---|---|
| 199 | (E)-N-(1-Cyclopentyl-piperidin-4-yl)-N-[4-(4-isopropyl-piperazin-1-yl)-benzyl]-3-(4-trifluoromethyl-phenyl)-acrylamide | 0.75 LC-MS 1TFA | 583.5 |
| 200 | (E)-N-(1-Cyclopentyl-piperidin-4-yl)-N-[4-(4-methyl-piperazin-1-yl)-benzyl]-3-(4-trifluoromethyl-phenyl)-acrylamide | 0.73 LC-MS 1TFA | 555.5 |
| 201 | (E)-N-(1-Cyclopentyl-piperidin-4-yl)-N-[4-(2-methyl-thiazol-5-yl)-benzyl]-3-(4-trifluoromethyl-phenyl)-acrylamide | 0.96 LC-MS 1TFA | 554.4 |
| 202 | (E)-N-(1-Cyclopentyl-piperidin-4-yl)-N-[4-(1-methyl-1H-pyrazol-3-yl)-benzyl]-3-(4-trifluoromethyl-phenyl)-acrylamide | 0.94 LC-MS 1TFA | 537.4 |
| 203 | (E)-N-(1-Cyclopentyl-piperidin-4-yl)-N-(4-pyrimidin-2-yl-benzyl)-3-(4-trifluoromethyl-phenyl)-acrylamide | 0.95 LC-MS 1TFA | 535.4 |
| 204 | (E)-N-(1-Cyclopentyl-piperidin-4-yl)-N-(4-pyrimidin-5-yl-benzyl)-3-(4-trifluoromethyl-phenyl)-acrylamide | 0.88 LC-MS 1TFA | 535.4 |
| 205 | (E)-N-(1-Cyclopentyl-piperidin-4-yl)-N-[4-(3-dimethylamino-propoxy)-benzyl]-3-(4-trifluoromethyl-phenyl)-acrylamide | 0.75 LC-MS 1TFA | 558.5 |
| 206 | (E)-N-(1-Cyclopentyl-piperidin-4-yl)-N-(2-pyrrolidin-1-yl-pyridin-4-ylmethyl)-3-(4-trifluoromethyl-phenyl)-acrylamide | 0.74 LC-MS 1TFA | 527.4 |

Reductive Amination and Subsequent Amide Coupling

Method A: A solution of 1-cyclopentylpiperidin-4-amine hydrochloride (48 mg, 0.20 mmol, 1.0 eq.), 4-(4-isopropylpiperazin-1-yl)benzaldehyde (22 mg, 0.18 mmol, 0.9 eq.), and DIPEA (0.1 mL, 0.60 mmol, 3.0 eq.) in DCM (7 mL) was stirred at r.t. for 10 min before the addition of sodium triacetoxyborohydride (85 mg, 0.40 mmol, 2.0 eq.). The Method B: A solution of 1-cyclopentylpiperidin-4-amine hydrochloride (80 mg, 0.33 mmol, 1.0 eq.), 4-(pyridin-4-yloxy)-benzaldehyde (66 mg, 0.33 mmol, 1.0 eq.), and DIPEA (0.17 mL, 1.00 mmol, 3.0 eq.) in DCM (7 mL) was stirred at r.t. for 10 min before the addition of sodium triacetoxyborohydride (141 mg, 0.66 mmol, 2.0 eq.). The resulting mixture was stirred at r.t. for 18 hours. Sat aq. $NaHCO_3$ soln. was added and the resulting mixture was stirred at r.t. for 30 min. The layers were separated and the org. phase was concentrated in vacuo.

To a solution of 4-(trifluoromethyl)cinnamic acid (72 mg, 0.33 mmol, 1.0 eq.) in DMF (1.0 mL), DIPEA (85 µL, 0.50 mmol, 1.5 eq.) and HATU (151 mg, 0.40 mmol, 1.2 eq.) were added in sequence. The mixture was stirred at r.t. for 15 min. A solution of the previous residue in DMF (1.0 mL) was added and the reaction mixture was stirred at r.t. for 18 hours. The mixture was purified by prep. HPLC (column: Waters X-Bridge, 30×75 mm, 10 µm, UV/MS, basic conditions) and concentrated in vacuo.

Listed in Table 15 below are examples of compounds of Formula I, prepared according to the above-mentioned method with the corresponding amine 4 (or the corresponding salt) and the corresponding aldehyde as starting materials.

TABLE 15

| Example | Compound of Formula I | $t_R$ [min] LC-MS Method | MS-data m/z $[M + H]^+$ |
|---|---|---|---|
| 207 | (E)-N-(1-Cyclopentyl-piperidin-4-yl)-N-[4-(pyridin-4-yloxy)-benzyl]-3-(4-trifluoromethyl-phenyl)-acrylamide | 0.75 LC-MS 1TFA | 550.4 |
| 208 | (E)-N-(1-Cyclopentyl-piperidin-4-yl)-N-[4-(2,6-dimethyl-pyridin-4-yloxy)-benzyl]-3-(4-trifluoromethyl-phenyl)-acrylamide | 0.77 LC-MS 1TFA | 578.5 |

Method C: A solution of 1-dimethylamino-2-propylamine (31 mg, 0.30 mmol, 1.0 eq.), 4-(2-methyl-pyridin-4-ylamino)-benzaldehyde (64 mg, 0.30 mmol, 1.0 eq.), and DIPEA (51 µL, 0.30 mmol, 1.0 eq.) in DCM (2 mL) was stirred at r.t. for 10 min before the addition of sodium triacetoxyborohydride (127 mg, 0.60 mmol, 2.0 eq.). The resulting mixture was stirred at r.t. for 18 hours. Sat aq. NaHCO$_3$ soln. was added and the resulting mixture was stirred at r.t. for 30 min. The layers were separated and the org. phase was concentrated in vacuo.

To a solution of the residue in DMF (1.0 mL), a solution of 4-chlorocinnamic acid (66 mg, 0.36 mmol, 1.2 eq.) and 4-(dimethylamino)pyridine (55 mg, 0.45 mmol, 1.5 eq.) in DMF (1.0 mL) was added. EDC (58 mg, 0.30 mmol, 1.0 eq.) was added and the resulting mixture was stirred at r.t. for 60 hours. The mixture was purified by prep. HPLC (column: Waters X-Bridge, 30×75 mm, 10 µm, UV/MS, basic conditions) and concentrated in vacuo.

Listed in Table 16 below are examples of compounds of Formula I, prepared according to the above-mentioned method with the corresponding amine 4 (or the corresponding salt) and the corresponding aldehyde 3 as starting materials.

TABLE 16

| Example | Compound of Formula I | $t_R$ [min] LC-MS Method | MS-data m/z $[M + H]^+$ |
|---|---|---|---|
| 209 | (E)-3-(4-Chloro-phenyl)-N-(2-dimethylamino-1-methyl-ethyl)-N-[4-(2-methyl-pyridin-4-ylamino)-benzyl]-acrylamide | 0.63 LC-MS 1TFA | 463.3 |
| 210 | (E)-3-(4-Chloro-phenyl)-N-(1-cyclopropyl-piperidin-4-yl)-N-[4-(2-methyl-pyridin-4-ylamino)-benzyl]-acrylamide | 0.68 LC-MS 1TFA | 501.4 |

General Method for the Synthesis of Precursors and Intermediates:

General Method for the Synthesis of an Amine of Structure 1

Method A: To a solution of 1-cyclopentylpiperidin-4-amine hydrochloride (102 mg, 0.50 mmol, 1.0 eq.) in methanol (1 mL), triethylamine (70 µl, 0.50 mmol, 1.0 eq.) and 6-(2-methyl-pyridin-4-ylamino)-pyridine-3-carbaldehyde (107 mg, 0.50 mmol, 1.0 eq.) were added in sequence. The resulting solution was stirred at r.t. for 18 hours. Sodium borohydride (30 mg, 0.75 mmol, 1.5 eq.) was added portionwise and the solution was stirred at r.t. for 1 hour. The resulting mixture was treated with sat. aq. NaHCO₃ sol., stirred for 30 min, and concentrated in vacuo. The residue was purified by prep. HPLC (column: Waters X-Bridge, 30×75 mm, 10 μm, UV/MS, basic conditions) and concentrated in vacuo to give the desired amine of Structure 1.

Listed in Table 17 below are amine of Structure 1, prepared according to the above-mentioned method with the corresponding amine 4 (or the corresponding salt) and the corresponding aldehyde 3 as starting materials.

was cooled to 0° C. and sodium borohydride (89 mg, 2.25 mmol, 1.5 eq.) was added portionwise. The cooling bath was removed and the solution was stirred at r.t. for 1 hour. The resulting reaction mixture was quenched with sat. aq. NaHCO₃ soln. The mixture was extracted with DCM (2×). The comb. org. phases were dried over MgSO₄ and concentrated in vacuo. The residue was purified by flashmaster (column: 50 g, flow: 40 mL/min, 20 fractions of 40 mL from

TABLE 17

| Amine of Structure 1 | $t_R$ [min] LC-MS Method | MS-data m/z $[M + H]^+$ |
|---|---|---|
| 5-(((1-cyclopentylpiperidin-4-yl)amino)methyl)-N-(2-methylpyridin-4-yl)pyridin-2-amine | 0.75 LC-MS 3 | 366.1 |
| 6-(((1-cyclopentylpiperidin-4-yl)amino)methyl)-N-(2-methylpyridin-4-yl)pyridin-3-amine | 0.71 LC-MS 3 | 366.1 |
| {4-[(1-Cyclopentyl-piperidin-4-ylamino)-methyl]-phenyl}-(2-methyl-pyridin-4-yl)-amine | 0.80 LC-MS 3 | 365.2 |
| N,N-Dimethyl-N'-[4-(2-methyl-pyridin-4-ylamino)-benzyl]-propane-1,3-diamine | 0.67 LC-MS 3 | 299.0 |
| {4-[(1-Isopropyl-piperidin-4-ylamino)-methyl]-phenyl}-(2-methyl-pyridin-4-yl)-amine | 0.75 LC-MS 3 | 339.1 |
| (4-{[(1'-Methyl-[1,4']bipiperidinyl-4-ylmethyl)-amino]-methyl}-phenyl)-(2-methyl-pyridin-4-yl)-amine | 0.70 LC-MS 3 | 408.2 |
| (2-Methyl-pyridin-4-yl)-{4-[(3-morpholin-4-yl-propylamino)-methyl]-phenyl}-amine | 0.65 LC-MS 3 | 341.1 |
| {4-[(1-Methyl-piperidin-4-ylamino)-methyl]-phenyl}-(2-methyl-pyridin-4-yl)-amine | 0.67 LC-MS 3 | 311.2 |
| (1-Cyclopentyl-piperidin-4-yl)-[4-(4-methyl-piperazin-1-yl)-benzyl]-amine | 0.80 LC-MS 3 | 357.2 |
| 1-Methyl-4-{[4-(2-methyl-pyridin-4-ylamino)-benzylamino]-methyl}-piperidin-4-ol | 0.62 LC-MS 3 | 341.1 |
| {4-[(1-Cyclopentyl-piperidin-4-ylamino)-methyl]-phenyl}-methyl-(2-methyl-pyridin-4-yl)-amine | 0.85 LC-MS 3 | 379.2 |
| (1'-Methyl-[1,4']bipiperidinyl-4-yl)-{4-[methyl-(2-methyl-pyridin-4-yl)-amino]-benzyl}-amine | 0.74 LC-MS 3 | 408.2 |

Method B: To a solution of 1-cyclopentylpiperidin-4-amine hydrochloride (307 mg, 1.50 mmol, 1.0 eq.) in methanol (4.5 mL), triethylamine (0.21 mL, 1.50 mmol, 1.0 eq.) and 4-(methyl-pyridin-4-yl-amino)-benzaldehyde (318 mg, 1.50 mmol, 1.0 eq.) were added in sequence. The resulting solution was refluxed for 18 hours. The solution AcOEt-NEt₃ (10%) to 92% AcOEt-NEt₃ (10%) with MeOH) to yield the desired amine of Structure 1 as an yellow solid.

Listed in Table 18 below are amine of Structure 1, prepared according to the above-mentioned method with the corresponding amine 4 (or the corresponding salt) and the corresponding aldehyde 3 as starting materials.

TABLE 18

| Amine of Structure 1 | $t_R$ [min] LC-MS Method | MS-data m/z $[M + H]^+$ |
|---|---|---|
| {4-[(1-Cyclopentyl-piperidin-4-ylamino)-methyl]-phenyl}-methyl-pyridin-4-yl-amine | 0.82 LC-MS 3 | 365.2 |
| N-(4-(((1-benzylpiperidin-4-yl)amino)methyl)phenyl)-N,1-dimethylpiperidin-4-amine | 0.88 LC-MS 3 | 407.2 |
| (1'-Methyl-[1,4']bipiperidinyl-4-yl)-[4-(methyl-pyridin-4-yl-amino)-benzyl]-amine | 0.71 LC-MS 3 | 393.9 |
| (4-{[1-(2-Dimethylamino-ethyl)-piperidin-4-ylamino]-methyl}-phenyl)-methyl-pyridin-4-yl-amine | 0.69 LC-MS 3 | 368.3 |
| Methyl-(4-{[(1'-methyl-[1,4']bipiperidinyl-4-ylmethyl)-amino]-methyl}-phenyl)-pyridin-4-yl-amine | 0.72 LC-MS 3 | 408.3 |
| (4-{[(1-Cyclopentyl-piperidin-4-ylmethyl)-amino]-methyl}-phenyl)-methyl-pyridin-4-yl-amine | 0.85 LC-MS 3 | 379.3 |
| Methyl-[4-({[1-(3-methyl-butyl)-piperidin-4-ylmethyl]-amino}-methyl)-phenyl]-pyridin-4-yl-amine | 0.91 LC-MS 3 | 381.3 |
| (±)-trans-N,N-Dimethyl-N'-[4-(methyl-pyridin-4-yl-amino)-benzyl]-cyclohexane-1,4-diamine | 0.33 LC-MS 4 | 339.3 |
| (±)-cis-N,N-Dimethyl-N'-[4-(methyl-pyridin-4-yl-amino)-benzyl]-cyclohexane-1,4-diamine | 0.34 LC-MS 4 | 339.2 |
| (±)-cis-Methyl-pyridin-4-yl-{4-[(4-pyrrolidin-1-yl-cyclohexylamino)-methyl]-phenyl}-amine | 0.37 LC-MS 4 | 365.2 |

TABLE 18-continued

| Amine of Structure 1 | $t_R$ [min] LC-MS Method | MS-data m/z [M + H]$^+$ |
|---|---|---|
| (±)-trans-Methyl-pyridin-4-yl-{4-[(4-pyrrolidin-1-yl-cyclohexylamino)-methyl]-phenyl}-amine | 0.36 LC-MS 4 | 365.3 |

Synthesis of {4-[(1'-Methyl-[1,4']bipiperidinyl-4-ylamino)-methyl]-phenyl}-pyridin-4-yl-methanone To a solution of 1'-methyl-[1,4'-bipiperidin]-4-amine hydrochloride (153 mg, 0.65 mmol, 1.0 eq.) in EtOH (5 mL), NEt$_3$ (0.36 mL, 2.61 mmol, 4.0 eq.) was added. The mixture was stirred for a few minutes before 4-(pyridine-4-carbonyl)-benzaldehyde (138 mg, 0.65 mmol, 1.0 eq.) was added. The resulting solution was stirred at r.t. for 18 hours. Sodium cyanoborohydride (21 mg, 0.33 mmol, 0.5 eq.) was added and the mixture was stirred at r.t. for 18 hours. Sodium cyanoborohydride (21 mg, 0.33 mmol, 0.5 eq) was added again and the reaction was stirred at r.t. for 18 hours. The mixture was concentrated in vacuo. The residue was partitioned between sat. aq. NaHCO$_3$ soln. and DCM. The layers were separated and the aq. phase was extracted with DCM. The comb. org. phases were dried over MgSO$_4$ and concentrated in vacuo to afford the title compound as a pale yellow oil. The product was used without further purification.

LC-MS 3: $t_R$=0.70 min; [M+H]$^+$=393.2

Synthesis of (±)-{4-[(1'-Methyl-[1,4']bipiperidinyl-4-ylamino)-methyl]-phenyl}-pyridin-4-yl-methanol To an ice-cooled solution of {4-[(1'-methyl-[1,4']bipiperidinyl-4-ylamino)-methyl]-phenyl}-pyridin-4-yl-methanone (60 mg, 0.15 mmol, 1.0 eq.) in MeOH (1 mL), NaBH$_4$ (6 mg, 0.15 mmol, 1.0 eq.) was added portionwise. The resulting solution was stirred ar r.t. for 48 hours. NaBH$_4$ (1 mg, 0.03 mmol, 0.2 eq) was added and the mixture was stirred at r.t. for 1 hour. The mixture was concentrated in vacuo. The residue was partitioned between sat. aq. NaHCO$_3$ soln. (1 ml) and DCM. The layers were separated and the aq. phase was extracted with DCM. The comb. org. layers were dried over MgSO$_4$ and concentrated in vacuo. The residue was purified by prep. HPLC (column: Waters X-Bridge, 30×75 mm, 10 lam, UV/MS, basic conditions) and concentrated in vacuo to give the title compound as a white solid.

LC-MS 3: $t_R$=0.66 min; [M+H]$^+$=395.2

Synthesis of {4-[(1-Benzyl-piperidin-4-ylamino)-methyl]-phenyl}-methyl-pyridin-4-yl-amine Step 1: To a solution of 4-brombenzaldehyde (5.55 g, 30.0 mmol, 1.0 eq.) in DCM (100 mL), 4-amino-1-benzyl piperidine (5.71 g, 30.0 mmol, 1.0 eq.) was added. Sodium triacetoxyborohydride (7.63 g, 36.0 mmol, 1.2 eq.) was added portionwise and the reaction mixture was stirred at r.t. for 16 hours. Sat. aq. NaHCO$_3$ soln. (100 mL) was added and the mixture was stirred at r.t. for 2 hours. The layers were separated and the organic phase was dried over MgSO$_4$ and concentrated in vacuo to give (1-benzyl-piperidin-4-yl)-(4-bromo-benzyl)-amine as a colorless oil. The product was used without further purification.

LC-MS 2: $t_R$=0.42 min; [M+H]$^+$=359.1

Step 2: To a solution of (1-benzyl-piperidin-4-yl)-(4-bromo-benzyl)-amine (10.67 g, 29.7 mmol, 1.00 eq.) and triethylamine (6.2 mL, 44.5 mmol, 1.50 eq.) in DCM (100 mL), a solution of di-tert-butyl dicarbonate (7.97 g, 36.5 mmol, 1.22 eq.) in DCM (40 mL) was added under N$_2$. The resulting suspension was stirred at r.t. for 4 hours. The reaction mixture was diluted with water (140 mL). The layers were separated. The aq. phase was extracted with DCM (2×150 mL). The comb. org. phases were washed with water (1×100 mL), sat. aq. NaCl soln. (1×100 mL), dried over MgSO$_4$, and concentrated in vacuo. The residue was purified by flashmaster (column: 340 g, flow: 70 mL/min, Hept. to Hept./AcOEt 1:1) to afford (1-benzyl-piperidin-4-yl)-(4-bromo-benzyl)-carbamic acid tert-butyl ester as a colorless oil.

LC-MS 2: $t_R$=0.77 min; [M+H]$^+$=459.0

Step 3: To a solution of (1-benzyl-piperidin-4-yl)-(4-bromo-benzyl)-carbamic acid tert-butyl ester (459 mg, 1.0 mmol, 1.00 eq.) in dioxane (3 mL), 4-(methylamino)pyridine (108 mg, 1.0 mmol, 1.00 eq.) and sodium tert-butoxide (144 mg, 1.5 mmol, 1.50 eq.) were added. The solution was degased with N$_2$ for 15 min. The solution was heated to 105° C. A solution of the Pd catalyst Solvias SK-0002-A (31 mg, 0.05 mmol, 0.05 eq.) in dioxane (2.5 mL), previously degased with N$_2$, was added to the hot reaction mixture. The reaction was stirred at 105° C. for 18 hours. The reaction mixture was filtered through Celite and the filtrate concentrated in vacuo. The residue was purified by flashmaster (column: 50 g, flow: 40 mL/min, 60 fractions of 15 mL, Hept/AcOEt/NEt$_3$ (10% NEt$_3$) 80:20 to AcOEt/NEt$_3$ (10% NEt$_3$)) to afford (1-benzyl-piperidin-4-yl)-[4-(methyl-pyridin-4-yl-amino)-benzyl]-carbamic acid tert-butyl ester as a brown gum.

LC-MS 3: $t_R$=1.04 min; [M+H]$^+$=487.0

Step 4: To an ice-cooled solution of (1-benzyl-piperidin-4-yl)-[4-(methyl-pyridin-4-yl-amino)-benzyl]-carbamic acid tert-butyl ester (3.29 g, 6.76 mmol, 1 eq.) in DCM (50 mL), 4M HCl in dioxane (18 mL) was added. The resulting solution was stirred at r.t. for 3 hours. The reaction mixture was poured in 1M aq. NaOH soln. and extracted with DCM (3×). The comb. org. phases were dried over MgSO$_4$, filtered, and concentrated in vacuo to afford the title compound as a brown solid. The product was used without further purification.

LC-MS 3: $t_R$=0.84 min; [M+H]$^+$=387.1

General Method for the Synthesis of a Bromide of Structure 5

Step 1: To a solution of (S)-1-cyclopentylpyrrolidin-3-amine hydrochloride (1.36 g, 5.99 mmol, 1.0 eq.) in MeOH (12 mL), triethylamine (0.83 mL, 5.99 mmol, 1.0 eq.) and 4-bromobenzaldehyde (1.11 g, 5.99 mmol, 1.0 eq.) were added in sequence. The resulting solution was refluxed for 4 hours. The solution was cooled to 0° C. and sodium borohydride (354 mg, 8.98 mmol, 1.5 eq.) was added portionwise. The cooling bath was removed and the solution was stirred at r.t. for 1 hour. The resulting reaction mixture was quenched with sat. aq. NaHCO$_3$ solution. The mixture was extracted with DCM (2×). The comb. org. phases were dried over MgSO$_4$, and concentrated in vacuo. The residue was purified by flashmaster (column: 100 g, flow: 45 mL/min, 30 fractions of 45 mL, AcOEt/NEt$_3$ (10% NEt$_3$) to MeOH 4%/AcOEt/NEt₃ (10% NEt₃)) to yield (4-bromo-benzyl)-((S)-1-cyclopentyl-pyrrolidin-3-yl)-amine as an yellow oil.

LC-MS 3: $t_R$=0.93 min; [M+H]⁺=323.0

Step 2: To a solution of 4-(trifluoromethyl)cinnamic acid (134 mg, 0.62 mmol, 1.0 eq.) in DCM (2.0 mL), N-ethyldiisopropylamine (0.32 mL, 1.83 mmol, 3.0 eq.) and TBTU (199 mg, 0.62 mmol, 1.0 eq.) were added in sequence. The resulting solution was stirred at r.t. for 30 minutes. Then a solution of (4-bromo-benzyl)-((S)-1-cyclopentyl-pyrrolidin-3-yl)-amine (200 mg, 0.62 mmol, 1.0 eq.) in DCM (2.0 mL) was added and the resulting mixture was stirred at r.t. for 2 days. The mixture was evaporated. The residue was purified by prep. HPLC (column: Waters X-Bridge, 30×75 mm, 10 μm, UV/MS, basic conditions) and concentrated in vacuo to give the desired bromide of Structure 5.

Listed in Table 19 below are bromide of Structure 5, prepared according to the above-mentioned method with the corresponding amine 4 (or the corresponding salt) as starting material.

cyclopentylpiperidin-4-amine as a light yellow oil. The product was used without further purification.

LC-MS 3: $t_R$=0.96 min; [M+H]⁺=337.0

Step 2: To a solution of N-(4-bromobenzyl)-1-cyclopentylpiperidin-4-amine (3.71 g, 11.0 mmol, 1.0 eq.) and 4-(trifluoromethyl)cinnamic acid (2.39 g, 11.0 mmol, 1.0 eq.) in DMF (25 mL), EDC (3.17 g, 16.6 mmol, 1.5 eq.) and 4-(dimethylamino)pyridine (2.02 g, 16.6 mmol, 1.5 eq.) were added in sequence. The mixture was stirred at r.t. for 18 hours. The mixture was diluted with AcOEt. The diluted solution was washed with sat. aq. NaHCO₃ soln. (3×), sat. aq. NaCl soln., dried over MgSO₄, and concentrated in vacuo. The residue was purified by flashmaster (column: 340 g, flow: 90 mL/min, 80 fractions of 45 ml, Hept/AcOEt/NEt₃ (10% NEt₃) 80:20 to AcOEt/NEt₃ (10% NEt₃)) to afford the title compound as an brown foam.

LC-MS 2: $t_R$=0.78 min; [M+H]⁺=535.3

TABLE 19

| Bromide of Structure 5 | $t_R$ [min] LC-MS Method | MS-data m/z [M + H]⁺ |
|---|---|---|
| (E)-N-(4-Bromo-benzyl)-N-((S)-1-cyclopentyl-pyrrolidin-3-yl)-3-(4-trifluoromethyl-phenyl)-acrylamide | 1.16 LC-MS 3 | 520.8 |
| (±)-(E)-N-(4-Bromo-benzyl)-N-(1-cyclopentyl-pyrrolidin-3-yl)-3-(4-trifluoromethyl-phenyl)-acrylamide | 1.16 LC-MS 3 | 520.8 |
| (E)-N-(4-Bromo-benzyl)-N-((R)-1-cyclopentyl-pyrrolidin-3-yl)-3-(4-trifluoromethyl-phenyl)-acrylamide | 1.16 LC-MS 3 | 520.8 |
| (E)-N-(4-Bromo-benzyl)-N-(1'-methyl-[1,4']bipiperidinyl-4-yl)-3-(4-trifluoromethoxy-phenyl)-acrylamide | 0.99 LC-MS 3 | 580.0 |
| (E)-N-(4-Bromo-benzyl)-N-(1'-methyl-[1,4']bipiperidinyl-4-yl)-3-(4-trifluoromethyl-phenyl)-acrylamide | 0.98 LC-MS 3 | 564.0 |
| (E)-N-(4-Bromo-benzyl)-3-(4-chloro-phenyl)-N-(1'-methyl-[1,4']bipiperidinyl-4-yl)-acrylamide | 0.97 LC-MS 3 | 529.9 |
| (E)-N-(6-Bromo-pyridin-3-ylmethyl)-N-(1-cyclopentyl-piperidin-4-yl)-3-(4-trifluoromethyl-phenyl)-acrylamide | 1.03 LC-MS 3 | 536.0 |
| (E)-N-(4-Bromo-benzyl)-N-(1-methyl-piperidin-4-yl)-3-(4-trifluoromethyl-phenyl)-acrylamide | 0.99 LC-MS 3 | 480.9 |
| (E)-N-(3-Bromo-benzyl)-N-(1-isopropyl-piperidin-4-yl)-3-(4-trifluoromethyl-phenyl)-acrylamide | 0.80 LC-MS 4 | 509.1 |
| (E)-N-(6-Bromo-pyridin-2-ylmethyl)-N-(1-isopropyl-piperidin-4-yl)-3-(4-trifluoromethyl-phenyl)-acrylamide | 0.77 LC-MS 4 | 510.2 |
| (E)-N-(5-Bromo-pyridin-3-ylmethyl)-N-(1-isopropyl-piperidin-4-yl)-3-(4-trifluoromethyl-phenyl)-acrylamide | 0.74 LC-MS 4 | 510.2 |
| 4-{(4-Bromo-benzyl)-[(E)-3-(4-trifluoromethyl-phenyl)-acryloyl]-amino}-piperidine-1-carboxylic acid tert-butyl ester | 1.10 LC-MS 3 | 566.9 |
| (E)-N-(6-Bromo-pyridin-3-ylmethyl)-N-((S)-1-isopropyl-piperidin-3-yl)-3-(4-trifluoromethyl-phenyl)-acrylamide | 0.78 LC-MS 4 | 510.0 |

Synthesis of (E)-N-(4-Bromo-benzyl)-N-(1-cyclopentyl-piperidin-4-yl)-3-(4-trifluoromethyl-phenyl)-acrylamide Step 1: To a solution of 1-cyclopentylpiperidin-4-amine hydrochloride (2.10 g, 11.0 mmol, 1.0 eq.) in DCM (50 mL), 4-brombenzaldehyde (2.04 g, 11.0 mmol, 1.0 eq.) was added.

Sodium triacetoxyborohydride (2.81 g, 13.2 mmol, 1.2 eq.) was added portionwise and the reaction mixture was stirred at r.t. for 18 hours. Sat. aq. NaHCO₃ soln. (100 mL) was added and the mixture was stirred at r.t. for 2 hours. The layers were separated and the organic phase was dried over MgSO₄ and concentrated in vacuo. The residue was purified by flashmaster (column: 100 g, flow: 45 mL/min, 30 fractions of 45 mL, AcOEt/NEt₃ (10% NEt₃) to MeOH 10%/AcOEt/NEt₃ (10% NEt₃)) to give N-(4-bromobenzyl)-1-

Synthesis of (E)-N-(4-Bromo-benzyl)-N-(1-cyclopentyl-azetidin-3-yl)-3-(4-trifluoromethyl-phenyl)-acrylamide Step 1: To a solution of 1-cyclopentylazetidin-3-amine hydrochloride (2.03 g, 9.52 mmol, 1.0 eq.) in DCM (50 mL), 4-brombenzaldehyde (1.76 g, 9.52 mmol, 1.0 eq.) was added. Sodium triacetoxyborohydride (2.42 g, 11.43 mmol, 1.2 eq.) was added portionwise and the reaction mixture was stirred at r.t. for 18 hours. Sat. aq. NaHCO₃ sol. (100 mL) was added and the mixture was stirred at r.t. for 2 hours. The layers were separated and the organic phase was dried over MgSO₄ and concentrated in vacuo. The residue was purified by flashmaster (column: 340 g, flow: 90 mL/min, 90 fractions of 45 mL, AcOEt/NEt₃ (10% NEt₃) 100% to 95% with MeOH) to afford (4-bromo-benzyl)-(1-cyclopentyl-azetidin-3-yl)-amine as a yellow oil.

LC-MS 2: $t_R$=0.42 min; [M+H]⁺=309.2

Step 2: To a solution of 4-(trifluoromethyl)cinnamic acid (105 mg, 0.49 mmol, 1.0 eq.) in DCM (2.0 mL), DIPEA (0.25 mL, 1.46 mmol, 3.0 eq.) and TBTU (156 mg, 0.49 mmol, 1.0 eq.) were added in sequence. The resulting solution was stirred at r.t. for 30 minutes. Then a solution of (4-bromo-benzyl)-(1-cyclopentyl-azetidin-3-yl)-amine (150 mg, 0.49 mmol, 1.0 eq.) in DCM (1.0 mL) was added and the resulting mixture was stirred at r.t. for 18 hours.

The reaction mixture was poured in water. The mixture was extracted with DCM (2×). The comb. org. phases were dried over MgSO$_4$ and concentrated in vacuo. The residue was purified by flashmaster (column: 50 g, flow: 40 mL/min, 60 fractions of 15 mL, Hept/AcOEt/NEt$_3$ (10% NEt$_3$) 80:20 to AcOEt/NEt$_3$ (10% NEt$_3$)) to yield the title compound as a yellow gum.

LC-MS 3: $t_R$=1.08 min; [M+H]$^+$=506.9

Synthesis of (E)-N-(6-Bromo-pyridin-3-ylmethyl)-N-(1'-methyl-[1,4']bipiperidinyl-4-yl)-3-(4-trifluoromethyl-phenyl)-acrylamide To a solution of 1'-methyl-[1,4'-bipiperidin]-4-amine hydrochloride (540 mg, 2 mmol, 1.0 eq.) in EtOH (10 mL), triethylamine (0.56 mL, 4 mmol, 2.0 eq.) and 6-bromo-3-pyridinecarboxaldehyde (372 mg, 2 mmol, 1.0 eq.) were added in sequence. The resulting solution was stirred at 60° C. for 18 hours. The solution was cooled to 0° C. and sodium borohydride (118 mg, 3 mmol, 1.5 eq.) was added portionwise. The cooling bath was removed and the solution was stirred at r.t. for 2 hours. The resulting reaction mixture was quenched with sat. aq. NaHCO$_3$ solution (25 mL). The mixture was extracted with DCM (2×25 mL). The comb. org. phases were dried over MgSO$_4$ and concentrated in vacuo. To a mixture of the residue and 4-(trifluoromethyl)cinnamic acid (432 mg, 2 mmol, 1.0 eq.) in DMF (10 mL), EDC (575 mg, 3 mmol, 1.5 eq) and 4-(dimethylamino)pyridine (367 mg, 3 mmol, 1.5 eq.) were added in sequence. The mixture was stirred at r.t. for 65 hours. The mixture was diluted with AcOEt (40 mL). The diluted solution was washed with sat. aq. NaHCO$_3$ soln. (2×15 mL), sat. aq. NaCl soln. (1×15 mL), dried over MgSO$_4$, and concentrated in vacuo. The residue was purified by prep. HPLC (column: Waters X-Bridge, 30×75 mm, 10 μm, UV/MS, basic conditions) and concentrated in vacuo to afford the title compound as a pale yellow solid.

LC-MS 2: $t_R$=0.64 min; [M+H]$^+$=565.0

General Method for the Synthesis of a Boc-Protected Amine 12

Step 1: To a solution of 1-N-Boc-4-aminopiperidine (125 mg, 0.62 mmol, 1.0 eq.) in methanol (1 mL), triethylamine (0.07 mL, 0.50 mmol, 1.0 eq.) and 6-(2-methyl-pyridin-4-ylamino)-pyridine-3-carbaldehyde (107 mg, 0.50 mmol, 1.0 eq.) were added in sequence. The resulting solution was refluxed for 4 hours and further stirred at r.t. for 18 hours. The mixture was cooled to 0° C. and sodium borohydride (30 mg, 0.75 mmol, 1.5 eq.) was added portionwise. The solution was stirred at r.t. for 1 hour. The resulting reaction mixture was quenched with sat. aq. NaHCO$_3$ solution. The mixture was extracted with DCM (2×). The comb. org. phases were dried over MgSO$_4$, and concentrated in vacuo to afford 4-[4-(2-methyl-pyridin-4-ylamino)-benzylamino]-piperidine-1-carboxylic acid tert-butyl ester as a colorless oil. The product was used without further purification.

LC-MS 3: $t_R$=0.82 min; [M+H]$^+$=397.1

Step 2: To a solution of 4-(trifluoromethyl)cinnamic acid (179 mg, 0.83 mmol, 1.0 eq.) in DMF (4 mL), DIPEA (0.43 mL, 2.49 mmol, 3.0 eq.) and TBTU (320 mg, 1.00 mmol, 1.2 eq.) were added in sequence. The resulting solution was stirred at r.t. for 30 minutes. A solution of 4-[4-(2-methyl-pyridin-4-ylamino)-benzylamino]-piperidine-1-carboxylic acid tert-butyl ester (329 mg, 0.83 mmol, 1.0 eq.) in DMF (3 mL) was added and the resulting mixture was stirred at r.t. for 18 hours. The mixture was purified by prep. HPLC (column: Waters X-Bridge, 30×75 mm, 10 μm, UV/MS, basic conditions) and concentrated in vacuo (Genevac) to afford the desired Boc-protected amine 12 as a yellow foam.

Listed in Table 20 below are amines of Boc-protected amine 12, prepared according to the above-mentioned method with the corresponding amine 14 (or the corresponding salt) as starting material.

TABLE 20

| Boc-protected amine 12 | $t_R$ [min] LC-MS Method | MS-data m/z [M + H]$^+$ |
|---|---|---|
| 4-{[4-(2-Methyl-pyridin-4-ylamino)-benzyl]-[(E)-3-(4-trifluoromethyl-phenyl)-acryloyl]-amino}-piperidine-1-carboxylic acid tert-butyl ester | 0.96 LC-MS 3 | 595.1 |
| (S)-3-{[4-(Methyl-pyridin-4-yl-amino)-benzyl]-[(E)-3-(4-trifluoromethyl-phenyl)-acryloyl]-amino}-piperidine-1-carboxylic acid tert-butyl ester | 1.01 LC-MS 3 | 595.2 |
| (R)-3-{[4-(Methyl-pyridin-4-yl-amino)-benzyl]-[(E)-3-(4-trifluoromethyl-phenyl)-acryloyl]-amino}-piperidine-1-carboxylic acid tert-butyl ester | 1.01 LC-MS 3 | 595.2 |
| (±)-4-{[4-(Methyl-pyridin-4-yl-amino)-benzyl]-[(E)-3-(4-trifluoromethyl-phenyl)-acryloyl]-amino}-azepane-1-carboxylic acid tert-butyl ester | 1.05 LC-MS 3 | 609.2 |
| (±)-3-{[4-(Methyl-pyridin-4-yl-amino)-benzyl]-[(E)-3-(4-trifluoromethyl-phenyl)-acryloyl]-amino}-azepane-1-carboxylic acid tert-butyl ester | 1.05 LC-MS 3 | 609.0 |
| 6-{[4-(Methyl-pyridin-4-yl-amino)-benzyl]-[(E)-3-(4-trifluoromethyl-phenyl)-acryloyl]-amino}-2-aza-spiro[3.3]heptane-2-carboxylic acid tert-butyl ester | 0.98 LC-MS 3 | 607.0 |
| (3aR,6aS)-5-{[4-(Methyl-pyridin-4-yl-amino)-benzyl]-[(E)-3-(4-trifluoromethyl-phenyl)-acryloyl]-amino}-octahydro-cyclopenta[c]pyrrole-2-carboxylic acid tert-butyl ester (mixture of stereoisomers) | 0.86 LC-MS 3 | 621.9 |
| 9-{[4-(Methyl-pyridin-4-yl-amino)-benzyl]-[(E)-3-(4-trifluoromethyl-phenyl)-acryloyl]-amino}-3-aza-spiro[5.5]undecane-3-carboxylic acid tert-butyl ester | 1.06 LC-MS 3 | 663.1 |

TABLE 20-continued

| Boc-protected amine 12 | $t_R$ [min] LC-MS Method | MS-data m/z [M + H]+ |
|---|---|---|
| (±)-trans-3-Fluoro-4-{[4-(methyl-pyridin-4-yl-amino)-benzyl]-[(E)-3-(4-trifluoromethyl-phenyl)-acryloyl]-amino}-piperidine-1-carboxylic acid tert-butyl ester | 0.98 LC-MS 3 | 612.9 |
| (±)-cis-3-Fluoro-4-{[4-(methyl-pyridin-4-yl-amino)-benzyl]-[(E)-3-(4-trifluoromethyl-phenyl)-acryloyl]-amino}-piperidine-1-carboxylic acid tert-butyl ester | 0.98 LC-MS 3 | 612.9 |

Synthesis of 4-{[4-(Methyl-pyridin-4-yl-amino)-benzyl]-[(E)-3-(4-trifluoromethyl-phenyl)-actyloyl]-amino}-piperidine-1-carboxylic acid tert-butyl ester Step 1: To a solution of 4-amino-Boc-piperidine hydrochloride (11.84 g, 50 mmol, 1.0 eq.) in MeOH (100 mL), NEt$_3$ (6.96 mL, 50 mmol, 1.0 eq.) and 4-bromobenzaldehyde (9.25 g, 50 mmol, 1.0 eq.) were added in sequence. The resulting solution was refluxed for 18 hours. The solution was cooled to 0° C. and sodium borohydride (3.03 g, 80 mmol, 1.6 eq.) was added portionwise. The cooling bath was removed and the solution was stirred at r.t. for 3 hours. The resulting reaction mixture was quenched with sat. aq. NaHCO$_3$ soln. (50 mL). The mixture was extracted with DCM (3×50 mL). The comb. org. phases were washed with sat. aq. NaCl soln. (1×50 mL), dried over MgSO$_4$, and concentrated in vacuo to give 4-(4-bromo-benzylamino)-piperidine-1-carboxylic acid tert-butyl ester as a white solid. The product was used without further purification.

LC-MS 4: $t_R$=0.69 min; [M+H]+=369.0

Step 2: To a mixture of 4-(4-bromo-benzylamino)-piperidine-1-carboxylic acid tert-butyl ester (7.39 g, 20 mmol, 1.0 eq.) and 4-(trifluoromethyl)cinnamic acid (4.32 g, 20 mmol, 1.0 eq.) in DMF (50 mL), EDC (5.75 g, 30 mmol, 1.5 eq.) and 4-(dimethylamino)pyridine (3.67 g, 30 mmol, 1.5 eq.) were added in sequence. The mixture was stirred at r.t. for 15 hours. The mixture was diluted with AcOEt (300 mL). The diluted solution was washed with 1N aq. HCl (2×150 mL), sat. aq. NaHCO$_3$ soln. (2×150 mL), sat. aq. NaCl soln. (1×150 mL), dried over MgSO$_4$, and concentrated in vacuo. The residue was purified by CC (SiO$_2$, Hept/AcOEt 6:4 to 1:1) to give 4-{(4-bromo-benzyl)-[(E)-3-(4-trifluoromethyl-phenyl)-acryloyl]-amino}-piperidine-1-carboxylic acid tert-butyl ester as a white foam.

LC-MS 2: $t_R$=1.07 min; [M+H]+=567.1

Step 3: A solution of 4-{(4-bromo-benzyl)-[(E)-3-(4-trifluoromethyl-phenyl)-acryloyl]-amino}-piperidine-1-carboxylic acid tert-butyl ester (500 mg, 0.88 mmol, 1.00 eq.), sodium tert-butoxide (106 mg, 1.10 mmol, 1.25 eq.), 4-(methylamino)pyridine (146 mg, 1.32 mmol, 1.50 eq.), 2-(dicyclohexylphosphino)-3,6-dimethoxy-2'-4'-6'-tri-i-propyl-1,1'-biphenyl (47 mg, 0.09 mmol, 0.10 eq.) and tris-(dibenzylidenaceton)-dipalladium (40 mg, 0.04 mmol, 0.05 eq.) in dioxane (20 mL) was degassed with N$_2$ for 15 min. The solution was then stirred at 105° C. for 18 hours. The reaction was allowed to cool to r.t. and filtered through Celite. The filtrate was concentrated in vacuo. The residue was partitioned between water (70 mL) and DCM (100 mL). The layers were separated and the aq. phase was extracted with DCM (2×70 mL). The comb. org. phases were dried over MgSO$_4$ and concentrated in vacuo. The residue was purified by flashmaster (column: 100 g, flow: 45 mL/min, 60 fractions of 45 mL, Hept/AcOEt/NEt$_3$ (10% NEt$_3$) 85:15 to AcOEt/NEt$_3$ (10% NEt$_3$)) to yield the title compound as a yellow solid.

LC-MS 4: $t_R$=0.84 min; [M+H]+=595.3

General Method for the Synthesis of a Compound of Structure 10

To an ice-cooled solution of 4-{[4-(2-methyl-pyridin-4-ylamino)-benzyl]-[(E)-3-(4-trifluoromethyl-phenyl)-acryloyl]-amino}-piperidine-1-carboxylic acid tert-butyl ester (4.04 g, 6.79 mmol, 1.0 eq.) in DCM (60 mL), 4M HCl in dioxane (60 mL) was added. The resulting mixture was allowed to warm up to r.t. and was stirred at r.t. for 4 hours. The reaction mixture was treated with a sat. aq. NaHCO$_3$ soln. The layers were separated and the aq. phase was extracted with DCM (2×). The comb. org. phases were dried over MgSO$_4$ and concentrated in vacuo to give the desired amine as brown foam. The product was used without further purification.

Listed in Table 21 below are amines of Structure 10, prepared according to the above-mentioned method with the corresponding Boc-protected amine 12 as starting material.

TABLE 21

| Amine of Structure 10 | $t_R$ [min] LC-MS Method | MS-data m/z [M + H]+ |
|---|---|---|
| (E)-N-[4-(2-Methyl-pyridin-4-ylamino)-benzyl]-N-piperidin-4-yl-3-(4-trifluoromethyl-phenyl)-acrylamide | 0.83 LC-MS 3 | 495.1 |
| (E)-N-[4-(Methyl-pyridin-4-yl-amino)-benzyl]-N-piperidin-4-yl-3-(4-trifluoromethyl-phenyl)-acrylamide | 0.54 LC-MS 2 | 495.3 |
| (E)-N-[4-(Methyl-pyridin-4-yl-amino)-benzyl]-N-(S)-piperidin-3-yl-3-(4-trifluoromethyl-phenyl)-acrylamide | 0.61 LC-MS 4 | 495.5 |
| (E)-N-[4-(Methyl-pyridin-4-yl-amino)-benzyl]-N-(R)-piperidin-3-yl-3-(4-trifluoromethyl-phenyl)-acrylamide | 0.85 LC-MS 3 | 495.2 |
| (±)-(E)-N-Azepan-4-yl-N-[4-(methyl-pyridin-4-yl-amino)-benzyl]-3-(4-trifluoromethyl-phenyl)-acrylamide | 0.89 LC-MS 3 | 509.2 |
| (±)-(E)-N-Azepan-3-yl-N-[4-(methyl-pyridin-4-yl-amino)-benzyl]-3-(4-trifluoromethyl-phenyl)-acrylamide | 0.90 LC-MS 3 | 509.1 |
| (E)-N-[4-(Methyl-pyridin-4-yl-amino)-benzyl]-N-(3aR,6aS)-octahydro-cyclopenta[c]pyrrol-5-yl-3-(4-trifluoromethyl-phenyl)-acrylamide (mixture of stereoisomers) | 0.63 LC-MS 4 | 521.4 |

TABLE 21-continued

| Amine of Structure 10 | $t_R$ [min] LC-MS Method | MS-data m/z [M + H]+ |
|---|---|---|
| (E)-N-(3-Aza-spiro[5.5]undec-9-yl)-N-[4-(methyl-pyridin-4-yl-amino)-benzyl]-3-(4-trifluoromethyl-phenyl)-acrylamide | 0.98 LC-MS 3 | 562.3 |
| (±)-(E)-N-(cis-3-Fluoro-piperidin-4-yl)-N-[4-(methyl-pyridin-4-yl-amino)-benzyl]-3-(4-trifluoromethyl-phenyl)-acrylamide | 0.61 LC-MS 4 | 512.9 |
| (±)-(E)-N-(trans-3-Fluoro-piperidin-4-yl)-N-[4-(methyl-pyridin-4-yl-amino)-benzyl]-3-(4-trifluoromethyl-phenyl)-acrylamide | 0.62 LC-MS 4 | 513.0 |

Synthesis of (E)-N-(4-(methyl(pyridin-4-yl)amino) benzyl)-N-(2-azaspiro[3.3]heptan-6-yl)-3-(4-(trifluoromethyl)phenyl)acrylamide formate To an ice-cooled solution of 6-{[4-(methyl-pyridin-4-yl-amino)-benzyl]-[(E)-3-(4-trifluoromethyl-phenyl)-acryloyl]-amino}-2-aza-spiro[3.3]heptane-2-carboxylic acid tert-butyl ester (300 mg, 0.49 mmol, 1 eq.) in DCM (8 mL), trifluoroacetic acid (0.38 mL, 4.94 mmol, 10 eq.) was added dropwise. The mixture was stirred at r.t. for 48 hours. The mixture was concentrated in vacuo and the residue was purified by prep HPLC (column: Waters Xbridge C18, 10 um, 30×75 mm, acidic conditions) to yield the title compound as a yellow oil.

LC-MS 4: $t_R$=0.60 min; [M+H]+=507.1

General Method for the Synthesis of an Aldehyde 3

Step 1: A solution of 2-(4-bromophenyl)-1,3-dioxolane (2.48 g, 10.81 mmol, 1.00 eq.), sodium tert-butoxide (1.30 g, 13.51 mmol, 1.25 eq.) and 4-(methylamino)pyridine (1.17 g, 10.81 mmol, 1.00 eq.) in dioxane (110 mL) was degased with $N_2$ for 15 min. X-Phos (515 mg, 1.08 mmol, 0.10 eq.) and tris(dibenzylideneacetone)dipalladium(0) (495 mg, 0.54 mmol, 0.05 eq.) were added in sequence. The reaction mixture was degased again with $N_2$ for 15 min and then heated to 105° C. for 48 hours. The reaction was allowed to cool down to r.t. and filtered through Celite. The Celite was rinsed with dioxane and the filtrate was concentrated in vacuo. The residue was purified by flashmaster (column: 100 g, flow: 45 mL/min, 40 fractions of 45 mL, from Hept/AcOEt-NEt₃ (10% NEt₃) 5:5 to 100% AcOEt-NEt₃ (10% NEt₃)) to yield (4-[1,3]dioxolan-2-yl-phenyl)-methyl-pyridin-4-yl-amine as a brown gum.

LC-MS 2: $t_R$=0.75 min; [M+H]+=256.9

Step 2: To a solution of (4-[1,3]dioxolan-2-yl-phenyl)-methyl-pyridin-4-yl-amine (1.50 g, 5.85 mmol, 1.00 eq.) in THF (100 mL)/water (4 mL), p-toluenesulfonic acid (1.59 g, 8.88 mmol, 1.52 eq.) was added and the reaction mixture was stirred at 50° C. for 1.5 hours. The reaction mixture was treated with a sat. aq. NaHCO₃ soln. and extracted with DCM (2×). The comb. org. phases were dried over MgSO₄ and concentrated in vacuo to afford the desired aldehyde as an yellow oil. The product was used without further purification.

Listed in Table 22 below are aldehydes 3, prepared according to the above-mentioned method with the corresponding amine as starting material.

TABLE 22

| Aldehyde 3 | $t_R$ [min] LC-MS Method | MS-data m/z [M + H]+ |
|---|---|---|
| 4-(Methyl-pyridin-4-yl-amino)-benzaldehyde | 0.71 LC-MS 2 | 213.2 |
| 4-(2-Methyl-pyridin-4-ylamino)-benzaldehyde | 0.68 LC-MS 2 | 213.1 |

TABLE 22-continued

| Aldehyde 3 | $t_R$ [min] LC-MS Method | MS-data m/z [M + H]+ |
|---|---|---|
| 4-[Methyl-(1-methyl-piperidin-4-yl)-amino]-benzaldehyde | 0.72 LC-MS 3 | 233.2 |

Synthesis of 4-[Methyl-(2-Methyl-Pyridin-4-Yl)-Amino]-Benzaldehyde

Step 1: To an ice-cooled solution of (4-[1,3]dioxolan-2-yl-phenyl)-(2-methyl-pyridin-4-yl)-amine (315 mg, 1.23 mmol, 1.0 eq.) in DMF (7 mL), sodium hydride 60% dispersion in mineral oil (49 mg, 1.23 mmol, 1.0 eq.) was added portionwise. The reaction mixture was stirred at r.t. under $N_2$ for 30 min. Iodomethane (84 µL, 1.35 mmol, 1.1 eq.) was added and the mixture was stirred at r.t. for 18 hours. The reaction mixture was partitioned between DCM and water. The layers were separated and the aq. phase was extracted with DCM (2×). The comb. org. phases were dried over MgSO₄ and concentrated in vacuo. The residue was purified by flashmaster (column: 50 g, flow: 45 mL/min, 20 fractions of 45 mL, Hept/AcOEt-NEt₃ (10% NEt₃) 3:7 to 100% AcOEt-NEt₃ (10% NEt₃)) to yield (4-[1,3]dioxolan-2-yl-phenyl)-methyl-(2-methyl-pyridin-4-yl)-amine as a brown oil.

LC-MS 2: $t_R$=0.77 min; [M+H]+=271.0

Step 2: To a solution of (4-[1,3]dioxolan-2-yl-phenyl)-methyl-(2-methyl-pyridin-4-yl)-amine (240 mg, 0.89 mmol, 1.00 eq.) in THF (17 mL)/water (7 mL), p-toluenesulfonic acid (242 mg, 1.35 mmol, 1.52 eq.) was added and the reaction mixture was stirred at 50° C. for 2 hours. The reaction mixture was treated with a sat. aq. NaHCO₃ soln. and extracted with DCM (2×). The comb. org. phases were dried over MgSO₄ and concentrated in vacuo to afford the title compound as a brown oil. The product was used without further purification.

LC-MS 2: $t_R$=0.74 min; [M+H]+=227.2

General Method for the Synthesis of an Aldehyde 3

Step 1: To a solution of 6-bromo-3-pyridinecarboxaldehyde (1.96 g, 10 mmol, 1.0 eq.) in toluene (10 mL), ethylene glycol (1.12 mL, 20 mmol, 2.0 eq.) and (±)-camphor-10-sulfonic acid (237 mg, 1 mmol, 0.1 eq.) were added. The reaction mixture was heated to reflux with azeotropic removal of the evolved water for 2 hours (Dean-Stark apparatus). The solvent was removed in vacuo. The residue was partitioned between sat. aq. NaHCO₃ soln. and AcOEt. The layers were separated and the aq. phase was extracted with AcOEt (2×). The comb. org. layers were washed with a sat. aq. NaCl soln., dried over MgSO₄, filtered, and concentrated in vacuo. The residue was purified by flashmaster (column: 100 g, flow: 45 mL/min, 30 fractions of 45 mL, from 99% Hept/AcOEt-NEt₃ (10%) to Hept/AcOEt-NEt₃ (10%) 6:4) to yield 2-bromo-5-[1,3]dioxolan-2-yl-pyridine as a colorless oil.

LC-MS 3: $t_R$=0.73 min; [M+H]⁺=no ionization

Step 2: A solution of 2-bromo-5-[1,3]dioxolan-2-yl-pyridine (2.09 g, 9.09 mmol, 1.00 eq.), sodium tert-butoxide (1.09 g, 11.36 mmol, 1.25 eq.) and 4-amino-2-picoline (982 mg, 9.09 mmol, 1.00 eq.) in dioxane (95 mL) was degased with N₂ for 15 min before the addition of X-Phos (433 mg, 0.91 mmol, 0.10 eq.) and tris(dibenzylideneacetone)dipalladium(0) (416 mg, 0.45 mmol, 0.05 eq.). The reaction mixture was degased again with N₂ for 15 min and then stirred at 105° C. for 18 hours. The reaction was allowed to cool down to r.t. and filtered through Celite. The filtrate was concentrated in vacuo. The residue was purified by flashmaster (column: 100 g, flow: 45 mL/min, 40 fractions of 45 mL, from AcOEt-NEt₃ (10%) to 93% AcOEt-NEt₃ (10%) with MeOH) to yield (5-[1,3]dioxolan-2-yl-pyridin-2-yl)-(2-methyl-pyridin-4-yl)-amine as a light brown foam.

LC-MS 3: $t_R$=0.67 min; [M+H]⁺=258.1

Step 3: To a solution of (5-[1,3]dioxolan-2-yl-pyridin-2-yl)-(2-methyl-pyridin-4-yl)-amine (1.96 g, 7.62 mmol, 1.0 eq.) in THF (125 mL)/water (5 mL), p-toluenesulfonic acid (2.08 g, 11.58 mmol, 1.5 eq.) was added and the reaction mixture was stirred at 50° C. for 2 hours. The suspension was treated with a sat. NaHCO₃ soln. and extracted with DCM (2×). The comb. org. phases were dried over MgSO₄, and concentrated in vacuo to afford the desired aldehyde as an yellow solid. The product was used whiteout further purification.

Listed in Table 23 below are aldehydes 3, prepared according to the above-mentioned method with the corresponding pyridinecarboxaldehyde as starting material.

TABLE 23

| Aldehyde 3 | $t_R$ [min] LC-MS Method | MS-data m/z [M + H]⁺ |
|---|---|---|
| 6-(2-Methyl-pyridin-4-ylamino)-pyridine-3-carbaldehyde | 0.65 LC-MS 3 | 214.1 |
| 5-(2-Methyl-pyridin-4-ylamino)-pyridine-2-carbaldehyde | 0.61 LC-MS 3 | 214.1 |

Synthesis of 4-(2,6-Dimethyl-pyridin-4-yloxy)-benzaldehyde

To a solution of 4-fluor-benzaldehyde (1.00 g, 8.06 mmol, 1.00 eq.) in DMA (7 mL), 2,6-dimethyl-4-hydroxypyridine (1.09 g, 8.86 mmol, 1.10 eq.) and K₂CO₃ (1.11 g, 8.46 mmol, 1.05 eq.) were added. The reaction mixture was heated to reflux for 4 hours. The reaction mixture was diluted with ethyl acetate, washed with water and a sat. NaCl soln., dried over MgSO₄, and concentrated in vacuo. The residue was purified by flashmaster (column: 100 g, flow: 45 mL/min, 40 fractions of 45 mL, Hept/AcOEt 8:2 to 100% AcOEt) to yield the title compound as a white solid.

LC-MS 3: $t_R$=0.78 min; [M+H]⁺=228.1

Synthesis of 4-(Pyridin-4-yloxy)-benzaldehyde

To a solution of 4-hydroxybenzaldehyde (1.13 g, 8.81 mmol, 1 eq.) in DMA (7 mL), 4-chloropyridine (1.00 g, 8.81 mmol, 1 eq.) and potassium carbonate (1.22 g, 8.81 mmol, 1 eq.) were added. The reaction mixture was heated to reflux for 4 hours. The reaction mixture was diluted with ethyl acetate, washed with water and a sat. NaCl soln., dried over MgSO₄, and concentrated in vacuo. The residue was purified by flashmaster (column: 100 g, flow: 45 mL/min, 30 fractions of 45 mL, Hept/AcOEt 5:5 to 100% AcOEt) to yield the title compound as a light yellow oil.

LC-MS 3: $t_R$=0.73 min; [M+H]⁺=200.2

Synthesis of 4-(Pyridine-4-carbonyl)-benzaldehyde

Step 1: A solution of isonicotinic acid (3.00 g, 24.1 mmol, 1.0 eq.) in thionylchloride (10 mL) was stirred at 100° C. for 1.5 hours. The reaction mixture was allowed to cool to r.t. and concentrated in vacuo. To an ice-cooled solution of the residue in toluene (16 mL), AlCl₃ (6.02 g, 45.1 mmol, 1.9 eq.) was added. The mixture was allowed to slowly warm to r.t. The solution was then stirred at 90° C. for 4 hours and further at r.t. for 18 hours. The reaction was slowly poured into 4.2% HCl/ice-water soln. The pH of the aq. layer was adjusted to ca. 10 by the addition of Na₂CO₃, followed by addition of sat. aq. NaOH soln. The aq. layer was extracted with DCM, dried over MgSO₄, and concentrated in vacuo. The residue was recrystallized from heptane and dried in vacuo to yield pyridin-4-yl-p-tolyl-methanone as light yellow crystals.

LC-MS 4: $t_R$=0.70 min; [M+H]⁺=198.2

Step 2: To a mixture of AcOH (15 mL) and Ac₂O (15 mL), pyridin-4-yl-p-tolyl-methanone (1.96 g, 9.9 mmol, 1.0 eq.) was added. The resulting light orange solution was cooled in an ice bath and conc. H₂SO₄ (4 mL) was added slowly. Chrom(VI)-oxide (2.48 g, 24.8 mmol, 2.5 eq.) was added portionwise at such a rate to maintain the internal temperature below 10° C. Upon addition completion, the mixture was stirred at 0° C. for 30 min. The solution was poured into ice (50 g). The pH of the resulting solution was adjusted to 8-9 with 30% K₂CO₃ soln. (~150 mL). The aq. layer was extracted with DCM (3×50 mL). The comb. org. phases were dried over MgSO₄, and concentrated in vacuo. The residue was recrystallized from EtOH and dried under vacuum to give acetic acid acetoxy-[4-(pyridine-4-carbonyl)-phenyl]-methyl ester as light brown crystals.

LC-MS 4: $t_R$=0.75 min; [M+H]⁺=314.1

Step 3: A solution of acetic acid acetoxy-[4-(pyridine-4-carbonyl)-phenyl]-methyl ester (792 mg, 2.53 mmol, 1 eq.) in EtOH/H₂O/conc. H₂SO₄ 10:10:1 (21 mL) was refluxed for 30 min. The reaction mixture was allowed to cool to r.t. The pH was adjusted to 8-9 with 30% aq. K₂CO₃ soln. and the mixture was cooled in an ice bath. The resulting suspension was filtered, the solids were washed with water, and dried in vacuo to afford the title compound as a white-off solid.

LC-MS 4: $t_R$=0.63 min; [M+H]⁺=212.3

General Method for the Synthesis of an Amine 4

To a solution of cyclopentanone (4.52 mL, 50 mmol, 1.0 eq.) in acetonitrile (500 mL), 4-(N-boc-amino)piperidine (10.22 g, 50 mmol, 1.0 eq.) was added. Sodium triacetoxyborohydride (15.90 g, 75 mmol, 1.5 eq.) was added portionwise and the reaction mixture was stirred at r.t. for 18 hours. The solvent was removed in vacuo. The residue was partitioned between sat. aq. NaHCO₃ soln. and AcOEt. The layers were separated and the aq. phase was extracted with AcOEt (2×). The comb. org. phases were washed with sat. aq. NaCl soln., dried over MgSO₄, and concentrated in vacuo. To an ice-cooled solution of the residue in DCM (400 mL), 4M HCl in dioxane (400 mL) was added and the reaction mixture was stirred at r.t. for 18 hours. The mixture was concentrated in vacuo. The residue was dried on high vacuum to give the desired amine 4 as a white solid. The product was used without further purification.

Listed in Table 24 below are amine 4 (or the corresponding salt), prepared according to the above-mentioned method with the corresponding boc-protected amine and the corresponding carbonyl derivative as starting materials.

TABLE 24

| Amine 4 | $t_R$ [min] LC-MS Method | MS-data m/z $[M + H]^+$ |
|---|---|---|
| 1-Cyclopentylpiperidin-4-amine hydrochloride | 0.18 LC-MS 4 | 169.1 |
| 1-Isopentylpiperidin-4-amine hydrochloride | 0.25 LC-MS 4 | 171.1 |
| (±)-1-Cyclopentylpyrrolidin-3-amine hydrochloride | 0.64 LC-MS 3 | 155.1 |
| (R)-1-Cyclopentylpyrrolidin-3-amine hydrochloride | 0.64 LC-MS 3 | 155.1 |
| (S)-1-Cyclopentylpyrrolidin-3-amine hydrochloride | 0.64 LC-MS 3 | 155.1 |
| (S)-1-Isopropyl-piperidin-3-ylamine hydrochloride | 0.15 LC-MS 4 | 143.1 |
| 1-Cyclopentylazetidin-3-amine hydrochloride | 0.12 LC-MS 2 | 141.3 |

Synthesis of 1'-methyl-[1,4'-bipiperidin]-4-amine hydrochloride

Step 1: To a solution of 1-methyl-4-piperidone (1.2 mL, 10 mmol, 1.0 eq) in THF (40 mL), 4-(N-boc-amino)piperidine (2.00 g, 10 mmol, 1.0 eq.), sodium triacetoxyborohydride (4.24 g, 20 mmol, 2.0 eq.) and acetic acid (0.57 mL, 10 mmol, 1.0 eq.) were added and the reaction mixture was stirred at r.t. for 18 hours. 1-Methyl-4-piperidone (566 mg, 5 mmol, 0.5 eq.), acetic acid (0.29 mL, 5 mmol, 0.5 eq.) and sodium triacetoxyborohydride (2.12 g, 10 mmol, 1.0 eq.) were added and the mixture was further stirred at r.t. for 3 hours. The solvent was removed in vacuo and the residue was partitioned between sat. aq. NaHCO$_3$ soln. and DCM. The layers were separated and the aq. phase was extracted with DCM (2×). The comb. org. phases were dried over MgSO$_4$, filtered, and concentrated in vacuo. The residue was purified by flashmaster (column: 100 g, flow: 45 mL/min, 40 fractions of 45 mL, from 96% AcOEt-NEt$_3$ (10%) with MeOH to 90% AcOEt-NEt$_3$ (10%) with MeOH to yield (1'-methyl-[1,4']bipiperidinyl-4-yl)-carbamic acid tert-butyl ester as an orange solid.

LC-MS 3: $t_R$=0.73 min; $[M+H]^+$=297.9

Step 2: To a solution of (1'-methyl-[1,4']bipiperidinyl-4-yl)-carbamic acid tert-butyl ester (1.01 g, 3.4 mmol, 1 eq.) in methanol (35 mL), conc. HCl (4.5 mL) was added dropwise. The reaction mixture was heated to 70° C. for 5 hours. The hot solution was allowed to cool down to r.t. During the cooling process, the product started to crystallize. The flask was kept at 4° C. for 18 hours to complete the crystallization. The product was filtered, washed with Et$_2$O and dried to afford the title compound as white crystals. The product was used with no further purification.

LC-MS 2: $t_R$=0.10 min; $[M+H]^+$=198.3

General Method for the Synthesis of an Amine 4

Step 1: A solution of (±)-cis-1-N-cbz-1,4-cyclohexyldiamine (500 mg, 2.0 mmol, 1 eq.) in formaldehyde (36.5% in H$_2$O, 15 mL) and formic acid (0.25 mL, 6.6 mmol, 3.3 eq.) was heated at reflux for 4 hours. The mixture was allowed to cool to r.t. and poured into a sat. NaHCO$_3$ soln. (50 mL). The mixture was extracted with AcOEt (3×30 mL).

The comb. org. phases were dried over MgSO$_4$ and concentrated in vacuo. The residue was purified by prep. HPLC (column: Waters X-Bridge, 30×75 mm, 10 µm, UV/MS, basic conditions) to give (±)-cis-(4-dimethylamino-cyclohexyl)-carbamic acid benzyl ester as a white solid.

LC-MS 3: $t_R$=0.82 min; $[M+H]^+$=277.0

Step 2: To a solution under N$_2$ of (±)-cis-(4-dimethylamino-cyclohexyl)-carbamic acid benzyl ester (150 mg, 0.54 mmol, 1 eq.) in EtOH (10 mL), palladium on activated carbon (10 wt. %, 100 mg) was added. The flask was carefully evacuated and refilled with H$_2$ (3×). The black suspension was stirred at r.t. under an H$_2$-atmosphere for 18 hours. The black suspension was filtered through Celite and the filter cake was rinsed with EtOH. The filtrate was concentrated in vacuo to give the desired amine 4 as a yellow oil. The product was used without further purification.

Listed in Table 25 below are amine 4, prepared according to the above-mentioned method with the corresponding cbz-protected amine as starting material.

TABLE 25

| Amine 4 | $t_R$ [min] LC-MS Method | MS-data m/z $[M + H]^+$ |
|---|---|---|
| (±)-cis-N,N-Dimethyl-cyclohexane-1,4-diamine | 0.15 LC-MS 4 | 143.1 |
| (±)-trans-N,N-Dimethyl-cyclohexane-1,4-diamine | 0.15 LC-MS 4 | 143.2 |

Synthesis of (f)-cis-4-Amino-3-fluoro-piperidine-1-carboxylic acid tert-butyl ester To a solution of (±)-cis-4-benzylamino-3-fluoro-piperidine-1-carboxylic acid tert-butyl ester (prepared as described in J. Med. Chem. 1999, 42, 2087) (860 mg, 2.65 mmol, 1.0 eq.) in MeOH (10 mL), ammoniumformiat (702 mg, 11.1 mmol, 4.2 eq.) was added. The reaction mixture was flushed with N$_2$ twice and 10% Pd/C (250 mg) was added. The mixture was flushed again with N$_2$ and stirred at 50° C. for 1 hour. The reaction was cooled to r.t., filtered, and concentrated in vacuo to yield the title compound as a colorless oil. The product was used without further purification.

LC-MS 4: $t_R$=0.47 min; $[M+H]^+$=no ionization.

Synthesis of 9-Amino-3-aza-spiro[5.5]undecane-3-carboxylic acid tert-butyl ester Step 1: To a solution of 9-oxo-3-aza-spiro[5.5]undecane-3-carboxylic acid tert-butyl ester (927 mg, 3.47 mmol, 1.0 eq.) in 1,2-dichloroethane (16 mL), benzylamine (0.38 mL, 3.47 mmol, 1.0 eq.) was added. AcOH (0.30 mL, 5.2 mmol, 1.5 eq.) and sodium triacetoxyborohydride (1.10 g, 5.2 mmol, 1.5 eq.) were added in sequence. The mixture was stirred at r.t. for 1.5 hours. 1N aq. NaOH soln. was added until pH 9-10 and the mixture was stirred rapidly for a few minutes. The layers were separated and the aq. phase was extracted with DCM. The comb. org. phases were dried over MgSO$_4$ and concentrated in vacuo. The residue was purified by flash chromatography (DCM to DCM/MeOH 95:5) to yield 9-benzylamino-3-aza-spiro[5.5]undecane-3-carboxylic acid tert-butyl ester as a light yellow oil.

LC-MS 4: $t_R$=0.73 min; $[M+H]^+$=359.4

Step 2: To a solution under $N_2$ of 9-benzylamino-3-azaspiro[5.5]undecane-3-carboxylic acid tert-butyl ester (500 mg, 1.58 mmol, 1 eq.) in MeOH (8 mL), Pd(OH)$_2$ (450 mg) was added. The flask was evacuated and backfilled with $H_2$. The mixture was stirred rapidly under an $H_2$-atmosphere at r.t. for 18 hours. The mixture was filtered through celite and the celite was washed with methanol. The filtrate was concentrated in vacuo to give the title compound as a white solid. The product was used without further purification.

LC-MS 4: $t_R$=0.60 min; [M+H]$^+$=269.3

(±)-Cis-4-pyrrolidin-1-yl-cyclohexylamine and (±)-trans-4-pyrrolidin-1-yl-cyclohexylamine were prepared as described in US2007/0238718A1.

Synthesis of Methyl-(2-methyl-pyridin-4-yl)-amine

Step 1: To a solution of 4-amino-2-picoline (1.08 g, 10 mmol, 1.0 eq.), triethylamine (2.1 mL, 15 mmol, 1.5 eq.), and 4-(dimethylamino)pyridine (122 mg, 1 mmol, 0.1 eq.) in THF (30 mL), a solution of di-tert-butyl dicarbonate (2.62 g, 12 mmol, 1.2 eq.) in THF (20 mL) was added dropwise. Upon completion of the addition, the mixture was stirred at 50° C. for 4 hours. The reaction mixture was allowed to cool to r.t. and concentrated in vacuo. The residue was partitioned between water (50 mL) and DCM (50 mL). The layers were separated. The aq. phase was extracted with DCM (2×50 mL). The comb. org. phases were washed with water (1×50 mL), sat. aq. NaCl soln. (1×50 mL), dried over MgSO$_4$, and concentrated in vacuo. The residue was purified by flashmaster (column: 100 g, flow: 45 mL/min, 50 fractions of 45 mL, from Hept/AcOEt-NEt$_3$ (10% NEt$_3$) 9:1 to Hept/AcOEt-NEt$_3$ (10% NEt$_3$) 3:7) to yield (2-methyl-pyridin-4-yl)-carbamic acid tert-butyl ester as a white solid.

LC-MS 3: $t_R$=0.77 min; [M+H]$^+$=209.3

Step 2: To an ice-cooled solution of (2-methyl-pyridin-4-yl)-carbamic acid tert-butyl ester (995 mg, 4.8 mmol, 1 eq.) in THF (30 mL), lithiumaluminiumhydride (954 mg, 23.9 mmol, 5 eq.) was added portionwise. The resulting mixture was stirred at 70° C. for 14 hours. The mixture was cooled to 0° C. and quenched sequentially with water (2 mL), 1M aq. NaOH soln. (2 mL), and water (6 mL). The resulting suspension was diluted with EtOH (15 mL) and filtered through Celite. The filtrate was concentrated in vacuo. The residue was partitioned between 1M aq. NaOH (25 mL) and DCM (25 mL). The layers were separated. The aq. phase was extracted with DCM (2×25 mL). The comb. org. phases were dried over MgSO$_4$ and concentrated in vacuo to give the title compound as a pale yellow oil that solidified upon standing. The product was used without further purification.

LC-MS 4: $t_R$=0.34 min; [M+H]$^+$=123.2

In Vitro Antimalarial Activity: *Plasmodium falciparum* In Vitro Assay:

In vitro activity against erythrocytic stages of P. *Falciparum* in human red blood cells is determined using a [$^3$H]-hypoxanthine incorporation assay. One strain sensitive to all drugs (*P. Falciparum* NF54) is used in this assay and all tested compounds are compared for activity with the standard drugs chloroquine (sigma C6628) and artesunate (sigma 36, 159-3). Compounds, tested in duplicates, are serially diluted with screening medium [RPMI1640 medium, supplemented with HEPES (5.94 g/L), NaHCO$_3$ (2.1 g/L), neomycin (100 U/mL) and human serum (50% final concentration)] in 96-well microtiter plates within an appropriate concentration range. Thereafter, the parasite cultures incubated in screening medium containing washed human red blood cells at 2.5% hematocrit (0.3% parasitemia) are added to the serially diluted compounds and incubated in a humidifying atmosphere at 37° C., 4% CO$_2$, 3% O$_2$ and 93% N$_2$. After 48 hours, [$^3$H]-hypoxanthine (0.5 μCi) is added to each well of a plate. The plates are incubated for a further 24 hours under the same conditions then harvested with a Betaplate cell harvester (Wallac) and washed with distilled water. The dried filters are inserted into a plastic foil with 10 mL of scintillation fluid and counted in a Betaplate liquid scintillation counter. IC$_{50}$ values are calculated from sigmoidal inhibition curves using Microsoft Excel.

TABLE 26

IC$_{50}$ values (nM) for compounds of formula I:

| Compound of Example | IC$_{50}$ [nM] |
|---|---|
| 1 | 121 |
| 2 | 82 |
| 3 | 72 |
| 4 | 133 |
| 5 | 11 |
| 6 | 58 |
| 7 | 26 |
| 8 | 43 |
| 9 | 27 |
| 10 | 14 |
| 11 | 84 |
| 12 | 29 |
| 13 | 50 |
| 14 | 55 |
| 15 | 41 |
| 16 | 154 |
| 17 | 180 |
| 18 | 51 |
| 19 | 54 |
| 20 | 256 |
| 21 | 355 |
| 22 | 176 |
| 23 | 123 |
| 24 | 328 |
| 25 | 41 |
| 26 | 14 |
| 27 | 64 |
| 28 | 44 |
| 29 | 296 |
| 30 | 175 |
| 31 | 39 |
| 32 | 89 |
| 33 | 42 |
| 34 | 242 |
| 35 | 243 |
| 36 | 143 |
| 37 | 51 |
| 38 | 100 |
| 39 | 155 |
| 40 | 341 |
| 41 | 207 |
| 42 | 343 |
| 43 | 84 |
| 44 | 64 |
| 45 | 168 |
| 46 | 165 |
| 47 | 345 |
| 48 | 101 |
| 49 | 280 |
| 50 | 91 |
| 51 | 268 |
| 52 | 143 |
| 53 | 12 |
| 54 | <8 |
| 55 | 12 |
| 56 | 11 |
| 57 | 18 |
| 58 | 149 |
| 59 | 80 |
| 60 | 79 |
| 61 | 82 |

TABLE 26-continued

IC$_{50}$ values (nM) for compounds of formula I:

| Compound of Example | IC$_{50}$ [nM] |
|---|---|
| 62 | 70 |
| 63 | 85 |
| 64 | 12 |
| 65 | 21 |
| 66 | 14 |
| 67 | 40 |
| 68 | 17 |
| 69 | 41 |
| 70 | 20 |
| chloroquine | 6.8 |
| 71 | 167 |
| 72 | 152 |
| 73 | 42 |
| 74 | 41 |
| 75 | 30 |
| 76 | 50 |
| 77 | 53 |
| 78 | 12 |
| 79 | 21 |
| 80 | 105 |
| 81 | 122 |
| 82 | 140 |
| 83 | 120 |
| 84 | 42 |
| 85 | 43 |
| 86 | 43 |
| 87 | 28 |
| 88 | 21 |
| 89 | 337 |
| 90 | 138 |
| 91 | 291 |
| 92 | 269 |
| 93 | 418 |
| 94 | 286 |
| 95 | 13 |
| 96 | 351 |
| 97 | 120 |
| 98 | 370 |
| 99 | 43 |
| 100 | 21 |
| 101 | 43 |
| 102 | 81 |
| 103 | 44 |
| 104 | 60 |
| 105 | 152 |
| 106 | 348 |
| 107 | 420 |
| 108 | 430 |
| 109 | 393 |
| 110 | 171 |
| 111 | 165 |
| 112 | 39 |
| 113 | 78 |
| 114 | 86 |
| 115 | 82 |
| 116 | 70 |
| 117 | 305 |
| 118 | 83 |
| 119 | 46 |
| 120 | 90 |
| 121 | 76 |
| 122 | 43 |
| 123 | 21 |
| 124 | 303 |
| 125 | 340 |
| 126 | 30 |
| 127 | 184 |
| 128 | 302 |
| 129 | 21 |
| 130 | 42 |
| 131 | 303 |
| 132 | 22 |
| 133 | 69 |
| 134 | 213 |
| 135 | 84 |
| 136 | 80 |
| 137 | 47 |
| 138 | 344 |
| 139 | 355 |
| 140 | 354 |
| artesunate | 0.8 |
| 141 | 82 |
| 142 | 27 |
| 143 | 102 |
| 144 | 174 |
| 145 | 69 |
| 146 | 48 |
| 147 | 157 |
| 148 | 61 |
| 149 | 181 |
| 150 | 293 |
| 151 | 222 |
| 152 | 76 |
| 153 | 87 |
| 154 | 145 |
| 155 | 101 |
| 156 | 101 |
| 157 | 190 |
| 158 | 190 |
| 159 | 195 |
| 160 | 167 |
| 161 | 58 |
| 162 | 160 |
| 163 | 289 |
| 164 | 368 |
| 165 | 192 |
| 166 | 68 |
| 167 | 110 |
| 168 | 42 |
| 169 | 134 |
| 170 | 67 |
| 171 | 134 |
| 172 | 178 |
| 173 | 355 |
| 174 | 67 |
| 175 | 334 |
| 176 | 58 |
| 177 | 238 |
| 178 | 343 |
| 179 | 54 |
| 180 | 21 |
| 181 | 36 |
| 182 | 69 |
| 183 | 49 |
| 184 | 44 |
| 185 | 39 |
| 186 | 43 |
| 187 | 16 |
| 188 | 40 |
| 189 | 34 |
| 190 | 63 |
| 191 | 34 |
| 192 | 25 |
| 193 | 49 |
| 194 | 127 |
| 195 | 57 |
| 196 | 248 |
| 197 | 184 |
| 198 | 355 |
| 199 | 96 |
| 200 | 232 |
| 201 | 357 |
| 202 | 434 |
| 203 | 400 |
| 204 | 431 |
| 205 | 82 |
| 206 | 451 |
| 207 | 412 |

TABLE 26-continued

IC$_{50}$ values (nM) for compounds of formula I:

| Compound of Example | IC$_{50}$ [nM] |
|---|---|
| 208 | 82 |
| 209 | 172 |
| 210 | 174 |

The invention claimed is:

1. A compound of the formula I:

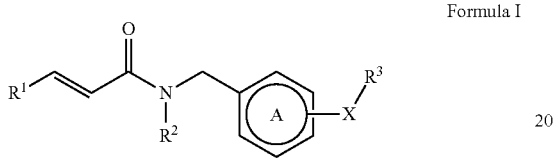

Formula I wherein
ring A is a phenylene or pyridin-diyl ring, wherein the group —X—R$^3$ is attached to ring A in meta- or para-position with respect to the point of attachment of ring A to the —CH$_2$— group;
R$^1$ represents phenyl, or 5- or 6-membered heteroaryl; wherein said phenyl or heteroaryl independently is unsubstituted, or mono-, di-, or tri-substituted, wherein the substituents are independently selected from (C$_{1-5}$)alkyl, (C$_{1-4}$)alkoxy, halogen, cyano, (C$_{1-3}$)fluoroalkyl, (C$_{1-3}$)fluoroalkoxy, and (C$_{1-3}$)alkyl-SO$_2$—;
X represents —NR$^4$— wherein R$^4$ represents hydrogen or (C$_{1-3}$)alkyl; —O—; or —(CO)—; and
R$^3$ represents
  piperidin-4-yl which is optionally substituted on the nitrogen with (C$_{1-4}$)alkyl;
  5- or 6-membered heteroaryl wherein said heteroaryl independently is unsubstituted, or mono-, or di-substituted wherein the substituents are independently selected from (C$_{1-4}$)alkyl, (C$_{1-4}$)alkoxy, halogen, (C$_{1-3}$)fluoroalkyl, and (C$_{1-3}$)fluoroalkoxy;
  8- to 10-membered heteroaryl wherein said heteroaryl independently is unsubstituted, or mono-, or di-substituted wherein the substituents are independently selected from (C$_{1-4}$)alkyl, (C$_{1-4}$)alkoxy, halogen, (C$_{1-3}$)fluoroalkyl, and (C$_{1-3}$)fluoroalkoxy;
  unsubstituted phenyl; or
  4-hydroxy-3-(diethylamino-methyl)-phenyl;
or X represents a direct bond and
R$^3$ represents
  4-[(C$_{1-4}$)alkyl]-piperazin-1-yl or pyrrolidine-1-yl; or
  5- or 6-membered heteroaryl, wherein said heteroaryl independently is unsubstituted, or mono-substituted with (C$_{1-4}$)alkyl;
or X represents —O— and R$^3$ represents —(C$_{2-4}$)alkylene-NR$^{10}$R$^{11}$, wherein R$^{10}$ and R$^{11}$ independently represent (C$_{1-3}$)alkyl; and
R$^2$ represents
  —(C$_{2-4}$)alkylene-NR$^{12}$R$^{13}$, wherein R$^{12}$ and R$^{13}$ independently represent (C$_{1-3}$)alkyl, or R$^{12}$ and R$^{13}$ together with the nitrogen atom to which they are attached to form a morpholine ring; or (C$_{3-7}$)cycloalkyl which is mono-substituted with NR$^{14}$R$^{15}$, wherein R$^{14}$ and R$^{15}$ independently represent (C$_{1-3}$)alkyl, or R$^{14}$ and R$^{15}$ together with the nitrogen atom to which they are attached to form a pyrrolidine ring; or
—(C$_{0-2}$)alkylene-heterocyclyl, wherein said heterocyclyl is a 4- to 7-membered saturated monocyclic or 7- to 11-membered saturated bicyclic carbocyclic ring containing one ring nitrogen atom; wherein said heterocyclyl may carry one optional substituent attached to a ring carbon atom wherein said substituent is selected from hydroxy and fluoro; and wherein said heterocyclyl is unsubstituted or substituted on said ring nitrogen atom with a substituent selected from:
  (C$_{1-6}$)alkyl,
  (C$_{2-3}$)fluoroalkyl;
  —(C$_{2-4}$)alkylene-(C$_{1-4}$)alkoxy;
  —(C$_{2-4}$)alkylene-NR$^{16}$R$^{17}$, wherein R$^{16}$ and R$^{17}$ independently represent (C$_{1-3}$)alkyl;
  (C$_{3-7}$)cycloalkyl;
  —(C$_{1-3}$)alkylene-(C$_{3-7}$)cycloalkyl;
  bicyclo [2.2.1]hept-5-en-2-ylmethyl;
  piperidin-4-yl, wherein said piperidin group is substituted at the nitrogen atom with (C$_{1-4}$)alkyl;
  2,2-diphenylethyl;
  3-diethylaminomethyl-4-hydroxy-benzyl;
  —(C$_{1-3}$)alkylene-phenyl wherein the phenyl group is optionally mono- or di-substituted wherein the substituents are independently selected from (C$_{1-4}$)alkyl, (C$_{1-4}$)alkoxy, halogen, cyano, (C$_{1-3}$)fluoroalkyl, and (C$_{1-3}$)fluoroalkoxy; and
  —(C$_{1-3}$)alkylene-heteroaryl, wherein the heteroaryl is a 5- to 10-membered heteroaryl, which is optionally mono- or di-substituted wherein the substituents are independently selected from (C$_{1-4}$)alkyl, (C$_{1-4}$)alkoxy, halogen, (C$_{1-3}$)fluoroalkyl, (C$_{1-3}$)fluoroalkoxy, phenyl, and —(CO)—(C$_{1-4}$)alkyl;
with the exception of:
N-[3-(4-morpholinyl)-propyl]-N-[(3-phenoxyphenyl)-methyl]-3-phenyl-2-propenamide; and
N-[2-(4-morpholinyl)-ethyl]-N-[(3-phenoxyphenyl)-methyl]-3-phenyl-2-propenamide;
or a pharmaceutically acceptable salt of such a compound.

2. A compound according to claim 1, which is also a compound of formula II

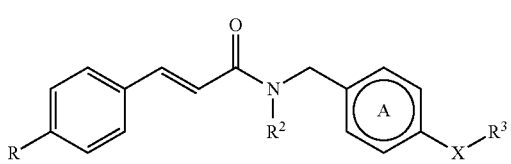

Formula II wherein
ring A is 1,4-phenylene, or pyridin-2,5-diyl;
R represents (C$_{1-5}$)alkyl, (C$_{1-4}$)alkoxy, halogen, cyano, (C$_{1-3}$)fluoroalkyl, (C$_{1-3}$)fluoroalkoxy, or (C$_{1-3}$)alkyl-SO$_2$—;
X represents —NR$^4$— wherein R$^4$ represents hydrogen or methyl; or —O—; and $R^3$ represents
  piperidin-4-yl which is optionally substituted on the nitrogen with $(C_{1-4})$alkyl;
  5- or 6-membered heteroaryl wherein said heteroaryl independently is unsubstituted, or mono-, or di-substituted wherein the substituents are independently selected from $(C_{1-4})$alkyl, $(C_{1-4})$alkoxy, and halogen;
  10-membered heteroaryl wherein said heteroaryl independently is unsubstituted, or mono-, or di-substituted wherein the substituents are independently selected from $(C_{1-4})$alkyl, $(C_{1-4})$alkoxy, halogen, and $(C_{1-3})$fluoroalkyl;
  unsubstituted phenyl; or
  4-hydroxy-3-(diethylamino-methyl)-phenyl;
or X represents a direct bond and
$R^3$ represents
  4-[$(C_{1-4})$alkyl]-piperazin-1-yl or pyrrolidine-1-yl; or
  5- or 6-membered heteroaryl, wherein said heteroaryl independently is unsubstituted, or mono-substituted with $(C_{1-4})$alkyl;
or X represents —O— and $R^3$ represents —$(C_{2-4})$alkylene-$NR^{10}R^{11}$, wherein $R^{10}$ and $R^{11}$ independently represent $(C_{1-3})$alkyl; and
$R^2$ represents
  —$(C_{2-4})$alkylene-$NR^{12}R^{13}$, wherein $R^{12}$ and $R^{13}$ independently represent $(C_{1-3})$alkyl, or $R^{12}$ and $R^{13}$ together with the nitrogen atom to which they are attached to form a morpholine ring; or
  $(C_{3-7})$cycloalkyl which is mono-substituted with $NR^{14}R^{15}$, wherein $R^{14}$ and $R^{15}$ independently represent $(C_{1-3})$alkyl, or $R^{14}$ and $R^{15}$ together with the nitrogen atom to which they are attached to form a pyrrolidine ring; or
  heterocyclyl, wherein said heterocyclyl is a 4- to 7-membered saturated monocyclic or 7- to 11-membered saturated bicyclic carbocyclic ring containing one ring nitrogen atom; wherein said heterocyclyl may carry one optional fluoro substituent attached to a ring carbon atom; and wherein said heterocyclyl is substituted on said ring nitrogen atom with a substituent selected from:
    $(C_{1-6})$alkyl,
    $(C_{2-3})$fluoroalkyl;
    —$(C_{2-4})$alkylene-$(C_{1-4})$alkoxy;
    —$(C_{2-4})$alkylene-$NR^{16}R^{17}$, wherein $R^{16}$ and $R^{17}$ independently represent $(C_{1-3})$alkyl;
    $(C_{3-7})$cycloalkyl;
    —$(C_{1-3})$alkylene-$(C_{3-7})$cycloalkyl;
    bicyclo[2.2.1]hept-5-en-2-ylmethyl;
    piperidin-4-yl, wherein said piperidin group is substituted at the nitrogen atom with $(C_{1-4})$alkyl;
    2,2-diphenylethyl;
    3-diethylaminomethyl-4-hydroxy-benzyl;
    —$(C_{1-3})$alkylene-phenyl wherein the phenyl group is optionally mono- or di-substituted wherein the substituents are independently selected from $(C_{1-4})$alkyl, $(C_{1-4})$alkoxy, halogen, cyano, and $(C_{1-3})$fluoroalkyl; and
    —$(C_{1-3})$alkylene-heteroaryl, wherein the heteroaryl is a 5- to 10-membered heteroaryl; wherein said heteroaryl is independently unsubstituted, or mono- or di-substituted wherein the substituents are independently selected from $(C_{1-4})$alkyl, phenyl, and —(CO)—$(C_{1-4})$alkyl;
or a pharmaceutically acceptable salt of such a compound.

3. A compound according to claim 1 wherein $R^1$ represents 4-trifluoromethylphenyl, or a pharmaceutically acceptable salt of such a compound.

4. A compound according to claim 1, wherein
X represents —$NR^4$— wherein $R^4$ represents hydrogen or methyl; and
$R^3$ represents
  piperidin-4-yl which is optionally substituted on the nitrogen with $(C_{1-3})$alkyl;
  6-membered heteroaryl selected from pyridinyl and pyrimidinyl, wherein said heteroaryl independently is unsubstituted, or mono-, or di-substituted wherein the substituents are independently selected from methyl, methoxy, and fluoro;
  quinolinyl which is mono-, or di-substituted wherein the substituents are independently selected from methyl, methoxy, chloro, and trifluoromethyl; or
  4-hydroxy-3-(diethylamino-methyl)-phenyl;
or X represents a direct bond and
$R^3$ represents
  4-[$(C_{1-4})$alkyl]-piperazin-1-yl or pyrrolidine-1-yl; or
  5- or 6-membered heteroaryl selected from pyridinyl, pyrimidinyl, pyrazolyl, and thiazolyl, wherein said heteroaryl independently is unsubstituted, or mono-substituted with methyl;
or X represents —O— and $R^3$ represents dimethylaminopropyl;
or a pharmaceutically acceptable salt of such a compound.

5. A compound according to claim 1, wherein
X represents —$NR^4$— wherein $R^4$ represents hydrogen or methyl; and
$R^3$ represents
  piperidin-4-yl which is optionally substituted on the nitrogen with $(C_{1-3})$alkyl; or
  6-membered heteroaryl selected from pyridinyl and pyrimidinyl, wherein said heteroaryl independently is unsubstituted, or mono-, or di-substituted wherein the substituents are independently selected from methyl, methoxy, and fluoro;
or a pharmaceutically acceptable salt of such a compound.

6. A compound according to claim 1, wherein $R^2$ represents heterocyclyl selected from azetidinyl, pyrrolidinyl, piperidinyl, azepanyl, 2-aza-spiro[3.3]hept-6-yl, octahydro-cyclopenta[c]pyrrol-5-yl, and 3-aza-spiro[5.5]undec-9-yl; wherein in case said herocyclyl is piperidinyl, said heterocyclyl may carry one optional fluoro substituent attached to a ring carbon atom; wherein said heterocyclyl is substituted on the ring nitrogen atom with a substituent selected from:
  methyl, ethyl, iso-propyl, n-propyl, 3-methylbutyl;
  3,3,3-trifluoropropyl;
  2-methoxy-1-methyl-ethyl;
  2-dimethylamino-ethyl;
  cyclopropyl, cyclopentyl;
  cyclopropyl-methyl;
  bicyclo[2.2.1]hept-5-en-2-ylmethyl;
  1-methyl-piperidin-4-yl;
  —$(C_{1-3})$alkylene-phenyl wherein the phenyl group is optionally mono- or di-substituted wherein the substituents are independently selected from methyl, methoxy, halogen, cyano, and trifluoromethyl; and
  —$(CH_2)$-heteroaryl, wherein the heteroaryl is a 5- to 10-membered heteroaryl selected from thiazolyl, isoxazolyl, oxazolyl, pyrazolyl, imidazolyl, pyridinyl, pyrimidinyl, imidazopyridinyl, benzimidazolyl, and indolyl; wherein said heteroaryl is independently unsubstituted or mono- or di-substituted with methyl;
or a pharmaceutically acceptable salt of such a compound.

7. A compound according to claim 1, wherein R² represents heterocyclyl selected from piperidin-3-yl, piperidin-4-yl, 3-fluoro-piperidin-4-yl, 2-aza-spiro[3.3]hept-6-yl, and 3-aza-spiro[5.5]undec-9-yl; wherein said heterocyclyl is independently substituted on the ring nitrogen atom with with cyclopentyl or 1-methyl-piperidin-4-yl;
or a pharmaceutically acceptable salt of such a compound.

8. A compound according to claim 1 which is selected from the group consisting of:
- (E)-N-[4-(Methyl-pyridin-4-yl-amino)-benzyl]-N-piperidin-4-yl-3-(4-trifluoromethyl-phenyl)-acrylamide;
- (E)-N-[4-(Methyl-pyridin-4-yl-amino)-benzyl]-N—(S)-piperidin-3-yl-3-(4-trifluoromethyl-phenyl)-acrylamide;
- (E)-N-[4-(Methyl-pyridin-4-yl-amino)-benzyl]-N-[1-(4-trifluoromethyl-benzyl)-piperidin-4-yl]-3-(4-trifluoromethyl-phenyl)-acrylamide;
- (E)-N-[1-(2-Methyl-oxazol-4-ylmethyl)-piperidin-4-yl]-N-[4-(methyl-pyridin-4-yl-amino)-benzyl]-3-(4-trifluoromethyl-phenyl)-acrylamide;
- (E)-N-(1-Cyclopentyl-piperidin-4-yl)-N-[4-(methyl-pyridin-4-yl-amino)-benzyl]-3-(4-trifluoromethyl-phenyl)-acrylamide;
- (E)-N-(1-Benzyl-piperidin-4-yl)-N-[4-(methyl-pyridin-4-yl-amino)-benzyl]-3-(4-trifluoromethyl-phenyl)-acrylamide;
- (E)-N-(1-Ethyl-piperidin-4-yl)-N-[4-(methyl-pyridin-4-yl-amino)-benzyl]-3-(4-trifluoromethyl-phenyl)-acrylamide;
- (E)-N-[1-(3-Methyl-butyl)-piperidin-4-yl]-N-[4-(methyl-pyridin-4-yl-amino)-benzyl]-3-(4-trifluoromethyl-phenyl)-acrylamide;
- (E)-N-(1-Cyclopropylmethyl-piperidin-4-yl)-N-[4-(methyl-pyridin-4-yl-amino)-benzyl]-3-(4-trifluoromethyl-phenyl)-acrylamide;
- (E)-N-(1'-Bicyclo[2.2.1]hept-5-en-2-ylmethyl-piperidin-4-yl)-N-[4-(methyl-pyridin-4-yl-amino)-benzyl]-3-(4-trifluoromethyl-phenyl)-acrylamide;
- (E)-N-[1-(3,4-Dichloro-benzyl)-piperidin-4-yl]-N-[4-(methyl-pyridin-4-yl-amino)-benzyl]-3-(4-trifluoromethyl-phenyl)-acrylamide;
- (E)-N-[1-(4-Methyl-benzyl)-piperidin-4-yl]-N-[4-(methyl-pyridin-4-yl-amino)-benzyl]-3-(4-trifluoromethyl-phenyl)-acrylamide;
- (E)-N-[1-(4-Methoxy-benzyl)-piperidin-4-yl]-N-[4-(methyl-pyridin-4-yl-amino)-benzyl]-3-(4-trifluoromethyl-phenyl)-acrylamide;
- (E)-N-[4-(Methyl-pyridin-4-yl-amino)-benzyl]-N-(1-phenethyl-piperidin-4-yl)-3-(4-trifluoromethyl-phenyl)-acrylamide;
- (E)-N-[1-(2,2-Diphenyl-ethyl)-piperidin-4-yl]-N-[4-(methyl-pyridin-4-yl-amino)-benzyl]-3-(4-trifluoromethyl-phenyl)-acrylamide;
- (E)-N-[4-(Methyl-pyridin-4-yl-amino)-benzyl]-3-(4-trifluoromethyl-phenyl)-N-[1-(3,3,3-trifluoro-propyl)-piperidin-4-yl]-acrylamide;
- (E)-N-[1-(2-Methyl-2H-pyrazol-3-ylmethyl)-piperidin-4-yl]-N-[4-(methyl-pyridin-4-yl-amino)-benzyl]-3-(4-trifluoromethyl-phenyl)-acrylamide;
- (E)-N-[4-(Methyl-pyridin-4-yl-amino)-benzyl]-N-[1-(1-phenyl-1H-pyrazol-4-ylmethyl)-piperidin-4-yl]-3-(4-trifluoromethyl-phenyl)-acrylamide;
- (E)-N-[1-(3-Methyl-3H-imidazol-4-ylmethyl)-piperidin-4-yl]-N-[4-(methyl-pyridin-4-yl-amino)-benzyl]-3-(4-trifluoromethyl-phenyl)-acrylamide;
- (E)-N-(1-Imidazo[1,5-a]pyridin-3-ylmethyl-piperidin-4-yl)-N-[4-(methyl-pyridin-4-yl-amino)-benzyl]-3-(4-trifluoromethyl-phenyl)-acrylamide;
- (E)-N-[1-(1-Methyl-1H-benzoimidazol-2-ylmethyl)-piperidin-4-yl]-N-[4-(methyl-pyridin-4-yl-amino)-benzyl]-3-(4-trifluoromethyl-phenyl)-acrylamide;
- (E)-N-[4-(Methyl-pyridin-4-yl-amino)-benzyl]-N-(1-pyridin-2-ylmethyl-piperidin-4-yl)-3-(4-trifluoromethyl-phenyl)-acrylamide;
- (E)-N-[4-(Methyl-pyridin-4-yl-amino)-benzyl]-N-(1-pyridin-3-ylmethyl-piperidin-4-yl)-3-(4-trifluoromethyl-phenyl)-acrylamide;
- (E)-N-[4-(Methyl-pyridin-4-yl-amino)-benzyl]-N-[1-(2-methyl-pyrimidin-5-ylmethyl)-piperidin-4-yl]-3-(4-trifluoromethyl-phenyl)-acrylamide;
- (E)-N-(1-Imidazo[1,2-a]pyridin-7-ylmethyl-piperidin-4-yl)-N-[4-(methyl-pyridin-4-yl-amino)-benzyl]-3-(4-trifluoromethyl-phenyl)-acrylamide;
- (E)-N-(1'-Methyl-[1,4']bipiperidinyl-4-yl)-N-[4-(methyl-pyridin-4-yl-amino)-benzyl]-3-(4-trifluoromethyl-phenyl)-acrylamide;
- (E)-N-[1-(4-Cyano-benzyl)-piperidin-4-yl]-N-[4-(methyl-pyridin-4-yl-amino)-benzyl]-3-(4-trifluoromethyl-phenyl)-acrylamide;
- (E)-N-[1-(1-Acetyl-1H-indol-3-ylmethyl)-piperidin-4-yl]-N-[4-(methyl-pyridin-4-yl-amino)-benzyl]-3-(4-trifluoromethyl-phenyl)-acrylamide;
- (E)-N-[4-(Methyl-pyridin-4-yl-amino)-benzyl]-N-(1-pyrimidin-2-ylmethyl-piperidin-4-yl)-3-(4-trifluoromethyl-phenyl)-acrylamide;
- (E)-N-[4-(Methyl-pyridin-4-yl-amino)-benzyl]-N-[1-(1-phenyl-ethyl)-piperidin-4-yl]-3-(4-trifluoromethyl-phenyl)-acrylamide;
- (E)-N-(1-Cyclopropylmethyl-piperidin-4-yl)-N-[4-(2-methyl-pyridin-4-ylamino)-benzyl]-3-(4-trifluoromethyl-phenyl)-acrylamide;
- (E)-N-[1-(2,5-Dimethyl-oxazol-4-ylmethyl)-piperidin-4-yl]-N-[4-(2-methyl-pyridin-4-ylamino)-benzyl]-3-(4-trifluoromethyl-phenyl)-acrylamide;
- (E)-N-[4-(2-Methyl-pyridin-4-ylamino)-benzyl]-N-(1-propyl-piperidin-4-yl)-3-(4-trifluoromethyl-phenyl)-acrylamide;
- (E)-N-[1-(5-Methyl-isoxazol-3-ylmethyl)-piperidin-4-yl]-N-[4-(2-methyl-pyridin-4-ylamino)-benzyl]-3-(4-trifluoromethyl-phenyl)-acrylamide;
- (E)-N-[4-(2-Methyl-pyridin-4-ylamino)-benzyl]-N-[1-(4-methyl-thiazol-5-ylmethyl)-piperidin-4-yl]-3-(4-trifluoromethyl-phenyl)-acrylamide;
- (E)-N-[1-(2-Methyl-oxazol-4-ylmethyl)-piperidin-4-yl]-N-[4-(2-methyl-pyridin-4-ylamino)-benzyl]-3-(4-trifluoromethyl-phenyl)-acrylamide;
- (E)-N-(1-Benzyl-piperidin-4-yl)-N-[4-(2-methyl-pyridin-4-ylamino)-benzyl]-3-(4-trifluoromethyl-phenyl)-acrylamide;
- (E)-N-(1-Imidazo[1,2-a]pyridin-3-ylmethyl-piperidin-4-yl)-N-[4-(2-methyl-pyridin-4-ylamino)-benzyl]-3-(4-trifluoromethyl-phenyl)-acrylamide;
- (E)-N-[4-(2-Methyl-pyridin-4-ylamino)-benzyl]-3-(4-trifluoromethyl-phenyl)-N-[1-(3,3,3-trifluoro-propyl)-piperidin-4-yl]-acrylamide;
- (E)-N-[4-(2-Methyl-pyridin-4-ylamino)-benzyl]-N-(1-thiazol-2-ylmethyl-piperidin-4-yl)-3-(4-trifluoromethyl-phenyl)-acrylamide;
- (E)-N-[1-(1-Methyl-1H-imidazol-2-ylmethyl)-piperidin-4-yl]-N-[4-(2-methyl-pyridin-4-ylamino)-benzyl]-3-(4-trifluoromethyl-phenyl)-acrylamide;

(E)-N-[4-(2-Methyl-pyridin-4-ylamino)-benzyl]-N-[1-(4-methyl-thiazol-2-ylmethyl)-piperidin-4-yl]-3-(4-trifluoromethyl-phenyl)-acrylamide;

(E)-N-[1-(2,5-Dimethyl-2H-pyrazol-3-ylmethyl)-piperidin-4-yl]-N-[4-(2-methyl-pyridin-4-ylamino)-benzyl]-3-(4-trifluoromethyl-phenyl)-acrylamide;

(E)-N-[1-(3,5-Dimethyl-isoxazol-4-ylmethyl)-piperidin-4-yl]-N-[4-(2-methyl-pyridin-4-ylamino)-benzyl]-3-(4-trifluoromethyl-phenyl)-acrylamide;

(E)-N-(1-Imidazo[1,5-a]pyridin-1-ylmethyl-piperidin-4-yl)-N-[4-(2-methyl-pyridin-4-ylamino)-benzyl]-3-(4-trifluoromethyl-phenyl)-acrylamide;

(E)-N-(1-Imidazo[1,5-a]pyridin-3-ylmethyl-piperidin-4-yl)-N-[4-(2-methyl-pyridin-4-ylamino)-benzyl]-3-(4-trifluoromethyl-phenyl)-acrylamide;

(E)-N-[4-(2-Methyl-pyridin-4-ylamino)-benzyl]-N-(1-pyrimidin-2-ylmethyl-piperidin-4-yl)-3-(4-trifluoromethyl-phenyl)-acrylamide;

(E)-N-[4-(2-Methyl-pyridin-4-ylamino)-benzyl]-N-(1-pyridin-3-ylmethyl-piperidin-4-yl)-3-(4-trifluoromethyl-phenyl)-acrylamide;

(E)-N-[4-(2-Methyl-pyridin-4-ylamino)-benzyl]-N-(1-pyrimidin-5-ylmethyl-piperidin-4-yl)-3-(4-trifluoromethyl-phenyl)-acrylamide;

(E)-N-[1-(1-Methyl-1H-pyrazol-4-ylmethyl)-piperidin-4-yl]-N-[4-(2-methyl-pyridin-4-ylamino)-benzyl]-3-(4-trifluoromethyl-phenyl)-acrylamide;

(E)-N-[4-(2-Methyl-pyridin-4-ylamino)-benzyl]-N-[1-(2-methyl-pyrimidin-5-ylmethyl)-piperidin-4-yl]-3-(4-trifluoromethyl-phenyl)-acrylamide;

(E)-N-[1-(2,3-Dimethyl-3H-imidazol-4-ylmethyl)-piperidin-4-yl]-N-[4-(2-methyl-pyridin-4-ylamino)-benzyl]-3-(4-trifluoromethyl-phenyl)-acrylamide;

(E)-N-[1-(3-Dimethylaminomethyl-4-hydroxy-benzyl)-piperidin-4-yl]-N-[4-(2-methyl-pyridin-4-ylamino)-benzyl]-3-(4-trifluoromethyl-phenyl)-acrylamide;

(E)-N-[1-(3-Diethylaminomethyl-4-hydroxy-benzyl)-piperidin-4-yl]-N-[4-(2-methyl-pyridin-4-ylamino)-benzyl]-3-(4-trifluoromethyl-phenyl)-acrylamide;

(E)-N—((S)-1'-Methyl-[1,4']bipiperidinyl-3-yl)-N-[4-(methyl-pyridin-4-yl-amino)-benzyl]-3-(4-trifluoromethyl-phenyl)-acrylamide;

(E)-N—((R)-1'-Methyl-[1,4']bipiperidinyl-3-yl)-N-[4-(methyl-pyridin-4-yl-amino)-benzyl]-3-(4-trifluoromethyl-phenyl)-acrylamide;

(E)-N-[1-(1-Methyl-piperidin-4-yl)-azepan-4-yl]-N-[4-(methyl-pyridin-4-yl-amino)-benzyl]-3-(4-trifluoromethyl-phenyl)-acrylamide;

(E)-N—((S)-1-Cyclopentyl-piperidin-3-yl)-N-[4-(methyl-pyridin-4-yl-amino)-benzyl]-3-(4-trifluoromethyl-phenyl)-acrylamide;

(E)-N—((R)-1-Cyclopentyl-piperidin-3-yl)-N-[4-(methyl-pyridin-4-yl-amino)-benzyl]-3-(4-trifluoromethyl-phenyl)-acrylamide;

(E)-N-(1-Cyclopentyl-azepan-4-yl)-N-[4-(methyl-pyridin-4-yl-amino)-benzyl]-3-(4-trifluoromethyl-phenyl)-acrylamide;

(E)-N—[(S)-1-(3-Methyl-butyl)-piperidin-3-yl]-N-[4-(methyl-pyridin-4-yl-amino)-benzyl]-3-(4-trifluoromethyl-phenyl)-acrylamide;

(E)-N—[(R)-1-(3-Methyl-butyl)-piperidin-3-yl]-N-[4-(methyl-pyridin-4-yl-amino)-benzyl]-3-(4-trifluoromethyl-phenyl)-acrylamide;

(E)-N-[1-(3-Methyl-butyl)-azepan-4-yl]-N-[4-(methyl-pyridin-4-yl-amino)-benzyl]-3-(4-trifluoromethyl-phenyl)-acrylamide;

(E)-N-[(3aR,6aS)-2-(1-Methyl-piperidin-4-yl)-octahydro-cyclopenta[c]pyrrol-5-yl]-N-[4-(methyl-pyridin-4-yl-amino)-benzyl]-3-(4-trifluoromethyl-phenyl)-acrylamide;

(E)-N-[3-(1-Methyl-piperidin-4-yl)-3-aza-spiro[5.5]undec-9-yl]-N-[4-(methyl-pyridin-4-yl-amino)-benzyl]-3-(4-trifluoromethyl-phenyl)-acrylamide;

(E)-N-((3aR,6aS)-2-Cyclopentyl-octahydro-cyclopenta[c]pyrrol-5-yl)-N-[4-(methyl-pyridin-4-yl-amino)-benzyl]-3-(4-trifluoromethyl-phenyl)-acrylamide;

(E)-N-(3-Cyclopentyl-3-aza-spiro[5.5]undec-9-yl)-N-[4-(methyl-pyridin-4-yl-amino)-benzyl]-3-(4-trifluoromethyl-phenyl)-acrylamide;

(E)-N-[(3aR,6aS)-2-(3-Methyl-butyl)-octahydro-cyclopenta[c]pyrrol-5-yl]-N-[4-(methyl-pyridin-4-yl-amino)-benzyl]-3-(4-trifluoromethyl-phenyl)-acrylamide;

(E)-N-[3-(3-Methyl-butyl)-3-aza-spiro[5.5]undec-9-yl]-N-[4-(methyl-pyridin-4-yl-amino)-benzyl]-3-(4-trifluoromethyl-phenyl)-acrylamide;

(E)-N-[1-(1-Methyl-piperidin-4-yl)-azepan-3-yl]-N-[4-(methyl-pyridin-4-yl-amino)-benzyl]-3-(4-trifluoromethyl-phenyl)-acrylamide;

(E)-N-(1-Cyclopentyl-azepan-3-yl)-N-[4-(methyl-pyridin-4-yl-amino)-benzyl]-3-(4-trifluoromethyl-phenyl)-acrylamide;

(E)-N-[1-(3-Methyl-butyl)-azepan-3-yl]-N-[4-(methyl-pyridin-4-yl-amino)-benzyl]-3-(4-trifluoromethyl-phenyl)-acrylamide;

(E)-N-[2-(1-Methyl-piperidin-4-yl)-2-aza-spiro[3.3]hept-6-yl]-N-[4-(methyl-pyridin-4-yl-amino)-benzyl]-3-(4-trifluoromethyl-phenyl)-acrylamide;

(E)-N-(2-Cyclopentyl-2-aza-spiro[3.3]hept-6-yl)-N-[4-(methyl-pyridin-4-yl-amino)-benzyl]-3-(4-trifluoromethyl-phenyl)-acrylamide;

(E)-N-[2-(3-Methyl-butyl)-2-aza-spiro[3.3]hept-6-yl]-N-[4-(methyl-pyridin-4-yl-amino)-benzyl]-3-(4-trifluoromethyl-phenyl)-acrylamide;

(E)-N-((3R,4S)-1-Cyclopentyl-3-fluoro-piperidin-4-yl)-N-[4-(methyl-pyridin-4-yl-amino)-benzyl]-3-(4-trifluoromethyl-phenyl)-acrylamide;

(E)-N-[(3R,4S)-3-Fluoro-1-(3-methyl-butyl)-piperidin-4-yl]-N-[4-(methyl-pyridin-4-yl-amino)-benzyl]-3-(4-trifluoromethyl-phenyl)-acrylamide;

(E)-N-((3R,4S)-3-Fluoro-1'-methyl-[1,4']bipiperidinyl-4-yl)-N-[4-(methyl-pyridin-4-yl-amino)-benzyl]-3-(4-trifluoromethyl-phenyl)-acrylamide;

(E)-N-((3S,4S)-3-Fluoro-1'-methyl-[1,4']bipiperidinyl-4-yl)-N-[4-(methyl-pyridin-4-yl-amino)-benzyl]-3-(4-trifluoromethyl-phenyl)-acrylamide;

(E)-N-((3S,4S)-1-Cyclopentyl-3-fluoro-piperidin-4-yl)-N-[4-(methyl-pyridin-4-yl-amino)-benzyl]-3-(4-trifluoromethyl-phenyl)-acrylamide;

(E)-N-[(3S,4S)-3-Fluoro-1-(3-methyl-butyl)-piperidin-4-yl]-N-[4-(methyl-pyridin-4-yl-amino)-benzyl]-3-(4-trifluoromethyl-phenyl)-acrylamide;

(E)-N—((S)-1-Ethyl-piperidin-3-yl)-N-[4-(methyl-pyridin-4-yl-amino)-benzyl]-3-(4-trifluoromethyl-phenyl)-acrylamide;

(E)-N—((S)-1-Isopropyl-piperidin-3-yl)-N-[4-(methyl-pyridin-4-yl-amino)-benzyl]-3-(4-trifluoromethyl-phenyl)-acrylamide;

(E)-N-[1-(2-Methoxy-1-methyl-ethyl)-piperidin-4-yl]-N-[4-(2-methyl-pyridin-4-ylamino)-benzyl]-3-(4-trifluoromethyl-phenyl)-acrylamide;

(E)-N-(1-Cyclopentyl-piperidin-4-yl)-N-[4-(2-methyl-quinolin-4-ylamino)-benzyl]-3-(4-trifluoromethyl-phenyl)-acrylamide;

(E)-N-(1-Cyclopentyl-piperidin-4-yl)-N-[4-(pyridin-4-ylamino)-benzyl]-3-(4-trifluoromethyl-phenyl)-acrylamide;

(E)-N-(1-Cyclopentyl-piperidin-4-yl)-N-[4-(2,6-dimethyl-pyridin-4-ylamino)-benzyl]-3-(4-trifluoromethyl-phenyl)-acrylamide;

(E)-N-(1-Cyclopentyl-piperidin-4-yl)-N-[4-(6-methoxy-quinolin-4-ylamino)-benzyl]-3-(4-trifluoromethyl-phenyl)-acrylamide;

(E)-N-[4-(2,8-Bis-trifluoromethyl-quinolin-4-ylamino)-benzyl]-N-(1-cyclopentyl-piperidin-4-yl)-3-(4-trifluoromethyl-phenyl)-acrylamide;

(E)-N-(1-Cyclopentyl-piperidin-4-yl)-3-(4-trifluoromethyl-phenyl)-N-[4-(7-trifluoromethyl-quinolin-4-ylamino)-benzyl]-acrylamide;

(E)-N-(1-Cyclopentyl-piperidin-4-yl)-N-[4-(pyrimidin-5-ylamino)-benzyl]-3-(4-trifluoromethyl-phenyl)-acrylamide;

(E)-N-(1-Cyclopentyl-piperidin-4-yl)-N-[4-(pyrimidin-4-ylamino)-benzyl]-3-(4-trifluoromethyl-phenyl)-acrylamide;

(E)-N-(1-Cyclopentyl-piperidin-4-yl)-N-(4-phenylamino-benzyl)-3-(4-trifluoromethyl-phenyl)-acrylamide;

(E)-N-(1-Cyclopentyl-piperidin-4-yl)-N-[4-(2-methoxy-pyridin-4-ylamino)-benzyl]-3-(4-trifluoromethyl-phenyl)-acrylamide;

(E)-N-(1-Cyclopentyl-piperidin-4-yl)-N-[4-(2-methyl-pyridin-4-ylamino)-benzyl]-3-(4-trifluoromethyl-phenyl)-acrylamide;

(E)-N-(1-Cyclopentyl-piperidin-4-yl)-N-[4-(methyl-pyridin-3-yl-amino)-benzyl]-3-(4-trifluoromethyl-phenyl)-acrylamide;

(E)-N-[4-(7-Chloro-quinolin-4-ylamino)-benzyl]-N-(1-cyclopentyl-piperidin-4-yl)-3-(4-trifluoromethyl-phenyl)-acrylamide;

(E)-N-(1-Cyclopentyl-piperidin-4-yl)-N-[4-(5-methyl-pyridin-2-ylamino)-benzyl]-3-(4-trifluoromethyl-phenyl)-acrylamide;

(E)-N-(1-Cyclopentyl-pyrrolidin-3-yl)-N-[4-(methyl-pyridin-4-yl-amino)-benzyl]-3-(4-trifluoromethyl-phenyl)-acrylamide;

(E)-N-(1-Cyclopentyl-piperidin-4-yl)-N-[4-(6-methoxy-2-methyl-quinolin-4-ylamino)-benzyl]-3-(4-trifluoromethyl-phenyl)-acrylamide;

(E)-N-(1-Cyclopentyl-pyrrolidin-3-yl)-N-[4-(2-methyl-pyridin-4-ylamino)-benzyl]-3-(4-trifluoromethyl-phenyl)-acrylamide;

(E)-N-(1-Cyclopentyl-azetidin-3-yl)-N-[4-(methyl-pyridin-4-yl-amino)-benzyl]-3-(4-trifluoromethyl-phenyl)-acrylamide;

(E)-N-(1-Cyclopentyl-piperidin-4-yl)-N-[6-(pyridin-4-ylamino)-pyridin-3-ylmethyl]-3-(4-trifluoromethyl-phenyl)-acrylamide;

(E)-N-(1-Cyclopentyl-piperidin-4-yl)-N-[6-(methyl-pyridin-4-yl-amino)-pyridin-3-ylmethyl]-3-(4-trifluoromethyl-phenyl)-acrylamide;

(E)-N-(1-Cyclopentyl-piperidin-4-yl)-N-[6-(1-methyl-piperidin-4-ylamino)-pyridin-3-ylmethyl]-3-(4-trifluoromethyl-phenyl)-acrylamide;

(E)-N-(1-Cyclopentyl-piperidin-4-yl)-N-{6-[methyl-(1-methyl-piperidin-4-yl)-amino]-pyridin-3-ylmethyl}-3-(4-trifluoromethyl-phenyl)-acrylamide;

(E)-N-(1-Cyclopentyl-piperidin-4-yl)-N-[6-(pyrimidin-4-ylamino)-pyridin-3-ylmethyl]-3-(4-trifluoromethyl-phenyl)-acrylamide;

(E)-N-(1-Cyclopentyl-piperidin-4-yl)-N-[6-(2-methyl-pyrimidin-4-ylamino)-pyridin-3-ylmethyl]-3-(4-trifluoromethyl-phenyl)-acrylamide;

(E)-N-(1-Cyclopentyl-piperidin-4-yl)-N-[6-(6-methyl-pyrimidin-4-ylamino)-pyridin-3-ylmethyl]-3-(4-trifluoromethyl-phenyl)-acrylamide;

(E)-N-(1'-Methyl-[1,4']bipiperidinyl-4-yl)-N-[6-(pyridin-4-ylamino)-pyridin-3-ylmethyl]-3-(4-trifluoromethyl-phenyl)-acrylamide;

(E)-N-(1'-Methyl-[1,4']bipiperidinyl-4-yl)-N-[6-(2-methyl-pyridin-4-ylamino)-pyridin-3-ylmethyl]-3-(4-trifluoromethyl-phenyl)-acrylamide;

(E)-N-(1'-Methyl-[1,4']bipiperidinyl-4-yl)-N-[6-(methyl-pyridin-4-yl-amino)-pyridin-3-ylmethyl]-3-(4-trifluoromethyl-phenyl)-acrylamide;

(E)-N-((R)-1-Cyclopentyl-pyrrolidin-3-yl)-N-[4-(methyl-pyridin-4-yl-amino)-benzyl]-3-(4-trifluoromethyl-phenyl)-acrylamide;

(E)-N-((S)-1-Cyclopentyl-pyrrolidin-3-yl)-N-[4-(methyl-pyridin-4-yl-amino)-benzyl]-3-(4-trifluoromethyl-phenyl)-acrylamide;

(E)-N-(1'-Methyl-[1,4']bipiperidinyl-4-yl)-N-[4-(pyridin-4-ylamino)-benzyl]-3-(4-trifluoromethyl-phenyl)-acrylamide;

(E)-N-(1'-Methyl-[1,4']bipiperidinyl-4-yl)-N-[4-(2-methyl-pyridin-4-ylamino)-benzyl]-3-(4-trifluoromethyl-phenyl)-acrylamide;

(E)-3-(4-Chloro-phenyl)-N-(1'-methyl-[1,4']bipiperidinyl-4-yl)-N-[4-(2-methyl-pyridin-4-ylamino)-benzyl]-acrylamide;

(E)-N-(1'-Methyl-[1,4']bipiperidinyl-4-yl)-N-[4-(pyridin-4-ylamino)-benzyl]-3-(4-trifluoromethoxy-phenyl)-acrylamide;

(E)-N-(1'-Methyl-[1,4']bipiperidinyl-4-yl)-N-[4-(2-methyl-pyridin-4-ylamino)-benzyl]-3-(4-trifluoromethoxy-phenyl)-acrylamide;

(E)-N-((S)-1-Isopropyl-piperidin-3-yl)-N-[6-(2-methyl-pyridin-4-ylamino)-pyridin-3-ylmethyl]-3-(4-trifluoromethyl-phenyl)-acrylamide;

(E)-N-(1-Isopropyl-piperidin-4-yl)-N-{3-[methyl-(2-methyl-pyridin-4-yl)-amino]-benzyl}-3-(4-trifluoromethyl-phenyl)-acrylamide;

(E)-N-(1-Isopropyl-piperidin-4-yl)-N-[3-(2-methyl-pyridin-4-ylamino)-benzyl]-3-(4-trifluoromethyl-phenyl)-acrylamide;

(E)-N-(1-Isopropyl-piperidin-4-yl)-N-[3-(3-methyl-pyridin-4-ylamino)-benzyl]-3-(4-trifluoromethyl-phenyl)-acrylamide;

(E)-N-[3-(3-Fluoro-pyridin-4-ylamino)-benzyl]-N-(1-isopropyl-piperidin-4-yl)-3-(4-trifluoromethyl-phenyl)-acrylamide;

(E)-N-(1-Isopropyl-piperidin-4-yl)-N-[3-(pyrimidin-4-ylamino)-benzyl]-3-(4-trifluoromethyl-phenyl)-acrylamide;

(E)-N-(1-Isopropyl-piperidin-4-yl)-N-[3-(pyridin-4-ylamino)-benzyl]-3-(4-trifluoromethyl-phenyl)-acrylamide;

(E)-N-(1-Isopropyl-piperidin-4-yl)-N-[6-(methyl-pyridin-4-yl-amino)-pyridin-2-ylmethyl]-3-(4-trifluoromethyl-phenyl)-acrylamide;

(E)-N-(1-Isopropyl-piperidin-4-yl)-N-{6-[methyl-(2-methyl-pyridin-4-yl)-amino]-pyridin-2-ylmethyl}-3-(4-trifluoromethyl-phenyl)-acrylamide;

(E)-N-(1-Isopropyl-piperidin-4-yl)-N-[6-(2-methyl-pyridin-4-ylamino)-pyridin-2-ylmethyl]-3-(4-trifluoromethyl-phenyl)-acrylamide;
(E)-N-(1-Isopropyl-piperidin-4-yl)-N-[6-(3-methyl-pyridin-4-ylamino)-pyridin-2-ylmethyl]-3-(4-trifluoromethyl-phenyl)-acrylamide;
(E)-N-[6-(3-Fluoro-pyridin-4-ylamino)-pyridin-2-ylmethyl]-N-(1-isopropyl-piperidin-4-yl)-3-(4-trifluoromethyl-phenyl)-acrylamide;
(E)-N-(1-Isopropyl-piperidin-4-yl)-N-[6-(pyridin-4-ylamino)-pyridin-2-ylmethyl]-3-(4-trifluoromethyl-phenyl)-acrylamide;
(E)-N-(1-Isopropyl-piperidin-4-yl)-N-[5-(methyl-pyridin-4-yl-amino)-pyridin-3-ylmethyl]-3-(4-trifluoromethyl-phenyl)-acrylamide;
(E)-N-(1-Isopropyl-piperidin-4-yl)-N-[5-(methyl-pyridin-3-yl-amino)-pyridin-3-ylmethyl]-3-(4-trifluoromethyl-phenyl)-acrylamide;
(E)-N-(1-Isopropyl-piperidin-4-yl)-N-{5-[methyl-(2-methyl-pyridin-4-yl)-amino]-pyridin-3-ylmethyl}-3-(4-trifluoromethyl-phenyl)-acrylamide;
(E)-N-(1-Isopropyl-piperidin-4-yl)-N-[5-(2-methyl-pyridin-4-ylamino)-pyridin-3-ylmethyl]-3-(4-trifluoromethyl-phenyl)-acrylamide;
(E)-N-(1-Isopropyl-piperidin-4-yl)-N-[5-(3-methyl-pyridin-4-ylamino)-pyridin-3-ylmethyl]-3-(4-trifluoromethyl-phenyl)-acrylamide;
(E)-N-[5-(3-Fluoro-pyridin-4-ylamino)-pyridin-3-ylmethyl]-N-(1-isopropyl-piperidin-4-yl)-3-(4-trifluoromethyl-phenyl)-acrylamide;
(E)-N-(1-Isopropyl-piperidin-4-yl)-N-[5-(pyrimidin-4-ylamino)-pyridin-3-ylmethyl]-3-(4-trifluoromethyl-phenyl)-acrylamide;
(E)-N-(1-Isopropyl-piperidin-4-yl)-N-[5-(methyl-pyridin-2-yl-amino)-pyridin-3-ylmethyl]-3-(4-trifluoromethyl-phenyl)-acrylamide;
(E)-N-(1-Isopropyl-piperidin-4-yl)-N-[5-(pyridin-4-ylamino)-pyridin-3-ylmethyl]-3-(4-trifluoromethyl-phenyl)-acrylamide;
(E)-N-(1-Isopropyl-piperidin-4-yl)-N-[3-(methyl-pyridin-4-yl-amino)-benzyl]-3-(4-trifluoromethyl-phenyl)-acrylamide;
(E)-N-(1-Benzyl-piperidin-4-yl)-3-(4-isopropoxy-phenyl)-N-[4-(methyl-pyridin-4-yl-amino)-benzyl]-acrylamide;
(E)-N-(1-Benzyl-piperidin-4-yl)-3-(4-tert-butyl-phenyl)-N-[4-(methyl-pyridin-4-yl-amino)-benzyl]-acrylamide;
(E)-N-(1-Benzyl-piperidin-4-yl)-3-(4-difluoromethoxy-phenyl)-N-[4-(methyl-pyridin-4-yl-amino)-benzyl]-acrylamide;
(E)-N-(1-Benzyl-piperidin-4-yl)-N-[4-(methyl-pyridin-4-yl-amino)-benzyl]-3-(4-trifluoromethoxy-phenyl)-acrylamide;
(E)-N-(1-Benzyl-piperidin-4-yl)-3-(4-ethyl-phenyl)-N-[4-(methyl-pyridin-4-yl-amino)-benzyl]-acrylamide;
(E)-N-(1-Benzyl-piperidin-4-yl)-N-[4-(methyl-pyridin-4-yl-amino)-benzyl]-3-(4-propoxy-phenyl)-acrylamide;
(E)-N-(1-Benzyl-piperidin-4-yl)-3-(4-methoxy-phenyl)-N-[4-(methyl-pyridin-4-yl-amino)-benzyl]-acrylamide;
(E)-N-(1-Benzyl-piperidin-4-yl)-3-(3-methoxy-phenyl)-N-[4-(methyl-pyridin-4-yl-amino)-benzyl]-acrylamide;
(E)-N-(1-Benzyl-piperidin-4-yl)-3-(2-methoxy-phenyl)-N-[4-(methyl-pyridin-4-yl-amino)-benzyl]-acrylamide;
(E)-N-(1-Benzyl-piperidin-4-yl)-3-(4-chloro-phenyl)-N-[4-(methyl-pyridin-4-yl-amino)-benzyl]-acrylamide;
(E)-N-(1-Benzyl-piperidin-4-yl)-3-(3-chloro-phenyl)-N-[4-(methyl-pyridin-4-yl-amino)-benzyl]-acrylamide;
(E)-N-(1-Benzyl-piperidin-4-yl)-3-(2-chloro-phenyl)-N-[4-(methyl-pyridin-4-yl-amino)-benzyl]-acrylamide;
(E)-N-(1-Benzyl-piperidin-4-yl)-3-(4-fluoro-phenyl)-N-[4-(methyl-pyridin-4-yl-amino)-benzyl]-acrylamide;
(E)-N-(1-Benzyl-piperidin-4-yl)-3-(3-fluoro-phenyl)-N-[4-(methyl-pyridin-4-yl-amino)-benzyl]-acrylamide;
(E)-N-(1-Benzyl-piperidin-4-yl)-3-(2-fluoro-phenyl)-N-[4-(methyl-pyridin-4-yl-amino)-benzyl]-acrylamide;
(E)-N-(1-Benzyl-piperidin-4-yl)-N-[4-(methyl-pyridin-4-yl-amino)-benzyl]-3-p-tolyl-acrylamide;
(E)-N-(1-Benzyl-piperidin-4-yl)-N-[4-(methyl-pyridin-4-yl-amino)-benzyl]-3-m-tolyl-acrylamide;
(E)-N-(1-Benzyl-piperidin-4-yl)-N-[4-(methyl-pyridin-4-yl-amino)-benzyl]-3-o-tolyl-acrylamide;
(E)-N-(1-Benzyl-piperidin-4-yl)-N-[4-(methyl-pyridin-4-yl-amino)-benzyl]-3-(6-trifluoromethyl-pyridin-3-yl)-acrylamide;
(E)-N-(1-Benzyl-piperidin-4-yl)-3-(4-methanesulfonyl-phenyl)-N-[4-(methyl-pyridin-4-yl-amino)-benzyl]-acrylamide;
(E)-N-(1-Benzyl-piperidin-4-yl)-3-(2,4-dimethyl-thiazol-5-yl)-N-[4-(methyl-pyridin-4-yl-amino)-benzyl]-acrylamide;
(E)-N-(1-Benzyl-piperidin-4-yl)-3-(1,5-dimethyl-1H-pyrazol-4-yl)-N-[4-(methyl-pyridin-4-yl-amino)-benzyl]-acrylamide;
(E)-N-(1-Benzyl-piperidin-4-yl)-N-[4-(methyl-pyridin-4-yl-amino)-benzyl]-3-(1,3,5-trimethyl-1H-pyrazol-4-yl)-acrylamide;
(E)-N-(3-Dimethylamino-propyl)-N-[4-(2-methyl-pyridin-4-ylamino)-benzyl]-3-(4-trifluoromethyl-phenyl)-acrylamide;
(E)-3-(4-Chloro-phenyl)-N-(3-dimethylamino-propyl)-N-[4-(2-methyl-pyridin-4-ylamino)-benzyl]-acrylamide;
(E)-N-(1-Cyclopentyl-piperidin-4-yl)-N-[6-(2-methyl-pyridin-4-ylamino)-pyridin-3-ylmethyl]-3-(4-trifluoromethyl-phenyl)-acrylamide;
(E)-3-(4-Chloro-phenyl)-N-(1-cyclopentyl-piperidin-4-yl)-N-[6-(2-methyl-pyridin-4-ylamino)-pyridin-3-ylmethyl]-acrylamide;
(E)-N-(1-Cyclopentyl-piperidin-4-yl)-N-[5-(2-methyl-pyridin-4-ylamino)-pyridin-2-ylmethyl]-3-(4-trifluoromethyl-phenyl)-acrylamide;
(E)-3-(4-Chloro-phenyl)-N-(1-cyclopentyl-piperidin-4-yl)-N-[5-(2-methyl-pyridin-4-ylamino)-pyridin-2-ylmethyl]-acrylamide;
(E)-N-(1'-Methyl-[1,4']bipiperidinyl-4-ylmethyl)-N-[4-(2-methyl-pyridin-4-ylamino)-benzyl]-3-(4-trifluoromethyl-phenyl)-acrylamide;
(E)-N-[4-(2-Methyl-pyridin-4-ylamino)-benzyl]-N-(3-morpholin-4-yl-propyl)-3-(4-trifluoromethyl-phenyl)-acrylamide;
(E)-N-(1-Methyl-piperidin-4-yl)-N-[4-(2-methyl-pyridin-4-ylamino)-benzyl]-3-(4-trifluoromethyl-phenyl)-acrylamide;
(E)-N-(4-Hydroxy-1-methyl-piperidin-4-ylmethyl)-N-[4-(2-methyl-pyridin-4-ylamino)-benzyl]-3-(4-trifluoromethyl-phenyl)-acrylamide;
(E)-N-(2-Dimethylamino-ethyl)-N-[4-(2-methyl-pyridin-4-ylamino)-benzyl]-3-(4-trifluoromethyl-phenyl)-acrylamide;

(E)-N-(1-Benzyl-piperidin-4-yl)-N-{4-[methyl-(1-methyl-piperidin-4-yl)-amino]-benzyl}-3-(4-trifluoromethyl-phenyl)-acrylamide;
(E)-N-(1-Benzyl-piperidin-4-yl)-N-{4-[methyl-(1-methyl-piperidin-4-yl)-amino]-benzyl}-3-(4-trifluoromethoxy-phenyl)-acrylamide;
(E)-3-(4-Cyano-phenyl)-N-(1'-methyl-[1,4']bipiperidinyl-4-yl)-N-[4-(methyl-pyridin-4-yl-amino)-benzyl]-acrylamide;
(E)-3-(4-Chloro-phenyl)-N-(1'-methyl-[1,4']bipiperidinyl-4-yl)-N-[4-(methyl-pyridin-4-yl-amino)-benzyl]-acrylamide;
(E)-3-(4-Difluoromethoxy-phenyl)-N-(1'-methyl-[1,4']bipiperidinyl-4-yl)-N-[4-(methyl-pyridin-4-yl-amino)-benzyl]-acrylamide;
(E)-N-(1'-Methyl-[1,4']bipiperidinyl-4-yl)-N-[4-(methyl-pyridin-4-yl-amino)-benzyl]-3-phenyl-acrylamide;
(E)-N-(1'-Methyl-[1,4']bipiperidinyl-4-yl)-N-[4-(methyl-pyridin-4-yl-amino)-benzyl]-3-(6-trifluoromethyl-pyridin-3-yl)-acrylamide;
(E)-N-(1-Cyclopentyl-piperidin-4-yl)-N-{4-[methyl-(2-methyl-pyridin-4-yl)-amino]-benzyl}-3-(4-trifluoromethyl-phenyl)-acrylamide;
(E)-N-[4-(3-Diethylaminomethyl-4-hydroxy-phenylamino)-benzyl]-N-(1-methyl-piperidin-4-yl)-3-(4-trifluoromethyl-phenyl)-acrylamide;
(E)-N-(1-Isopropyl-piperidin-4-yl)-N-[4-(2-methyl-pyridin-4-ylamino)-benzyl]-3-(4-trifluoromethyl-phenyl)-acrylamide;
(E)-N-(1'-Methyl-[1,4']bipiperidinyl-4-ylmethyl)-N-[4-(methyl-pyridin-4-yl-amino)-benzyl]-3-(4-trifluoromethyl-phenyl)-acrylamide;
(E)-N-(1-Cyclopentyl-piperidin-4-ylmethyl)-N-[4-(methyl-pyridin-4-yl-amino)-benzyl]-3-(4-trifluoromethyl-phenyl)-acrylamide;
(E)-N-[1-(3-Methyl-butyl)-piperidin-4-ylmethyl]-N-[4-(methyl-pyridin-4-yl-amino)-benzyl]-3-(4-trifluoromethyl-phenyl)-acrylamide;
(E)-N-(4-Dimethylamino-cyclohexyl)-N-[4-(methyl-pyridin-4-yl-amino)-benzyl]-3-(4-trifluoromethyl-phenyl)-acrylamide;
(E)-N-(4-Dimethylamino-cyclohexyl)-N-[4-(methyl-pyridin-4-yl-amino)-benzyl]-3-(4-trifluoromethyl-phenyl)-acrylamide;
(E)-N-[4-(Methyl-pyridin-4-yl-amino)-benzyl]-N-(4-pyrrolidin-1-yl-cyclohexyl)-3-(4-trifluoromethyl-phenyl)-acrylamide;
(E)-N-[4-(Methyl-pyridin-4-yl-amino)-benzyl]-N-(4-pyrrolidin-1-yl-cyclohexyl)-3-(4-trifluoromethyl-phenyl)-acrylamide;
(E)-N-(1'-Methyl-[1,4']bipiperidinyl-4-yl)-N-[4-(pyridine-4-carbonyl)-benzyl]-3-(4-trifluoromethyl-phenyl)-acrylamide;
(E)-N-[1-(2-Dimethylamino-ethyl)-piperidin-4-yl]-N-[4-(methyl-pyridin-4-yl-amino)-benzyl]-3-(4-trifluoromethyl-phenyl)-acrylamide;
(E)-N-(1-Cyclopentyl-piperidin-4-yl)-N-[4-(2-methyl-pyridin-4-yl)-benzyl]-3-(4-trifluoromethyl-phenyl)-acrylamide;
(E)-N-(1-Cyclopentyl-piperidin-4-yl)-N-(4-pyridin-3-yl-benzyl)-3-(4-trifluoromethyl-phenyl)-acrylamide;
(E)-N-(1-Cyclopentyl-piperidin-4-yl)-N-(4-pyridin-2-yl-benzyl)-3-(4-trifluoromethyl-phenyl)-acrylamide;
(E)-N-(1-Cyclopentyl-piperidin-4-yl)-N-[4-(4-isopropyl-piperazin-1-yl)-benzyl]-3-(4-trifluoromethyl-phenyl)-acrylamide;
(E)-N-(1-Cyclopentyl-piperidin-4-yl)-N-[4-(4-methyl-piperazin-1-yl)-benzyl]-3-(4-trifluoromethyl-phenyl)-acrylamide;
(E)-N-(1-Cyclopentyl-piperidin-4-yl)-N-[4-(2-methyl-thiazol-5-yl)-benzyl]-3-(4-trifluoromethyl-phenyl)-acrylamide;
(E)-N-(1-Cyclopentyl-piperidin-4-yl)-N-[4-(1-methyl-1H-pyrazol-3-yl)-benzyl]-3-(4-trifluoromethyl-phenyl)-acrylamide;
(E)-N-(1-Cyclopentyl-piperidin-4-yl)-N-(4-pyrimidin-2-yl-benzyl)-3-(4-trifluoromethyl-phenyl)-acrylamide;
(E)-N-(1-Cyclopentyl-piperidin-4-yl)-N-(4-pyrimidin-5-yl-benzyl)-3-(4-trifluoromethyl-phenyl)-acrylamide;
(E)-N-(1-Cyclopentyl-piperidin-4-yl)-N-[4-(3-dimethylamino-propoxy)-benzyl]-3-(4-trifluoromethyl-phenyl)-acrylamide;
(E)-N-(1-Cyclopentyl-piperidin-4-yl)-N-(2-pyrrolidin-1-yl-pyridin-4-ylmethyl)-3-(4-trifluoromethyl-phenyl)-acrylamide;
(E)-N-(1-Cyclopentyl-piperidin-4-yl)-N-[4-(pyridin-4-yloxy)-benzyl]-3-(4-trifluoromethyl-phenyl)-acrylamide;
(E)-N-(1-Cyclopentyl-piperidin-4-yl)-N-[4-(2,6-dimethyl-pyridin-4-yloxy)-benzyl]-3-(4-trifluoromethyl-phenyl)-acrylamide;
(E)-3-(4-Chloro-phenyl)-N-(2-dimethylamino-1-methyl-ethyl)-N-[4-(2-methyl-pyridin-4-ylamino)-benzyl]-acrylamide; and
(E)-3-(4-Chloro-phenyl)-N-(1-cyclopropyl-piperidin-4-yl)-N-[4-(2-methyl-pyridin-4-ylamino)-benzyl]-acrylamide;
or a pharmaceutically acceptable salt of such a compound.

9. A pharmaceutical composition comprising a compound according to claim 1, in free or pharmaceutically acceptable salt form, and a pharmaceutically acceptable carrier material.

10. A method for the treatment of malaria, said method comprising administering to a subject a pharmaceutically active amount of a compound according to claim 1, in free or pharmaceutically acceptable salt form.

11. A compound according to claim 3, wherein
X represents —NR$^4$— wherein R$^4$ represents hydrogen or methyl; and
R$^3$ represents
piperidin-4-yl which is optionally substituted on the nitrogen with (C$_{1-3}$)alkyl; or
6-membered heteroaryl selected from pyridinyl and pyrimidinyl, wherein said heteroaryl independently is unsubstituted, or mono-, or di-substituted wherein the substituents are independently selected from methyl, methoxy, and fluoro;
or a pharmaceutically acceptable salt of such a compound.

12. A compound according to claim 3, wherein R$^2$ represents heterocyclyl selected from piperidin-3-yl, piperidin-4-yl, 3-fluoro-piperidin-4-yl, 2-aza-spiro[3.3]hept-6-yl, and 3-aza-spiro[5.5]undec-9-yl; wherein said heterocyclyl is independently substituted on the ring nitrogen atom with with cyclopentyl or 1-methyl-piperidin-4-yl;
or a pharmaceutically acceptable salt of such a compound.

13. A compound according to claim 5, wherein R$^2$ represents heterocyclyl selected from piperidin-3-yl, piperidin-4-yl, 3-fluoro-piperidin-4-yl, 2-aza-spiro[3.3]hept-6-yl, and 3-aza-spiro[5.5]undec-9-yl; wherein said heterocyclyl is independently substituted on the ring nitrogen atom with with cyclopentyl or 1-methyl-piperidin-4-yl;
or a pharmaceutically acceptable salt of such a compound.

14. A compound according to claim 11, wherein $R^2$ represents heterocyclyl selected from piperidin-3-yl, piperidin-4-yl, 3-fluoro-piperidin-4-yl, 2-aza-spiro[3.3]hept-6-yl, and 3-aza-spiro[5.5]undec-9-yl; wherein said heterocyclyl is independently substituted on the ring nitrogen atom with with cyclopentyl or 1-methyl-piperidin-4-yl;

or a pharmaceutically acceptable salt of such a compound.

\* \* \* \* \*